United States Patent
Burdick et al.

(10) Patent No.: US 10,821,285 B2
(45) Date of Patent: Nov. 3, 2020

(54) DUELING BANDITS ALGORITHM FOR NEUROMODULATION THERAPY

(71) Applicants: California Institute of Technology, Pasadena, CA (US); Nicholas A. Terrafranca, Laguna Niguel, CA (US)

(72) Inventors: Joel W. Burdick, Pasadena, CA (US); Yanan Sui, Pasadena, CA (US); Yisong Yue, Glendale, CA (US); Nicholas A. Terrafranca, Laguna Niguel, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/475,856

(22) PCT Filed: Jan. 5, 2018

(86) PCT No.: PCT/US2018/012525
§ 371 (c)(1),
(2) Date: Jul. 3, 2019

(87) PCT Pub. No.: WO2018/129280
PCT Pub. Date: Jul. 12, 2018

(65) Prior Publication Data
US 2019/0374777 A1    Dec. 12, 2019

Related U.S. Application Data

(60) Provisional application No. 62/442,862, filed on Jan. 5, 2017.

(51) Int. Cl.
*A61N 1/36*    (2006.01)

(52) U.S. Cl.
CPC ...... *A61N 1/36117* (2013.01); *A61N 1/36062* (2017.08); *A61N 1/36132* (2013.01); *A61N 1/36157* (2013.01); *A61N 1/36175* (2013.01)

(58) Field of Classification Search
CPC ............ A61N 1/36117; A61N 1/36062; A61N 1/36132; A61N 1/36157; A61N 1/36175;
(Continued)

(56) References Cited

U.S. PATENT DOCUMENTS 6,748,276 B1    6/2004 Daignault et al.
7,949,403 B2    5/2011 Palermo et al.
(Continued)

OTHER PUBLICATIONS

Yue, Y. et al., "The K-armed dueling bandits problem"; Journal of Computer and Systems Sciences 2012 vol. 78 1538-1556 (Year: 2012).*
(Continued)

*Primary Examiner* — Gary Jackson
*Assistant Examiner* — Sebastian X Lukjan
(74) *Attorney, Agent, or Firm* — K&L Gates LLP

(57) ABSTRACT

A system, method, and apparatus for identifying optimal or near optimal complex stimulation waveforms for a neurostimulator device or neuromodulation device are disclosed. An example method includes using a dueling bandits algorithm with correlation among stimulation arms to select a batch of stimulation arms for sequential application to a patient during a therapy session. Each of the stimulation arms specifies complex stimulation waveform parameter values. Feedback from applying the stimulation arms to the patient is recorded and used to update feedback reward values corresponding to at least some of the stimulation arms using a stimulation arm correlation index. A second batch of stimulations arms is selected based upon the updated feedback reward values and applied to a patient. The method is iteratively repeated over a number of therapy sessions until an optimal or near optimal batch of stimulation arms (defining complex stimulation waveforms) is determined.

21 Claims, 27 Drawing Sheets

(58) Field of Classification Search
CPC .......... A61N 1/36067; A61N 1/36071; A61N 1/36021; A61N 1/36017; A61B 2562/046; A61B 5/4848; A61B 5/4836; A61B 5/686; A61B 5/04001; A61B 5/04012; A61B 5/0488
See application file for complete search history.

(56) References Cited

U.S. PATENT DOCUMENTS

| | | | |
|---|---|---|---|
| 10,092,750 B2 * | 10/2018 | Edgerton | ............... A61N 1/06 |
| 2002/0188332 A1 | 12/2002 | Lurie et al. | |
| 2011/0054567 A1 * | 3/2011 | Lane | ...................... A61N 1/08 607/59 |
| 2013/0289380 A1 | 10/2013 | Molnar et al. | |
| 2015/0231396 A1 | 8/2015 | Burdick et al. | |
| 2016/0121109 A1 | 5/2016 | Edgerton et al. | |

OTHER PUBLICATIONS

Sui et al., Clinical Online Recommendation with Subgroup Rand Feedback, Oct. 10, 2014—4 pages.
International Preliminary Report on Patentability PCT/US2018/012525 dated Jul. 18, 2019—6 pages.
International Search Report PCT/US2018/012525 dated Apr. 3, 2018—3 pages.
Written Opinion of the International Searching Authority dated Apr. 3, 2018—4 pages.
Onur Alan et al., "Global Bandits," Arxiv.org, Cornell University Library, 201 Olin Library Cornell University Ithaca, NY Mar. 29, 2015, XP081353767.
Mahler Jeffrey et al., "Dex-Net 1.0: A cloud-based network of 3D objects for robust grasp planning using a Multi-Armed Bandit model with correlated rewards", 2016 IEEE International Conference on Robotics and Automation (ICRA), IEEE, May 16, 2016, pp. 1957-1964, XP032908412.
Chapelle et al., "An Empirical Evaluation of Thompson Sampling," Yahoo Research, Santa Clara, CA, 9 pages.
Gajane et al., "A Relative Exponential Weighing Algorithm for Adversarial Utility-based Dueling Bandits," Orange-labs, Lannion, France,10 pages.
Kocsis et al, "Bandit based Monte-Carlo Planning," Computer and Automation Research Institute of the HungarianAcademyh of Sciences, Lende u. 13-17, 111 Budapest, Hungary, 12 pages.
Yue et al., "Beat the Mean Bandit", 8 pages.
Sui, "Clinical Online Recommendation with Subgroup Rank Feedback", 4 pages.
Abernethy et al., "Competing in the Dark: An Efficient Algorithm for Bandit Liner Optimization", 11 pages.
Dudik et al., Contextual Dueling Bandits, JML.R: Workshop and Conference Proceedings vol. 40: 1-25, Jun. 13, 2015, 25 pages.
Zoghi et al., Copeland Dueling Bandits, 9 pages.
Harkema et al., "Effect of epidural stimulation of the lumbosacral spinal cord on voluntary movement, standing, and assisted stepping after motor complete paraplegia: a case study"Lancet 2011; 377: pp. 1938-1947, published online May 20, 2011 D01: 10.1016/S0140-6736(11) 60547-3.
Rejc et al., "Effects of Lumbosacral Spinal Cord Epidural Stimulation for Standing after Chronic Complete Paralysis in Humans," Published: Jul. 24, 2015 https://doi.org10.1371/journal.pone.0133998, 14 pages.
Auer et al., "Finite-time Analysis of the Multiarmed Bandit Problem," Machine Learning, 47, 235-256, 2002.
Srinivas et al., "Gaussian Process Optimization in the Bandit Setting: No Regret and Experimental Design", Jun. 9, 2010, 17 pages.
Yadkori et al., "Improved Algorithms for Linear Stochastic Bandits", 9 pages.
Yue et al., "Interactively Optimizing Information Retrieval Systems as a Dueling Bandits Problem," Department of Computer Science, Cornell University, Ithaca, NY, 8 pages.
Chapelle et al., "Large-Scale Validation and Analysis of Interleaved Search Evaluation," ACM Transaction on Information Systems, vol. 30, No. 1, Article 6, Publication date: Feb. 2012, 41 pages.
Russo et al., "Learning to Optimize Via Posterior Sampling," Mathematics of Operations Research, vol. 00, No. 0, ISSN 0364-765X |EISSN 1526-5471, Feb. 3, 2014, 29 pages.
Kleinberg, "Multi-Armed Bandits in Metric Space," STOC'08, May 17-20, 2008, Copyright 2008 ACM 978-1-60558-047-0/008/05, 10 pages.
Bubeck et al., "OnlineOptimization in X-Armed Bandits", 8 pages.
Ailon et al., "Reducing Dueling Bandits to Cardinal Bandits," Proceedings of the 31st International Conference on Machines Learning, Beijing, China 2014, JMLR: W&CP, vol. 32, copyright 2014 by the author(s), 9 pages.
Bubeck et al., "Regret Analysis of Stochastic and Nonstochastic Multi-armed Bandit Problems," Foundations and Trends in Machines Learning, vol. 5, No. 1 (2012) 1-122.
Cesa-Bianchi et al., "Regret Minimization Under Partial Monitoring," Mathematics of Operations Research, copyright 200x Informs, 21 pages.
Whiteson et al., Relative Upper Confidence Bound for the K-Armed Dueling Bandit Problem, Proceedings of the 31st International Conference on Machine Learning, Beijing, China 2014 JMLR: W&CP, vol. 32, Copyright 2014 by the author(s), 9 pages.
Robbins, "Some Aspects of the Sequential Design of Experiments", 9 pages.
Jamieson et al., "Sparse Dueling Bandits", Department of Electrical and Computer Engineering, University of Wisconsin, Madison, dated Jan. 21, 2015, 21 pages.
Dani, "Stochastic Linear Optimization under Bandit Feedback", Department of Computer Science, University of Chicago, Toyota Technological Institute at Chicago 12 pages.
Yue et al., "The K-armed Dueling Bandits Problem", 10 pages.
Auer et al., "The Nonstochastic Multiarmed Bandit Problem," Society for Industrial and Applied Mathematics, Siam J. Comput., vol. 32, No. 1, pp. 48-77.

* cited by examiner

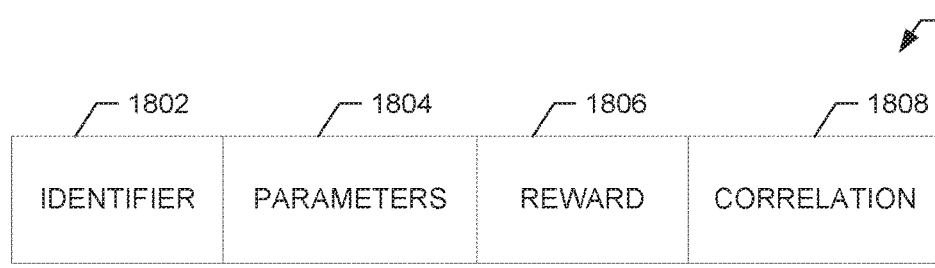

FIG. 18

| Parameter | Specification Value | Specification Value |
|---|---|---|
| # of channels | 32 | 4 |
| Frequency | 0.2 - 100 (Hz) | 0.2 - 100 (Hz) |
| Pulse Width | 0.1-3.0 (msec) | 0.5-5 (msec) |
| System Type | Constant Current | Constant Current |
| Amplitude | 0.1 - 20 (mA) | 0 - 300 (mA) |
| Overlapping Frequency | none | 4-10 (kHz) |
| Mode | monophasic / biphasic | monophasic / biphasic |
| waveform | Arbitrary | Square Wave |
| # of leads | 4 total (8 electrodes each) | 4 |
| Stimulation Control | Independent control of each electrode's stimulation parameters | Independent control of each electrode's stimulation parameters |
| Therapy Duration | up to 8 hrs | up to 8 hrs |
| Placement of electrodes | Cervical/Thraco-lumbar/Lumbar/Sacral | Cervical/Thoracic/Lumbar/Sacral/Coccygeal |
| | | |
| | | |
| | | |

FIG. 19

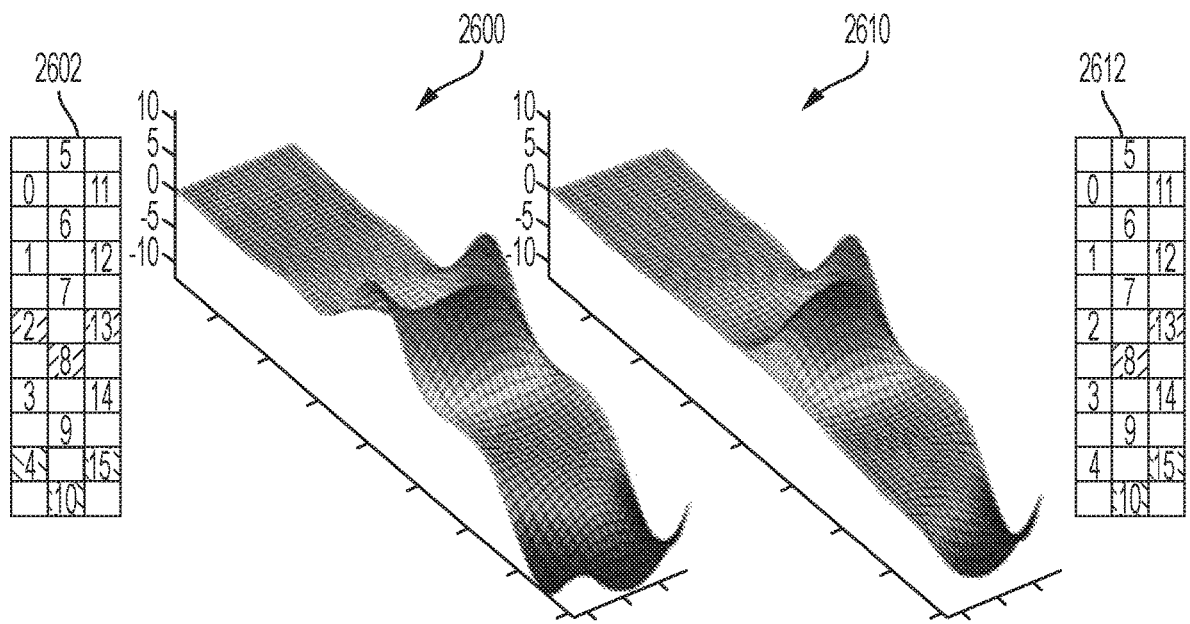
FIG. 26
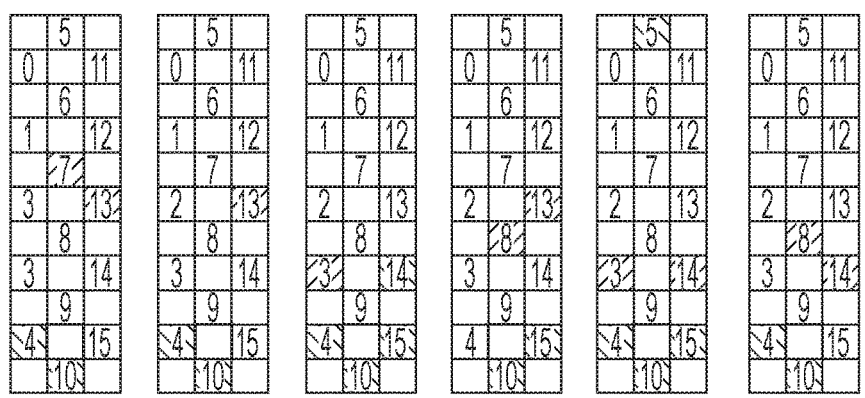
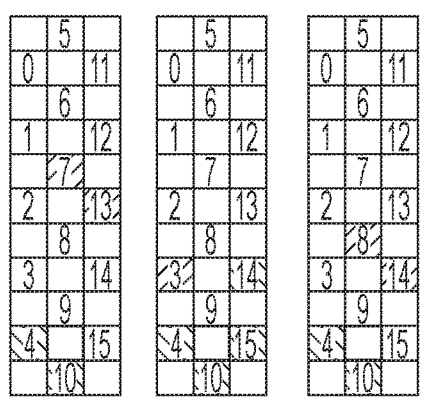
FIG. 27

DUELING BANDITS ALGORITHM FOR NEUROMODULATION THERAPY

PRIORITY CLAIM

This application is a national phase filing of PCT Application No. PCT/US2018/012525, filed Jan. 5, 2018, which claims the benefit of U.S. Provisional Application No. 62/442,862, filed Jan. 5, 2017, each of which is incorporated herein by reference in its entirety.

GOVERNMENT LICENSE RIGHTS

This invention was made with government support under Grant Nos. EB015521 and EB007615 awarded by the National Institutes of Health. The government has certain rights in the invention.

TECHNICAL FIELD

The present invention is directed generally to the field of medical electro-medical therapy devices, and more particularly to stimulators and stimulator systems for neurological rehabilitation in the treatment of traumatic and non-traumatic injury or illness.

BACKGROUND

Implantable neurostimulator or neuromodulation devices are used to treat a variety of conditions such as chronic pain, epilepsy, paralysis (e.g., an incomplete spinal cord injury ("SCI")), and tremor associated with and without Parkinson's Disease. The devices may be implantable (epidural) or transcutaneous, and configured to deliver stimulation therapy to targeted areas of a patient's nervous system. The applied therapy is usually in the form of electrical pulses provided at a set frequency. The device is attached via one or more leads to one or more electrodes or electrode arrays that are placed in close proximity to one or more nerves, one or more parts of a nerve, one or more nerve roots, the spinal cord, the brain stem, or within the brain itself. The leads and electrode arrays may vary in size, configuration, and length, and may be made of a biocompatible material.

In some instances, known multi-electrode arrays are implanted in the epidural space of a patient's spinal cord to treat debilitating back pain. More recently, multi-electrode arrays have been implanted in the epidural space over the lumbosacral and cervical spinal cord to facilitate the recovery of lost motor function following a spinal cord injury. Multi-site stimulation based on surface stimulating electrodes has also been used to treat individuals with spinal cord injury.

A multi-electrode array may contain anywhere between two to one hundred seventy-three (173) electrodes or more. Certain predetermined subgroups of electrodes are selected from the array for specified therapy types. In addition, different waveforms may be applied based on therapy type, patient response, etc. The waveforms are defined by stimuli parameters which specify, for example, active electrodes and their polarities, stimulation intensity (voltage or current amplitude) on each active electrode, stimulation frequencies on each electrode, a width (or duration) of the stimulating waveform, and/or a shape of the stimulating waveform. As one can image, there are potentially millions to billions of different combinations of electrode groups and stimuli parameters. However, a clinician does not have the luxury to test every single combination on a patient to determine an optimal electrode group and stimuli parameters. In addition, combinations of electrodes and stimuli parameters that are effective for one patient are not necessarily effective for other patients, which reduce the effectiveness of population-based models and therapy regimens. Any therapy time spent unproductively searching for optimal electrode groups and stimuli parameters reduces time spent actually treating the patient, thereby extending recovery time and patient frustration.

SUMMARY

The present disclosure provides a new and innovative system, method, and apparatus for determining or selecting complex stimulation waveforms for a neurostimulator device or neuromodulation device. The example system, method, and apparatus disclosed herein organizes complex stimulation waveforms available for patient therapies into correlated stimulation arms of a dueling bandits algorithm. The correlation among the stimulation arms enables the disclosed dueling bandits algorithm to converge relatively quickly on optimal or near optimal complex stimulation waveforms. For example, the example dueling bandits algorithm converges on optimal or near optimal complex stimulation waveforms within a week to ten days of therapy sessions with a patient, compared to manual stimulation waveform selection processes that may take three to six months to identify at least some of the same waveforms. In some instances using a closed loop system, the example dueling bandits algorithm converges on optimal or near optimal complex stimulation waveforms within seconds or minutes. Accordingly, the example dueling bandits algorithm operated by the system, method, and apparatus disclosed herein improves therapy outcomes for patients whom are treated with multi-electrode stimulation therapies for their chronic pain, epilepsy, paralysis, SCI, movement disorders, autonomic functional abnormalities, etc.

In an example embodiment, a neurostimulator device includes a stimulation assembly connectable to a plurality of electrodes that are configured to apply stimulation waveforms to stimulate a spinal cord, a portion of a spinal cord, a brain, a brainstem, a nerve, a portion of a nerve, a cell body, a ganglia, a nerve root, or targeted end organ or gland. The neurostimulator device also includes a memory storing a plurality of stimulation arms for a correlated dueling bandits algorithm, each of the stimulation arms comprising parameters for defining a stimulation waveform, and at least one electrode of the plurality of electrodes that are to be active for applying the stimulation waveform. The memory also stores a correlation index that specifies a correlation among at least some of the plurality of stimulation arms, and a feedback index that specifies a feedback reward value for at least some of the plurality of stimulation arms. The neurostimulator device further includes a processor communicatively coupled to the memory and electrically coupled to the stimulation assembly. The processor is configured to operate the correlated dueling bandits algorithm to select a first batch of a specified number of stimulation arms, among the plurality of stimulation arms and apply sequentially the stimulation waveforms corresponding to the stimulation arms of the first batch to a patient using the stimulation assembly. The processor is also configured to record a feedback reward value for each of the applied stimulation arms of the first batch indicative of an effectiveness of the respective stimulation arm for a therapy for the patient and update the feedback reward value for at least some of the plurality of stimulation arms using the correlation index specifying the correlation among the stimulation arms. Moreover, the processor is configured to operate the correlated dueling bandits algorithm to select a second batch of the specified number of stimulation arms, among the plurality of stimulation arms and apply sequentially the stimulation waveforms corresponding to the stimulation arms of the second batch to the patient using the stimulation assembly.

In another embodiment, a neurostimulator method includes operating a processor according to a correlated dueling bandits algorithm to select a first batch of a specified number of stimulation arms, among a plurality of stimulation arms, each of the stimulation arms comprising parameters for defining a stimulation waveform, and at least one electrode of the plurality of electrodes that are to be active for applying the stimulation waveform. The method also includes operating the processor to apply sequentially the stimulation waveforms corresponding to the stimulation arms of the first batch to a patient using a stimulation assembly comprising a plurality of electrodes that are configured to apply the stimulation waveforms to stimulate a portion of a patient's body and recording, via the processor, a feedback reward value for each of the applied stimulation arms of the first batch indicative of an effectiveness of the respective stimulation arm for a therapy for the patient. The example method further includes updating, via the processor, a feedback reward value for at least some of the plurality of stimulation arms using a correlation index specifying a correlation among at least some of the plurality of stimulation arms and operating the processor according to the correlated dueling bandits algorithm to select a second batch of the specified number of stimulation arms, among the plurality of stimulation arms. Moreover, the example method includes operating the processor to apply sequentially the stimulation waveforms corresponding to the stimulation arms of the second batch to the patient using the stimulation assembly.

In light of the technical features set forth herein, and without limitation, in a first aspect, a neurostimulator device includes a stimulation assembly connectable to a plurality of electrodes that are configured to apply stimulation waveforms to stimulate a portion of a patient's body, a memory storing a plurality of stimulation arms for a correlated dueling bandits algorithm, each of the stimulation arms comprising parameters for defining a stimulation waveform, and at least one electrode of the plurality of electrodes that are to be active for applying the stimulation waveform, a correlation index that specifies a correlation among at least some of the plurality of stimulation arms, and a feedback index that specifies a feedback reward value for at least some of the plurality of stimulation arms, and the neurostimulator device includes a processor communicatively coupled to the memory and electrically coupled to the stimulation assembly, the processor configured to operate the correlated dueling bandits algorithm to select a first batch of a specified number of stimulation arms, among the plurality of stimulation arms, apply sequentially the stimulation waveforms corresponding to the stimulation arms of the first batch to the patient using the stimulation assembly, record a feedback reward value for each of the applied stimulation arms of the first batch indicative of an effectiveness of the respective stimulation arm for a therapy for the patient, update the feedback reward value for at least some of the plurality of stimulation arms using the correlation index specifying the correlation among the stimulation arms, operate the correlated dueling bandits algorithm to select a second batch of the specified number of stimulation arms, among the plurality of stimulation arms, and apply sequentially the stimulation waveforms corresponding to the stimulation arms of the second batch to the patient using the stimulation assembly.

In a second aspect, which may be used with any other aspect described herein unless specified otherwise, the processor is configured to filter the plurality of stimulation arms based on at least one of a type of therapy or an indication of a placement of the plurality of electrodes in or on the patient.

In a third aspect, which may be used with any other aspect described herein unless specified otherwise, at least a portion of the correlation index and the feedback index are stored with the corresponding stimulation arms.

In a fourth aspect, which may be used with any other aspect described herein unless specified otherwise, the feedback reward value for each of the at least some of the plurality of stimulation arms is at least one of estimated from feedback reward values of correlated stimulation arms and determined from subjective or objective patient feedback to the respective stimulation arm.

In a fifth aspect, which may be used with any other aspect described herein unless specified otherwise, the neurostimulator device further includes a sensor configured to measure a response of the patient to the applied stimulation waveforms, wherein the processor is configured to determine the feedback reward value for each of the applied stimulation arms based on the measured response.

In a sixth aspect, which may be used with any other aspect described herein unless specified otherwise, the effectiveness of the respective stimulation arm is based on the patient's ability to show improved function in at least one of an autonomic function, such as bladder and bowel function, or a Cardiovascular function such as blood pressure regulation, during application of the stimulation waveforms.

In a seventh aspect, which may be used with the sixth aspect in combination with any other aspect described herein unless specified otherwise, the neurostimulator device is configured to provide blood pressure regulation by operating the correlated dueling bandits algorithm to determine optimized stimulation waveforms for application over an area of the patient's spinal cord between the 7th and 8th Thoracic vertebrae for 1 millisecond at 5 to 30 Hz using a monophasic waveform, from 0 to 10 milliamps or up to 70 milliamps.

In an eighth aspect, which may be used with any other aspect described herein unless specified otherwise, the effectiveness of the respective stimulation arm is based on the patient's ability to show improved musculoskeletal function while utilizing adjunctive rehabilitation devices and equipment during application of the stimulation waveforms.

In a ninth aspect, which may be used with any other aspect described herein unless specified otherwise, the effectiveness of the respective stimulation arm is based on the patient's ability to move a specified muscle group or limb during application of the stimulation waveform that is defined by the stimulation arm.

In a tenth aspect, which may be used with any other aspect described herein unless specified otherwise, the parameters for defining the stimulation waveform include at least one of a repetition frequency, a pulse width, a system type, a waveform amplitude, an overlapping frequency, and a waveform mode.

In an eleventh aspect, which may be used with any other aspect described herein unless specified otherwise, the portion of the patient's body includes at least one of a spinal cord, a portion of a spinal cord, a brain, a brainstem, a nerve, a portion of a nerve, a cell body, a ganglia, a nerve root, or targeted end organ or gland.

In a twelfth aspect, which may be used with any other aspect described herein unless specified otherwise, a neurostimulator method includes operating a processor according to a correlated dueling bandits algorithm to select a first batch of a specified number of stimulation arms, among a plurality of stimulation arms, each of the stimulation arms comprising parameters for defining a stimulation waveform, and at least one electrode of the plurality of electrodes that are to be active for applying the stimulation waveform, operating the processor to apply sequentially the stimulation waveforms corresponding to the stimulation arms of the first batch to a patient using a stimulation assembly comprising a plurality of electrodes that are configured to apply the stimulation waveforms to stimulate a portion of a patient's body, recording, via the processor, a feedback reward value for each of the applied stimulation arms of the first batch indicative of an effectiveness of the respective stimulation arm for a therapy for the patient, updating, via the processor, a feedback reward value for at least some of the plurality of stimulation arms using a correlation index specifying a correlation among at least some of the plurality of stimulation arms, operating the processor according to the correlated dueling bandits algorithm to select a second batch of the specified number of stimulation arms, among the plurality of stimulation arms, and operating the processor to apply sequentially the stimulation waveforms corresponding to the stimulation arms of the second batch to the patient using the stimulation assembly.

In a thirteenth aspect, which may be used with the twelfth aspect in combination with any other aspect described herein unless specified otherwise, the neurostimulator method further includes receiving, in the processor, a subjective score for each of the applied stimulation arms, and determining, via the processor, the feedback reward value as the subjective score.

In a fourteenth aspect, which may be used with the twelfth aspect in combination with any other aspect described herein unless specified otherwise, at least one of the stimulation arms of the second batch is more effective for the therapy than the stimulation arms of the first batch.

In a fifteenth aspect, which may be used with the twelfth aspect in combination with any other aspect described herein unless specified otherwise, at least some of the operations of the processor are repeated an n-number of times to converge upon an optimal or near optimal stimulation arm.

In a sixteenth aspect, which may be used with the twelfth aspect in combination with any other aspect described herein unless specified otherwise, n is between 2 and 100.

In a seventeenth aspect, which may be used with any other aspect described herein unless specified otherwise, a neurostimulator device includes a memory storing a plurality of stimulation arms for a correlated dueling bandits algorithm, each of the stimulation arms comprising parameters for defining a stimulation waveform, and at least one electrode of the plurality of electrodes that are to be active for applying the stimulation waveform, a correlation index that specifies a correlation among at least some of the plurality of stimulation arms, and a feedback index that specifies a feedback reward value for at least some of the plurality of stimulation arms, and the neurostimulator device includes a processor communicatively coupled to the memory, the processor configured to operate the correlated dueling bandits algorithm to select a first batch of a specified number of stimulation arms, among the plurality of stimulation arms, instruct a stimulation assembly to sequentially apply the stimulation waveforms corresponding to the stimulation arms of the first batch to a patient, receive a feedback reward value for each of the applied stimulation arms of the first batch indicative of an effectiveness of the respective stimulation arm for a therapy for the patient, update the feedback reward value for at least some of the plurality of stimulation arms using the correlation index specifying the correlation among the stimulation arms, operate the correlated dueling bandits algorithm to select a second batch of the specified number of stimulation arms, among the plurality of stimulation arms, and instruct the stimulation assembly to sequentially apply the stimulation waveforms corresponding to the stimulation arms of the second batch to the patient.

In an eighteenth aspect, which may be used with the seventeenth aspect in combination with any other aspect described herein unless specified otherwise, the processor is configured to filter the plurality of stimulation arms based on at least one of a type of therapy or an indication of a placement of the plurality of electrodes in or on the patient.

In a nineteenth aspect, which may be used with the seventeenth aspect in combination with any other aspect described herein unless specified otherwise, the correlation index specifies a closeness of feedback response values among the stimulation arms.

In a twentieth aspect, which may be used with the seventeenth aspect in combination with any other aspect described herein unless specified otherwise, the feedback index includes a confidence interval for each of the feedback reward values.

In a twenty-first aspect, any of the features, functionality and alternatives described in connection with any one or more of FIGS. 1 to 28 may be combined with any of the features, functionality and alternatives described in connection with any of the other one or more of FIGS. 1 to 28.

It is accordingly an advantage of the present disclosure to provide a neurostimulator device that operates a dueling bandits algorithm with correlated arms to quickly converge upon optimal or near optimal complex stimulation waveforms for treating a patient.

Additional features and advantages of the disclosed system, method, and apparatus are described in, and will be apparent from, the following Detailed Description and the Figures.

BRIEF DESCRIPTION OF THE FIGURES

FIG. 18 illustrates an arm for a dueling bandits algorithm, according to an example embodiment of the present disclosure.

FIG. 19 illustrates waveform parameters for the arm of FIG. 18, according to an example embodiment of the present disclosure.

FIGS. 23 to 27 illustrate experimental results from using the example dueling bandits algorithm described in connection with FIGS. 18 to 22, according to example embodiments of the present disclosure.

DETAILED DESCRIPTION

Figure 1:
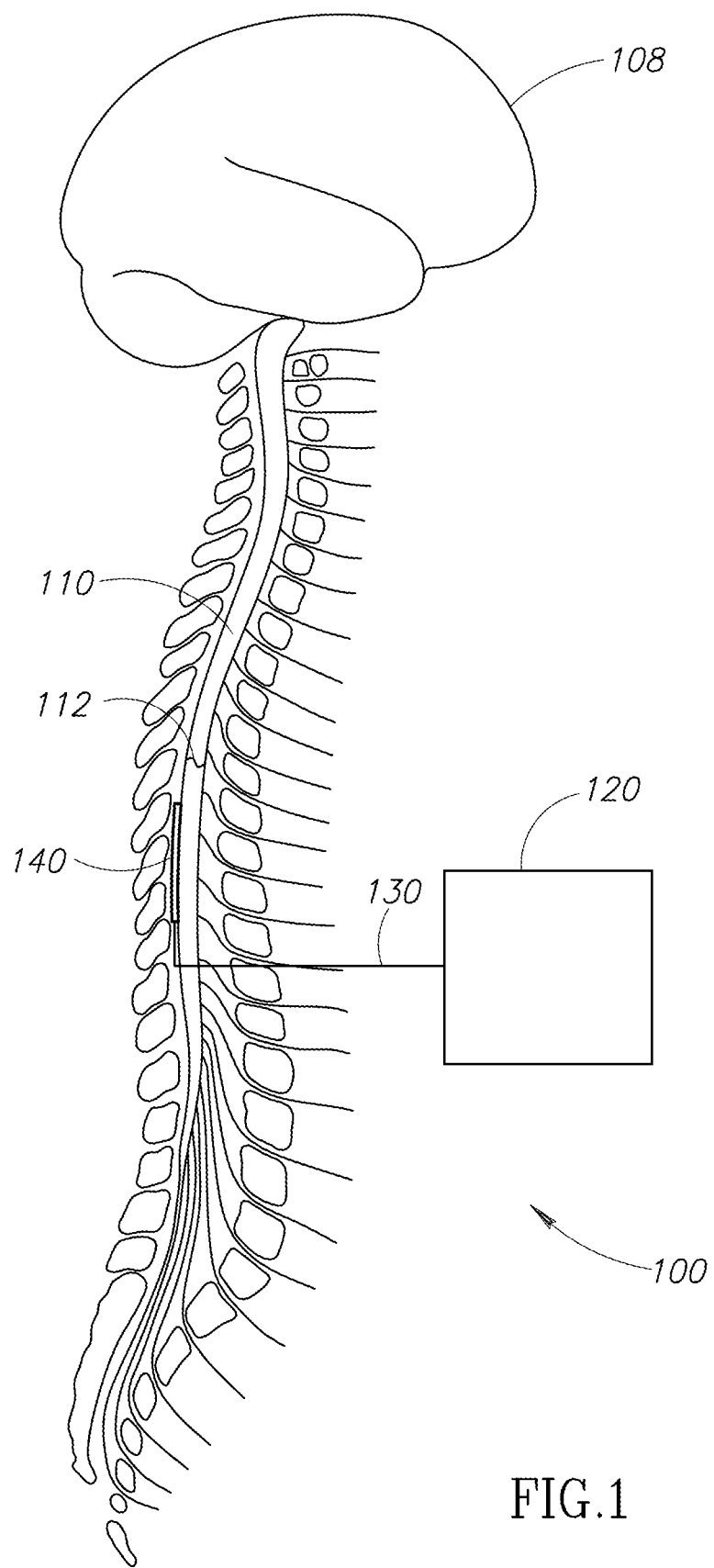
FIG. 1 is an illustration of an implantable assembly, according to an example embodiment of the present disclosure.

The present disclosure is generally directed to a neuromodulation and/or neurostimulation system, method, and device configured to determine or otherwise select an optimal group of electrodes and stimuli parameters for improving a patient's function after a spinal cord injury, a stroke, an injury or illness leading to paralysis, a loss or decrease in movement, or a loss or decrease in function whether it be musculoskeletal, autonomic, cardiovascular, cellular, endocrine, or a cognitive function in a mammal or human. More specifically, the neuromodulation and/or neurostimulation device disclosed herein is configured to use a dueling bandits algorithm and/or routine to select an optimal (or next-optimal) group of electrodes and stimuli parameters for a patient. The dueling bandits algorithm uses correlation among different electrode groups/stimuli parameters to converge more quickly on an optimal solution for a patient. In some instances, the example dueling bandits algorithm may incorporate measurement data from a sensor or sensors in its optimization for selection of the next electrode, group of electrodes, and/or stimuli parameters to use.

Reference is made throughout to electrode groups. As discussed in more detail below, the neuromodulation and/or neurostimulation device includes two or more electrodes or an array of multiple electrodes configured to apply an electrical stimulation waveform or pattern to a patient. For any given therapy, a group or subset of the electrodes is selected while other electrodes are inactive. The selected electrodes are generally orientated in a pattern to facilitate an operation of specific and various neuromuscular feedback loops. In some embodiments, the selected electrodes apply complex stimulation waveforms to a related nerve or group of nerves, nerve bodies, neurons or neural connections, cells or cell bodies, cell structures, a spine, a brain, a brainstem and/or a target end organ or gland. In a potential pain application, the selected electrodes apply complex stimulation waveforms to modulate pain pathways. In autonomic function recovery (e.g., blood pressure regulation), the selected electrodes apply complex stimulation waveforms to modulate circuits that directly or indirectly affect autonomic functions. For each therapy session, one or more electrical stimulation waveform is applied to a patient via selected electrodes as a pulse or complex waveform train. The waveform is defined by a number of stimuli parameters including, for example, a frequency, a pulse width, a current type, a voltage amplitude, an overlapping frequency, a mode, a waveform shape, a duration, etc.

Research has shown that the most effective method for improving motor function after a SCI is to combine different strategies, as neurological deficits (such as those caused by SCI) are complex, and there is wide variability in the deficit profiles among patients. These strategies may include physical therapy and/or training, along with electrical stimulation (e.g., high-density epidural stimulation), and optionally one or more serotonergic agents, dopaminergic agents, noradregeneric agents, GABAergic agents, and and/or glycinergic agents. By way of non-limiting examples, the agents may include at least one of 8-OHDPAT, Way 100.635, Quipazine, Ketanserin, SR 57227A, Ondanesetron, SB 269970, Buspirone, Methoxamine, Prazosin, Clonidine, Yohimbine, SKF-81297, SCH-23390, Quinpirole, and Eticlopride. The agents may also include a pharmaceutical composition comprising at least one molecule selectively activating α2c adrenergic receptor subtype and/or a blocking α2a adrenergic receptor subtype. In some embodiments, the α2a antagonist is 2-[(4,5-Dihydro-1H-imidazol-2-yl)methyl]-2,3-dihydro-1-methyl-1H-isoindole (BRL-44408). In other embodiments, the molecule selectively activating α2c adrenergic receptor subtype includes (R)-3-nitrobiphenyline and a compound of Formula (1) provided below:

Formula 1

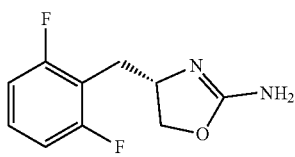

In other embodiments, the molecule can include Clonidine. Compositions can also include a 5-HT1 and/or 5-HT7 serotonergic agonist. Administration of the pharmaceutical agent maybe by an implantable pharmaceutical pump, i.e. an intrathecal pump or an in dwelling catheter and/or an external infusion pump.

It is believed that such a combination of strategies facilitates modulation of electrophysiological properties of spinal circuits in a patient so they are activated by proprioceptive input and indirectly use voluntary control of spinal cord circuits that are not normally available to connect the brain to the spinal cord. In other words, these strategies exploit the spinal circuitry and its ability to interpret proprioceptive information, and respond to that proprioceptive information in a functional way.

Electrical stimulation applied to the spinal cord via single or multiple electrodes or electrodes arrays either implanted in the epidural space or applied superficially over specific areas of the spinal cord enables paralyzed patients to achieve full weight-bearing standing, improvements in stepping, hand strength along with finger, hand and arm function, and partial recovery of lost autonomic functions. The electrical stimulation is only effective if the correct stimulation waveform and group of electrodes is used. However, the optimal stimulus pattern (the choice of active electrodes and their polarity, the pulse amplitude and width, and the pulse train frequency) varies significantly across patients and therapy types. For example, different stimulation patterns or waveforms are needed to facilitate different patient movements, functions, or treatments. In a spinal cord injury application, the movements of standing and stepping each require different stimulus parameters as do those for hand and arm control. In a daily application, a different stimulus set is often needed when the patient is sitting, lying, or standing. And even for the same patient, the outcome of the same stimulus varies across therapy sessions due to, for example, spinal cord plasticity, changes in bodily functions (bladder, bowel), or changes in co-morbidities. Hence, clinicians must determine the optimal stimulus for each patient under noisy conditions. Currently, the search for the optimal stimulating parameters and electrodes is a laborious and somewhat ad-hoc approach, which consumes valuable clinician and patient time and does not currently guarantee an optimal outcome. Further, the search for the optimal stimulating parameters and electrode generally requires a clinician or clinical personnel who is specifically trained to deliver a multi-electrode neurostimulation therapy.

In many online learning therapy environments, particularly those that involve patient feedback based on applied stimuli, reliable feedback is often limited to pairwise preferences. The patient feedback is oftentimes defined as a reward function, which quantifies how well a patient responds to the stimuli. Systems that use human feedback are conducive to the dueling bandits problem, which formalizes the problem of online regret minimization via preference feedback to applied stimuli.

The stochastic dueling bandits problem refers to an iterative decision making problem in which one repeatedly chooses among a decision set of K options, such as pulling one of K arms of a bandit machine. In each round, a reward is received that depends on the arm being selected. For example, assume that every reward is bounded between [0; 1] (as long as the rewards are bounded, one can shift and rescale them to fit within [0; 1]). The goal is to minimize the cumulative regret compared to the best arm. The regret of the $i^{th}$ arm is the difference in reward between that which is realized by selecting the $i^{th}$ arm and that which would be realized by selecting the optimal arm (which is a priori unknown). The cumulative regret is the regret that accumulates in all tests of the arms up until that point in time. In an adversarial setting, the rewards are chosen in an adversarial fashion, rather than sampled independently from some underlying distribution. In this case, regret is rephrased as the difference in the sum of rewards. The dueling bandits problem receives feedback in the form of a comparison between a pair of arms in each test. When the size of the decision set, K, is large, it is unavoidable to carry out a very large number of tests before the algorithm converges to its optimal solution.

Many known dueling bandits algorithms efficiently compute a dueling bandits problem with independent arms. Each arm corresponds to a specific configuration of active electrode groups and/or stimulation parameters. Feedback is measured for a particular arm (e.g., a stimulation arm) and used to select a next-best arm for a subsequent stimulation. In terms of a multi-electrode application, the known algorithms assume that the response of a patient to one specific stimulus is unrelated to the patient's response to any other stimulus. Hence, each possible stimulus had to be tested at multiple times during the process of finding the optimal stimuli. As a consequence, the process of stimulus optimization for complex multi-electrode arrays takes considerable time. The slowness of learning renders the approach of limited use in many clinical applications, where both patient and clinician time is valuable. The known dueling bandits algorithms are accordingly not efficient with many independent arms. Specifically, when the time horizon T is smaller than the number of arms K, it is virtually impossible to achieve low regret and identify optimal arms within the allotted time horizon. All dueling bandits algorithms must trade off exploration (searching the parameter space for good stimuli) and exploitation (choosing high performing stimuli to provide a good therapy) during the search process. Known dueling bandit algorithms, which assume the independence of arms, spend an excess amount of time on the exploration process, which limits the amount of time spent in the useful exploitation process, especially in a clinical setting having a limited time horizon.

The example neuromodulation and/or neurostimulation system, method, and device disclosed herein use a correlated dueling bandits algorithm or routine to determine optimal electrodes and stimuli parameters. The neuromodulation and/or neurostimulation system, method, and device use correlations among arms of stimuli to quickly converge on optimal stimuli (e.g., arm). The use of correlations among the arms reduces needed exploration among arms while exploiting correlations with known relatively high patient effectiveness.

The disclosed neuromodulation and/or neurostimulation system, method, and device disclosed herein uses patient response to stimuli to provide feedback regarding the effectiveness of a stimuli pattern or waveform. In some embodiments, the neuromodulation and/or neurostimulation system, method, and device use quantitative measurements (such as electromyographic ("EMG") signals, evoked potentials, force transducers or plate measurements, or kinematic data captured from video recording equipment) as patient feedback. In some additional embodiments, the disclosed neuromodulation and/or neurostimulation system may record field potentials from a neural system component, such somatosensory evoked potentials ("SSEPS") from the dorsum of a spinal cord. In other embodiments, the disclosed neuromodulation and/or neurostimulation system may record quantitative measurements and readings from sensors (such as temperature sensors, accelerometers, gyroscopes, flex-sensors, photonic or light sensors, chemical sensors, flow sensors) as feedback. The quantitative measurements may be normalized or scaled for more efficient computation.

In some embodiments, a patient's motor response to stimulation may be hard to quantify with measurements. For example, neither video motion capture nor EMG recordings of muscle activity may always provide a consistent and satisfactory measure of motor skill under stimulation. In these embodiments, the neuromodulation and/or neurostimulation system, method, and device disclosed herein maps performance to numerous combinations of muscle activities. While a patient's performance under a specific stimulus is hard to quantify, it can be compared to the responses to other stimuli. In other words, a patient's physiological or functional response may be mapped for performance to stimuli. Additionally or alternatively, the neuromodulation and/or neurostimulation system, method, and device can use subjective feedback from an observing clinician (or clinicians), as well as subjective feedback from the patient receiving the therapy, regarding the patient's relative response to different stimuli. The subjective measurements and/or subjective may be normalized or scaled for more efficient computation. The dueling bandits problem accordingly may formalize online learning problems with preference feedback instead of absolute rewards, and hence may be used for problems where the reward is not readily measured.

I. Implantable Device Embodiment

The example neuromodulation and/or neurostimulation system, method, and device disclosed herein may be implanted into a patient. FIG. 1 illustrates an implantable electrode array assembly 100. While the embodiment of the assembly 100 illustrated is configured for implantation in the human patient 102 (see FIG. 2), embodiments may be constructed for use in other patients, such as other mammals, including rats, and such embodiments are within the scope of the present teachings. The patient 102 has a brain 108, a spinal cord 110 with at least one selected spinal circuit (not shown), and a neurologically derived paralysis or loss of function (autonomic, cellular, vasomotor, endocrine, cognitive) in a portion of the patient's body. In the example discussed herein, the spinal cord 110 of the patient 102 has a lesion 112.

By way of non-limiting examples, when activated, the selected spinal circuit may (a) enable voluntary movement of muscles involved in at least one of standing, stepping, reaching, grasping, voluntarily changing positions of one or both legs and/or one or both arms, voiding the patient's bladder, voiding the patient's bowel, postural activity, and locomotor activity; (b) enable or improve autonomic control of at least one of cardiovascular function, body temperature regulation, and metabolic processes; (c) improve cellular function; and/or (d) help facilitate recovery of at least one of an autonomic function, sexual function, endocrine function, vasomotor function, and cognitive function. The effects of activation of the selected spinal circuit will be referred to as "improved neurological function."

Without being limited by theory, it is believed that the selected spinal circuit has a first stimulation threshold representing a minimum amount of stimulation required to activate the selected spinal circuit, and a second stimulation threshold representing an amount of stimulation above which the selected spinal circuit is fully activated and adding the induced neurological signals has no additional effect on the at least one selected spinal circuit.

The paralysis may be a motor complete paralysis or a motor incomplete paralysis. The paralysis may have been caused by a SCI classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Dystonia, Alzheimer's, ischemia, stroke, amyotrophic lateral sclerosis (ALS), primary lateral sclerosis (PLS), and cerebral palsy. By way of yet another example, there may be a loss of function in one or more of autonomic, cellular, vasomotor, cardiovascular, endocrine, or cognitive areas.

Neurological signals may be induced in the paralyzed portion of the patient's body (e.g., by physical training). However, adding the induced neurological signals may have little or no additional effect on the selected spinal circuit, if the induced neurological signals are below the first stimulation threshold and insufficient to activate the at least one selected spinal circuit.

The assembly 100 of FIG. 1 is configured to apply electrical stimulation to neurological tissue (e.g., a portion of the spinal cord 110, one or more spinal nerves, one or more nerve roots, cell bodies, ganglia, one or more peripheral nerves, the brain stem, and/or the brain 108, and the like). Further, the electrical stimulation may be applied to other types of tissue, including the tissue of one or more end organs (e.g., bladder, kidneys, heart, liver, and the like) or glands. For ease of illustration, the electrical stimulation will be described as being delivered to body tissue. While the stimulation may be delivered to body tissue that is not neurological tissue, the target of the stimulation is generally a component of the nervous system, or that which it innervates, whose function is usefully modified by the addition of the stimulation to the body tissue.

The electrical stimulation delivered is configured to be below the second stimulation threshold such that the selected spinal circuit is at least partially activatable by the addition of (a) induced neurological signals (e.g., neurological signals induced through physical training), and/or (b) supraspinal signals. By way of a non-limiting example, the assembly 100 may be used to perform methods described in U.S. patent application Ser. No. 13/342,903, filed Jan. 3, 2012, and titled High Density Epidural Stimulation for Facilitation of Locomotion, Posture, Voluntary Movement, and Recovery of Autonomic, Sexual, Vasomotor and Cognitive Function after Neurological Injury, which is incorporated herein by reference in its entirety. However, the selected spinal circuit may be at least partially activatable by the addition of neurological signals other than those induced by physical training.

The assembly 100 includes one or more electrode arrays 140, one or more leads 130, and a neurostimulator device 120. For ease of illustration, the one or more electrode arrays 140 will be described as including a single electrode array. However, through application of ordinary skill to the present teachings, embodiments may be constructed that include two or more electrode arrays. Therefore, such embodiments are within the scope of the present teachings. The neurostimulator device 120 generates electrical stimulation that is delivered to the electrode array 140 by the one or more leads 130. Depending upon the implementation details, the neurostimulator device 120 may be characterized as being a neuromodulator device.

The electrode array 140 may be implemented using commercially available high-density electrode arrays designed and approved for implementation in human patients. By way of a non-limiting example, a Medtronic Specify 5-6-5 multi-electrode array (incorporating 16 electrodes) may be used. Examples of suitable electrode arrays include paddle-shaped electrodes (e.g., having a 5-6-5 electrode configuration) constructed from surgical stainless steel covered by a platinum coating, with the surface electrodes embedded in silicone. Further, the electrode array 140 may be implemented using multiple electrode arrays (e.g., multiple 4, 8, 16 or 32-electrode arrays connected to the neurostimulator device 120 in a serial or parallel arrangement).

Figure 3A:
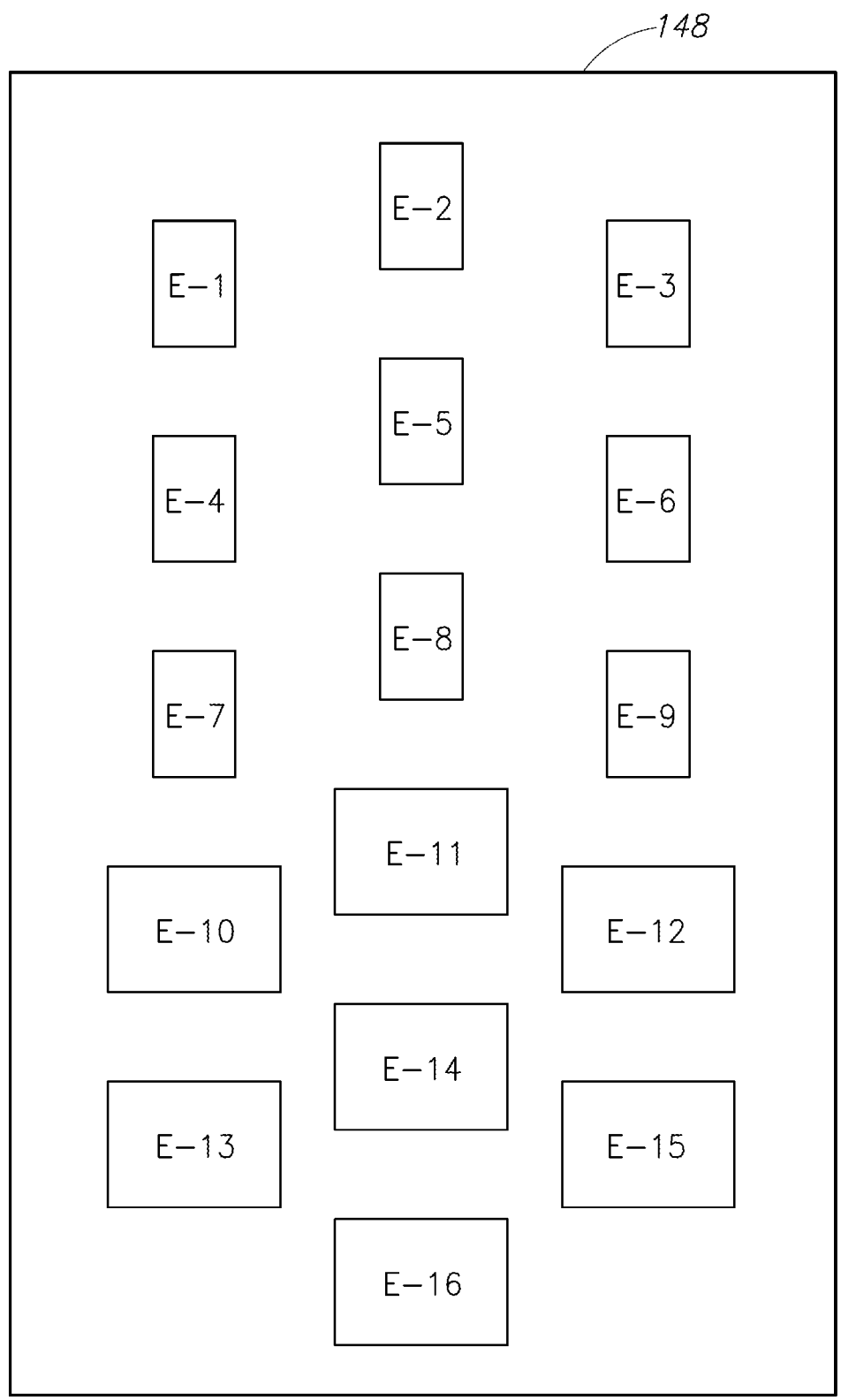
FIG. 3A is an illustration of a first embodiment of an exemplary electrode array for use with the neurostimulator device of the implantable assembly of FIG. 1.

FIG. 3A illustrates an electrode array 148 having 16 electrodes "E-1" to "E-16." The electrode array 140 may be implemented using the electrode array 148. Disclosed stimulators enable a user (e.g., a clinician) to divide the electrodes "E-1" to "E-16" into any number of groups. Each group may include any number of electrodes. In addition, each electrode may be assigned to its own group. By way of another example, one or more electrodes may belong to multiple groups. Stimulation waveforms or patterns having different frequency and pulse width may be delivered to one or more of the groups. Table A below provides examples of groups that may be identified and stimulated independently. Which electrodes function as the anode and which function as a cathode are also specified for illustrative purposes.

TABLE A

| Group Number | Anode electrodes | Cathode electrodes |
| --- | --- | --- |
| 1 | E-1 | E-3 |
| 2 | E-1 and E-2 | E-3, E-4, E-5, and E-6 |
| 3 | E-1, E-2, and E-3 | E-13, E-16, and E-15 |
| 4 | E-1, E-2, and E-3 | E-6, E-7, E-8, and E-9 |

The neurostimulator device 120 is configured to deliver stimulation to a single selected one of the electrodes 142 and/or use a single selected one of the electrodes 142 as a reference electrode. In some embodiments, the electrode array 140 and/or 148 may be constructed using microfabrication technology to place numerous electrodes in an array configuration on a flexible substrate. One suitable epidural array fabrication method was first developed for retinal stimulating arrays (see, e.g., Maynard, *Annu. Rev. Biomed. Eng.*, 3: 145-168 (2001); Weiland and Humayun, *IEEE Eng. Med. Biol. Mag.*, 24(5): 14-21 (2005)), and U.S. Patent Publications 2006/0003090 and 2007/0142878 which are incorporated herein by reference for all purposes (e.g., the devices and fabrication methods disclosed therein). In various embodiments the stimulating arrays comprise one or more biocompatible metals (e.g., gold, platinum, chromium, titanium, iridium, tungsten, and/or oxides and/or alloys thereof) disposed on a flexible material (e.g., parylene A, parylene C, parylene AM, parylene F, parylene N, parylene D, or other flexible substrate materials). Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, *Medical Device and Diagnostic Industry*, 22(8): 42-49 (2000)), and has flexibility characteristics (Young's modulus ~4 GPa (Rodger and Tai, *IEEE Eng. Med. Biology*, 24(5): 52-57 (2005))), lying in between those of PDMS (often considered too flexible) and most polyimides (often considered too stiff). Finally, the tear resistance and elongation at break of parylene are both large, minimizing damage to electrode arrays under surgical manipulation (Rodger et al., *Sensors and Actuators B-Chemical*, 117(1): 107-114 (2006)).

Figure 3B:
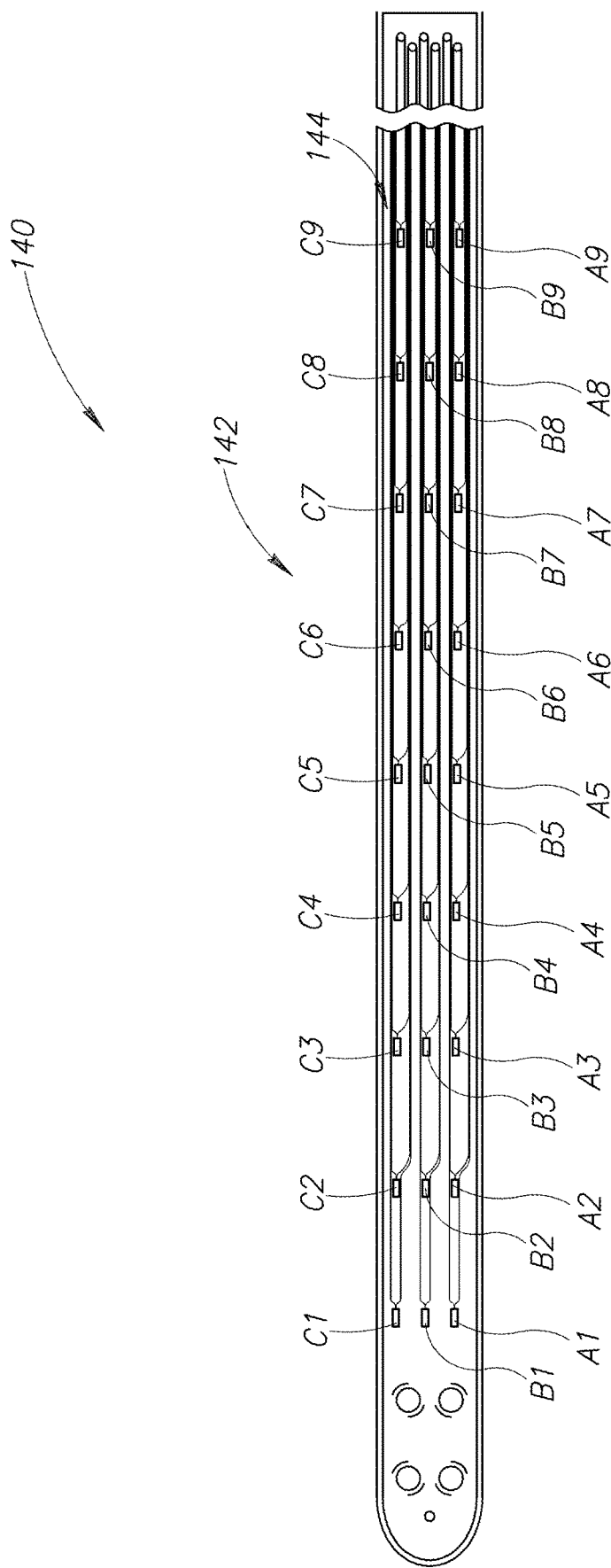
FIG. 3B is an illustration of a second embodiment of an exemplary electrode array for use with the neurostimulator device of the implantable assembly of FIG. 1.

In the embodiment illustrated in FIGS. 3A and 3B, the electrode array 140 and/or 148 may be characterized as being a microelectromechanical systems ("MEMS") device. While the implementation of the electrode array 140 and/or 148 illustrated in FIGS. 3A and 3B may be suited for use in animals, the basic geometry and fabrication technique can be scaled for use in humans. The electrode array 140 and/or 148 is configured for implantation along the spinal cord 110 (see FIG. 1) and to provide electrical stimulation thereto. For example, the electrode array 140 and/or 148 may provide epidural stimulation to the spinal cord 110. The electrode array 140 and/or 148 allows for a high degree of freedom and specificity in selecting the site of stimulation compared to prior art wire-based implants, and triggers varied biological responses that can lead to an increased understanding of the spinal cord 110 and improved neurological function in the patient 102. A non-limiting example of an electrode array that may be used to construct the electrode array 140 and/or 148 is described in co-pending U.S. patent application Ser. No. 13/356,499, filed on Jan. 23, 2012, and titled Parylene-Based Microelectrode Array Implant for Spinal Cord Stimulation, which is incorporated herein by reference in its entirety.

The electrode array 140 of FIG. 3B includes a plurality of electrodes 142 (e.g., electrodes A1-A9, B1-B9, and C1-C9), and a plurality of electrically conductive traces 144. The electrodes 142 may vary in size, and be constructed using a biocompatible substantially electrically conductive material (such as platinum, Ag/AgCl, and the like), embedded in or positioned on a biocompatible substantially electrically non-conductive (or insulating) material (e.g., flexible parylene). One or more of the traces 144 is connected to each of the electrodes 142. Connecting more than one of the traces 144 to each of the electrodes 142 may help ensure signals reach and are received from each of the electrodes 142. In other words, redundancy may be used to improve reliability. Each of the electrodes 142 has one or more electrically conductive contacts (not shown) positionable alongside body tissue. The body tissue may include neurological tissue (e.g., the spinal cord 110, one or more spinal nerves, one or more nerve roots, cell bodies, ganglia, one or more peripheral nerves, the brain stem, and/or the brain 108, and the like), other types of spinal tissue (e.g., the dura of the spinal cord 110), and the tissue of end organs or glands. Further, the electrode array 140 may be configured to be positionable alongside such body tissue.

The electrode array 140 of FIG. 3B may be implanted using any of a number of methods (e.g., a laminectomy procedure) well known to those of skill in the art. By way of a non-limiting example, the electrodes 142 may be implanted epidurally along the spinal cord 110 (see FIG. 1). By way of non-limiting example, the electrodes may be implanted subdurally. Additionally or alternatively, the electrodes 142 may be positioned at one or more of a lumbosacral region, a cervical region, and a thoracic region of the spinal cord 110 (see FIG. 1). In the embodiment illustrated, the electrodes 142 are positioned distal to the lesion 112 (see FIG. 1) relative to the brain 108 (see FIG. 1). In other words, the electrodes 142 are positioned farther from the brain 108 than the lesion 112. The electrodes 142 may be placed above and/or below the lesion 112.

The one or more leads 130 illustrated include electrically conductive elements. In some embodiments, the one or more leads 130 include an electrically conductive element for each of the traces 144 of the electrode array 140. By way of another non-limiting example, in some embodiments, the one or more leads 130 include an electrically conductive element for each of the electrodes 142 of the electrode array 140 and/or 148. The one or more leads 130 of the assembly 100 connect the neurostimulator device 120 to the traces 144 of the electrode array 140 and/or 148, which are each connected to one of the electrodes 142. Thus, a signal generated by the neurostimulator device 120 is transmitted via the one or more leads 130 to selected ones of the traces 144, which transmit the signal to selected ones of the electrodes 142, which in turn deliver the stimulation to the body tissue in contact with the electrically conductive contacts (not shown) of the electrodes 142. The one or more leads 130 may vary in length. The electrically conductive elements may be constructed using a biocompatible substantially electrically conductive material (such platinum, Ag/AgCl, and the like), embedded in or surrounded by a biocompatible substantially electrically non-conductive (or insulating) material (e.g., flexible parylene). Optionally, the one or more leads 130 may include one or more connectors 132 and 134. In the embodiment illustrated, the connector 132 is used to connect the one or more leads 130 to the electrode array 140 and/or 148 and the connector 134 is used to connect the one or more leads 130 to the neurostimulator device 220.

The example neurostimulator device 220 generate a complex pattern of stimulating signals needed to produce improved neurological and/or physiologic function (e.g., stepping, standing, arm movement, breathing, digestion, empting ones bowel or bladder, controlling ones blood pressure, and the like after a severe SCI or/and occurrence of a neuromotor or physiological disorder). For example, to recover stepping, an alternating spatiotemporal electric field having oscillations that peak over the right side of the spinal cord 110 (e.g., in the lumbosacral region) during a right leg swing phase, and oscillations that peak over the left side of the spinal cord 110 (e.g., in the lumbosacral region) during the left swing phase may be used. By way of another example, to recover independent standing, a rostral-caudal gradient in both electrode voltage and electrode stimulation frequency may be used. Rostral is nearer the brain 108 and caudal farther from the brain 108.

Figure 4A:
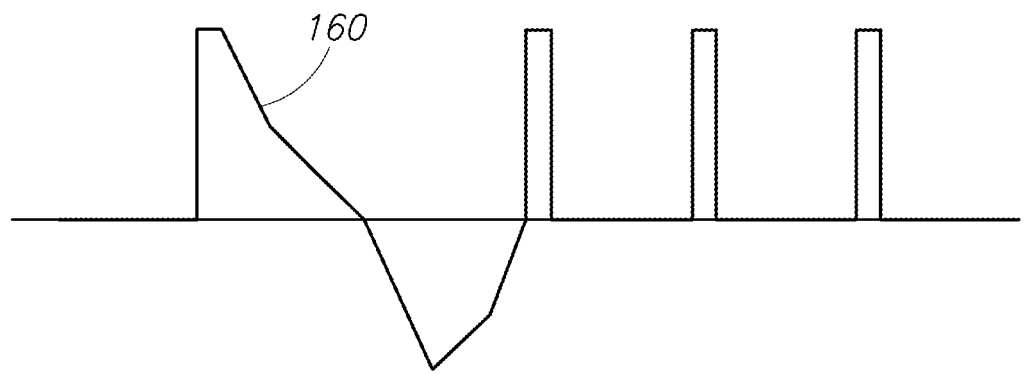
FIGS. 4A and 4B are illustrations of waveform that may be generated by the neurostimulator device of the implantable assembly of FIG. 1 or a transcutaneous assembly shown in FIGS. 13 and 14, according to example embodiments of the present disclosure.
Figure 4B:
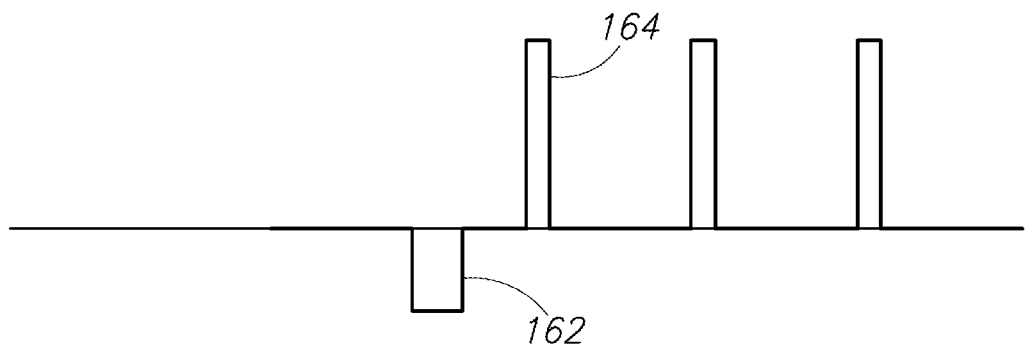

To achieve improved neurological function (e.g., stepping, standing, arm movement, and the like), a more complex waveform is delivered to one or more target locations. For example, it is known that non-rectangular waveforms (e.g., waveform 160 illustrated in FIG. 4A) and small "prepulses" (e.g., prepulse 162 illustrated in FIG. 4B) having a different amplitude and pulse width than the main "driving" pulse (e.g., driving pulse 164 illustrated in FIG. 4B) may be used to selectively recruit neurons with different fiber diameters and different electrical properties. Z.-P. Fang and J. T. Mortimer, "Selective Activation of Small Motor Axons by Quasitrapezoidal Current Pulses," *IEEE Trans. Biomedical Engineering*, 38(2):168-174, February 1991; and W. M. Grill and J. T. Mortimer, "Inversion of the Current-Distance Relationship by Transient Depolarization," *IEEE Trans. Biomedical Engineering*, 44(1):1-9, January 1997. Thus, these waveforms may be used to selectively recruit different parts of one or more sensory/motor circuits (e.g., activate different spinal circuits) as needed to achieve different therapeutic goals.

To achieve improved neurological function (e.g., stepping, standing, arm movement, and the like), the timing of the onset of electrical stimulation must be carefully controlled. For example, the spatio-temporal characteristics of the stimulating voltage fields needed for stepping require the ability to specify and control the phase shift (the exact timing of the onset of the stimulating waveform) between the electrodes 142, across the entire electrode array 140.

The neurostimulator device 120 is configured to generate complex types and patterns of electrical stimulation that achieve improved neurological function and/or other bodily functions. In other words, the neurostimulator device 120 is configured to generate (and deliver to the electrode array 140) one or more "complex stimulation patterns." In some examples, complex stimulation waveforms or patterns may provide for a period time for the recording an electrical potential from one or more of the electrodes in the array. A complex stimulation pattern has at least the following properties:

1. a type of stimulation to apply to each of the electrodes 142 (which may include the application of no stimulation to one or more selected electrodes 142, if appropriate), the type of stimulation is defined by stimulation type parameters that include waveform shape, amplitude, waveform period, waveform frequency, and the like, the electrodes 142 being individually addressable;
2. stimulation timing that indicates when stimulation is to be applied to each of the electrodes 142 (which defines a sequence for applying stimulation to the electrodes 142), stimulation timing is defined by timing parameters that include an onset of stimulation, relative delay between waveform onset on different electrodes, a duration during which stimulation is delivered, a duration during which no stimulation is delivered, and the like; and
3. transition parameters that define how one waveform may be smoothly adapted over time to change (or morph) into a different waveform. Such smooth changes between waveform patterns may be helpful for enabling complex motor function, such as the transition from sitting to standing.

Together the stimulation type parameters, timing parameters, and transition parameters are "stimulation parameters" that define the complex stimulation pattern. The neurostimulator device 120 delivers the complex stimulation pattern to the electrode array 140. Thus, the electrode array 140 is configured such that which of the electrodes 142 will receive stimulation may be selected. In particular embodiments, the electrodes 142 are individually addressable by the neurostimulator device 120. Further, the neurostimulator device 120 may also be configured such that the frequency, waveform width (or period), waveform shape, phase of a waveform (monophasic, bi-phasic), and/or amplitude of the stimulation delivered to each of the selected ones of the electrodes 142 may also be adjustable. The complex stimulation pattern may remain constant, repeat, or change over time.

The configurability of the complex stimulation patterns delivered by the neurostimulator device 120 (by changing the stimulation parameters) enables the identification of effective complex stimulation patterns and the adjustment of the complex stimulation patterns to correct for migration and/or initial surgical misalignment. The neurostimulator device 120 may be configured to deliver a plurality of different complex stimulation patterns to the electrodes 142.

The neurostimulator device 120 is programmable (e.g., by the patient 102 or a physician). The neurostimulator device 120 may be programmed with stimulation parameters and/or control parameters configured to deliver a complex stimulation pattern that is safe, efficacious, and/or selected to target specific body tissue. Further, stimulation parameters and/or control parameters may be customized for each patient (e.g., based on response to pre-surgical (implant) evaluation and testing). The neurostimulator device 120 may have a variable activation control for providing a complex stimulation pattern either intermittently or continuously, and allowing for adjustments to frequency, waveform width, shape, phase, amplitude, and duration. By generating such customizable stimulation, the neurostimulator device 120 may be used to (a) generate or maintain efficacious and/or optimal complex stimulation patterns, (b) adjust the location of the application of stimulation (relative to the neural tissue) when the assembly 100 migrates and/or was misaligned during implantation, and/or (c) facilitate the recovery of different functions (e.g., standing vs. stepping).

The neurostimulator device 120 may be configured to store, send, and receive data. The data sent and received may be transmitted wirelessly (e.g., using current technology, such as Bluetooth, ZigBee, FCC-approved MICS medical transmission frequency bands, and the like) via a wireless connection 155 (see FIG. 2). The neurostimulator device 120 may be configured to be regulated automatically (e.g., configured for open loop and/or closed loop functionality). Further, the neurostimulator device 120 may be configured to record field potentials detected by the electrodes 142, such as somatosensory evoked potentials (SSEPs) generated by the dorsum of the spinal cord 110. The neurostimulator device 120 may be configured to be rechargeable.

Depending upon the implementation details, the neurostimulator device 120 may be configured with one or more of the following properties or features:
1. a form factor enabling the neurostimulator device 120 to be implanted via a surgical procedure;
2. a power generator with rechargeable battery;
3. a secondary back up battery;
4. electronic and/or mechanical components encapsulated in a hermetic package made from one or more biocompatible materials;
5. programmable and autoregulatory;
6. ability to record field potentials;
7. ability to operate independently, or in a coordinated manner with other implanted or external devices or equipment (i.e. therapy equipment, robotic equipment); and
8. ability to send, store, and receive data via wireless technology.

Figure 2:
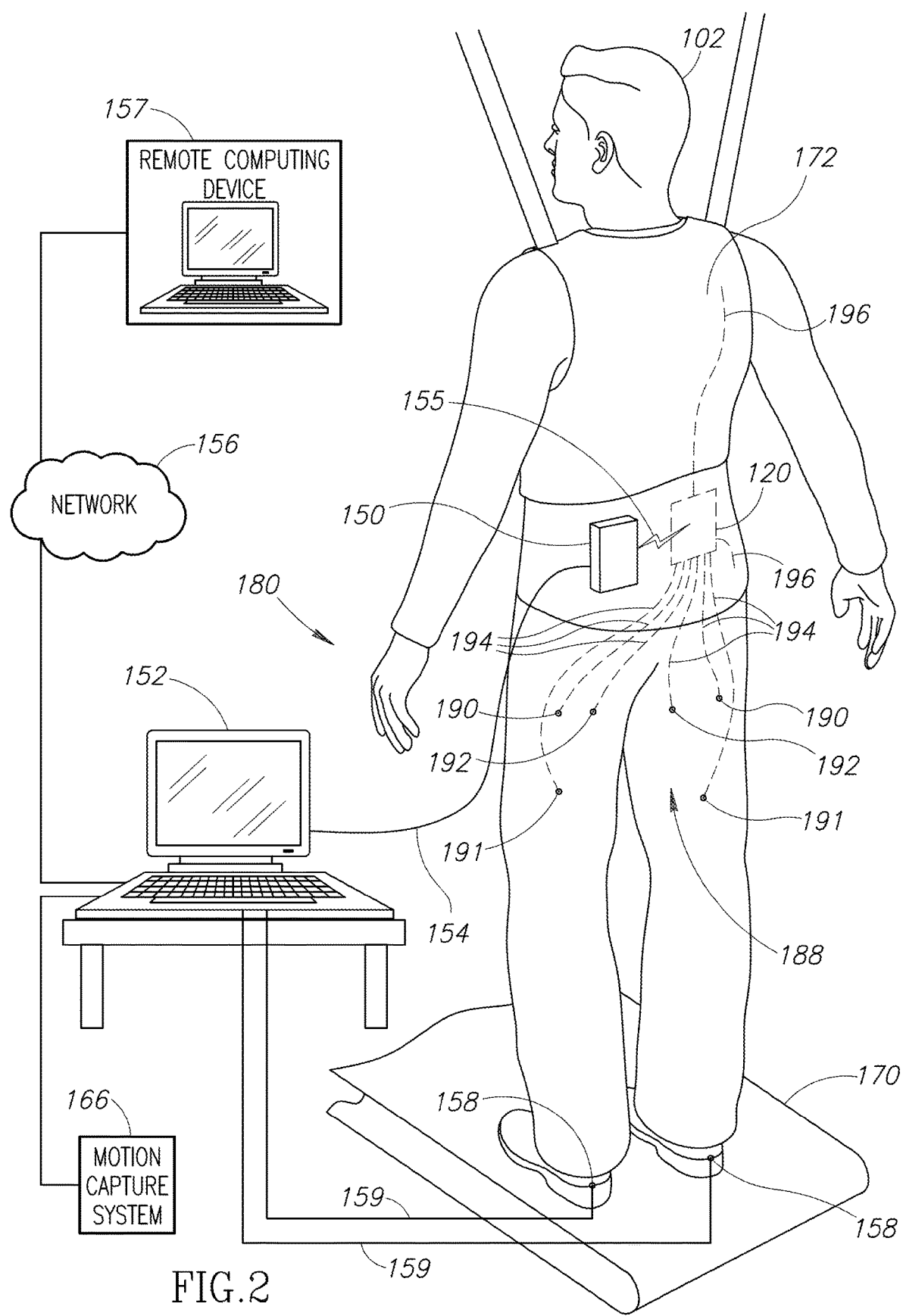
FIG. 2 is an illustration of a system incorporating the implantable assembly of FIG. 1, according to an example embodiment of the present disclosure.

Optionally, the neurostimulator device 120 may be connected to one or more sensors 188 (e.g., Electromyography ("EMG") sensors 190, joint angle (or flex) sensors 191, accelerometers 192, gyroscopic sensors, pressure sensors, flow sensors, load sensors, photonic (light) sensors, and the like) via connections 194 (e.g., wires, wireless connections, and the like). The connections (e.g., the connections 194) and sensors 188 may be implemented using external components and/or implanted components. The sensors 188 may also include a bi-directional brain-computer interface, which enables a patient to subjectively provide feedback. Moreover, the sensors 188 may include an exercise device, such as a treadmill or bicycle that provides feedback regarding activity speed, intensity, etc. In embodiments including the sensors 188, the neurostimulator device 120 may be configured to modify, adjust, or select the complex stimulation pattern based on information received from the sensors 188 via the connections 194. The connections 194 may implemented using wired or wireless connections. Optionally, the neurostimulator device 120 may be connected to reference wires 196. In FIG. 2, one of the reference wires 196 is positioned near the shoulder, the other of the reference wires 196 is positioned in the lower back. However, this is not a requirement.

In embodiments in which the connections 194 are implemented using wires, optionally, the connections 194 may include one or more connectors 136 and 138. In the embodiment illustrated, the connector 136 is used to connect the connections 194 to the sensors 188 and the connector 138 is used to connect the connections 194 to the neurostimulator device 220.

By way of a non-limiting example for use with relatively large patients (e.g., humans), the neurostimulator device 120 may be approximately 20 mm to approximately 25 mm wide, approximately 45 mm to approximately 55 mm long, and approximately 4 mm to approximately 6 mm thick. By way of another non-limiting example for use with relatively small patients (e.g., rats), the neurostimulator device 120 may be approximately 3 mm to approximately 4 mm wide, approximately 20 mm to approximately 30 mm long, and approximately 2 mm to approximately 3 mm thick.

As previously mentioned, placement of the assembly 100 is subcutaneous. The electrodes 142 are positioned on or near a target area (e.g., distal the lesion 112 illustrated in FIG. 1). If the patient 102 (see FIG. 2) has a SCI, the electrode array 140 may be positioned along the spinal cord 110 in a target area that is just distal to a margin of the lesion 112. Thus, if the paralysis was caused by SCI at a first location along the spinal cord 110 (see FIG. 1), the electrodes 142 may be implanted (e.g., epidurally) at a second location below the first location along the spinal cord relative to the patient's brain 108. The electrodes 142 may be placed in or on the spinal cord 110 (see FIG. 1), one or more spinal nerves, one or more nerve roots, ganglia, one or more peripheral nerves, the brain stem, and/or the brain 108 (see FIG. 1).

The complex stimulation pattern may include at least one of tonic stimulation and intermittent stimulation. The stimulation applied may be pulsed. The electrical stimulation may include simultaneous or sequential stimulation of different regions of the spinal cord 110, one or more spinal nerves, one or more nerve roots, one or more peripheral nerves, the brain stem, and/or the brain 108 (see FIG. 1). The complex stimulation pattern applied by the assembly 100 may be below the second stimulation threshold such that the at least one selected spinal circuit is at least partially activatable by the addition of neurological signals (e.g., neurological signals induced by physical training or neurological signals originating from the brain 108) generated by the patient 102 (see FIG. 2). By way of a non-limiting example, neurological signals generated by the patient 102 may be induced by subjecting the patient to physical activity or training (such as stepping on a treadmill 170 while suspended in a harness 172 or other support structure). The neurological signals generated by the patient 102 may be induced in a paralyzed portion of the patient 102. By way of another non-limiting example, the neurological signals generated by the patient 102 may include supraspinal signals (or neurological signals originating from the brain 108).

As mentioned above, the embodiment of the assembly 100 illustrated in FIG. 1 is configured for implantation in the patient 102 (see FIG. 2). However, through application of ordinary skill in the art to the present teachings, embodiments may be constructed for use with other patients, such as other mammals, including rats. The assembly 100 may be configured for chronic implantation and use. For example, the assembly 100 may be used to stimulate one or more nerve roots, ganglia, cell bodies, one or more nerves, the spinal cord 110 (see FIG. 1), a brain stem, a brain, and/or a targeted end organ over time.

The implantable assembly 100 (see FIG. 1) may be used with an external system 180 illustrated in FIG. 2. Turning to FIG. 2, the external system 180 includes an external control unit 150 that may be used program, gather data, and/or charge the neurostimulator device 120 (e.g., via a wireless connection 155). In the embodiment illustrated in FIG. 2, the external control unit 150 is configured to be handheld. Optionally, the external system 180 includes a computing device 152 described in detail below. The external control unit 150 may connected via a connection 154 (e.g., a USB connection, wireless connection, and the like) to an external computing device 152.

The computing device 152 may be connected to a network 156 (e.g., the Internet) and configured to send and receive information across the network to one or more remote computing devices (e.g., a remote computing device 157). In embodiments in which the computing device 152 is implemented with a wireless communication interface, the external control unit 150 may be omitted and the computing device 152 may communicate instructions directly to the neurostimulator device 120 via the wireless connection 155. For example, the computing device 152 may be implemented as a cellular telephone, tablet computing device, and the like having a conventional wireless communication interface. In such embodiments, the computing device 152 may communicate instructions to the neurostimulator device 120 using a wireless communication protocol, such as Bluetooth. Further, the computing device 152 may receive data from the neurostimulator device 120 via the wireless connection 155. Instructions and data may be communicate to and received from the remote computing device 157 over the network 156. Thus, the remote computing device 157 may be used to remotely program the neurostimulator device 120 (via the computing device 152) over the network 156.

One or more external sensors 158 may be connected to the computing device 152 via (wired and/or wireless) connections 159. Further, a motion capture system 166 may be connected to the computing device 152. The external sensors 158 and/or motion capture system 166 may be used to gather data about the patient 102 for analysis by the computing device 152 and/or the neurostimulator device 120. The external sensors 158 may include at least one of the following: foot pressure sensors, a foot force plate, in-shoe sensors, accelerometers, surface EMG sensors, gyroscopic sensors, temperature sensors, flex sensors, and the like. The external sensors 158 may be attached to or positioned near the body of the patient 102. The motion capture system 166 may include any conventional motion capture system (e.g. a video-based motion capture system) and the present teachings are not limited to use with any particular motion capture system.

A. System Embodiment for the Implantable Device

Figure 5:
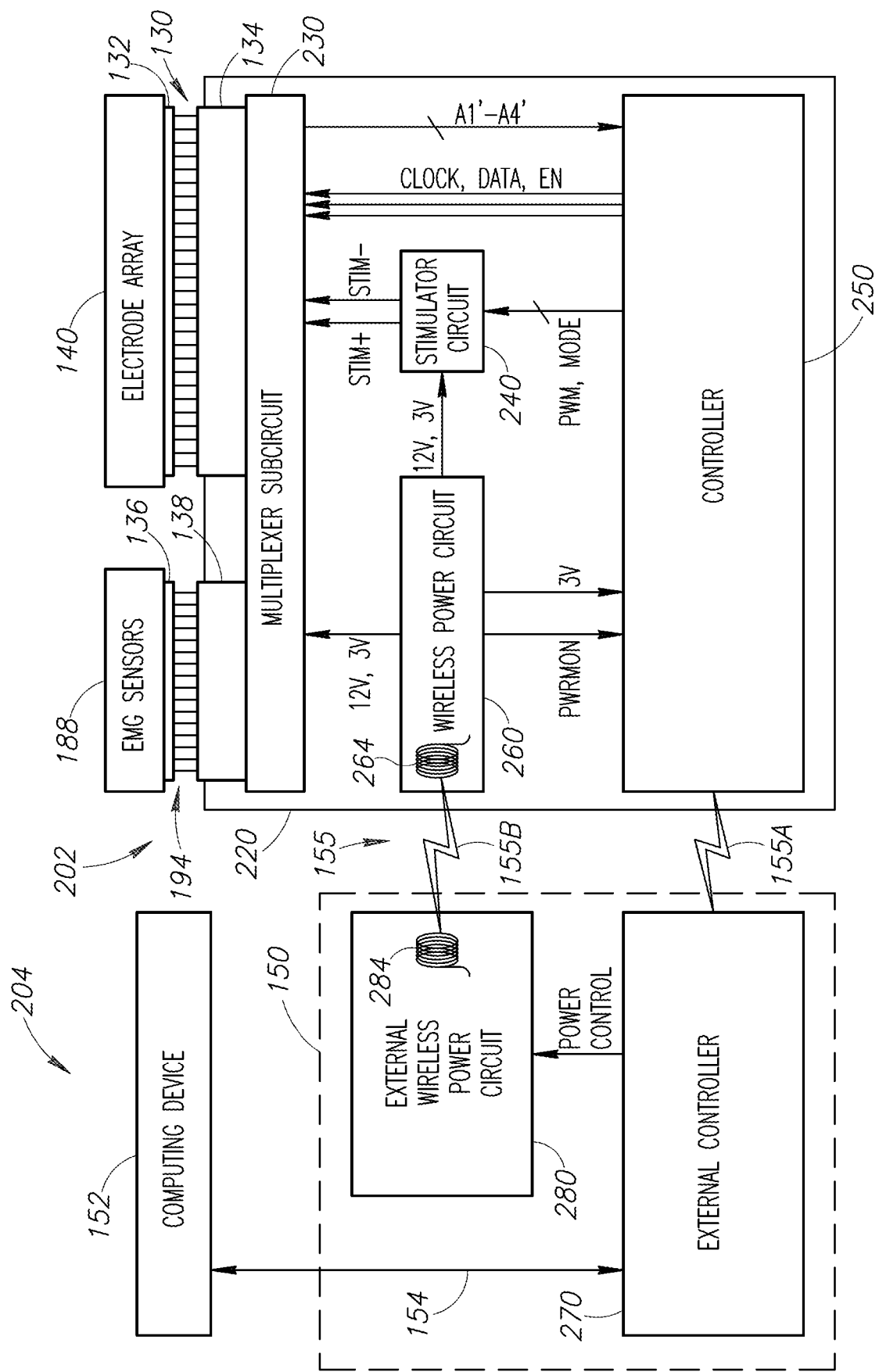
FIG. 5 is a block diagram of a first embodiment of an implantable assembly and an external system.

FIG. 5 is a block diagram of a first embodiment of a system 200. The system 200 includes an implantable assembly 202 substantially similar to the assembly 100 described above, and an external system 204 substantially similar to the external system 180 described above. Therefore, only components of the assembly 202 that differ from those of the assembly 100, and components of the external system 204 that differ from those of the external system 180 will be described in detail. For ease of illustration, like reference numerals have been used to identify like components in FIGS. 1-3 and 5.

The assembly 202 includes a neurostimulator device 220, the one or more leads 130, and the electrode array 140, and the connections 194. The assembly 202 may also include the reference wires 196 (see FIG. 2). By way of a non-limiting example, the assembly 202 may include the two reference wires illustrated in FIG. 2. In the embodiment illustrated, the connections 194 include sixteen wires, each connected to a different one of the sensors 188 (e.g., the EMG sensors 190). However, this is not a requirement and embodiments may be constructed using a different number of connections (e.g., wires), a different number of sensors, and/or different types of sensors without departing from the scope of the present teachings.

In the embodiment illustrated, the electrode array 140 includes the 27 electrodes A1-A9, B1-B9, and C1-C9. However, this is not a requirement and embodiments including different numbers of electrodes (e.g., 16 electrodes, 32 electrodes, 64 electrodes, 256 electrodes, etc.) are within the scope of the present teachings. Particular embodiments include at least 16 electrodes of array 148.

The neurostimulator device 220 is configured to send a stimulating signal (e.g., a "pulse") to any of the electrodes 142 in the electrode array 140. The neurostimulator device 220 is also configured to rapidly switch between different electrodes. Thus, the neurostimulator device 220 can effectively send a predefined pattern of pulses to selected ones of the electrodes 142 in the electrode array 140. In some embodiments, the neurostimulator device 220 is configured to generate a wide variety of waveforms such that virtually any pulsed waveform can be generated. As mentioned above, the electrodes 142 may be arranged in more than four groups, each group including one or more of the electrodes. Further, an electrode may be included in more than one group. In groups including more than one electrode, the electrodes may be stimulated simultaneously.

The wireless connection 155 may be two components, a communication connection 155A and a power transfer connection 155B.

Depending upon the implementation details, the neurostimulator device 220 may be configured to deliver stimulation having the following properties:

1. A maximum voltage (e.g., a constant voltage mode) of about ±12 V;
2. A maximum stimulating current (e.g., a constant current mode) of about ±5 mA;
3. A maximum stimulation frequency of about 100 Hz;
4. A minimum pulse width of about 0.1 ms having a frequency as high as about 50 Hz;
5. A maximum recording bandwidth of about 60 kHz (−3 dB);
6. Digital to Analog converter ("DAC") resolution of about 7 bits to about 14 bits; Configuration switch time of about 3 µs;
7. Ability to configure stimulation and deliver stimulation (e.g., a pulse) about 100 times per millisecond;
9. Simultaneously addressable electrodes (e.g., any pair of the electrodes 142 may be addressed with multiple groups (e.g., more than four groups) of electrodes being addressable (e.g., stimulated or recorded from) simultaneously);

10. An ability to stimulate or record from one or more electrodes in the electrode array;
11. Any of the electrodes 142, if not used for applying stimulation, can be selected as a differential pair of electrodes and used for recording;
12. A wireless data transfer rate of about 250 kBps (ISM band 915 MHz) across the communication connection 155A to send and/or receive data; and
13. A maximum power consumption of about 100 mW.

In the embodiment illustrated in FIG. 5, the neurostimulator device 220 includes a multiplexer sub-circuit 230, a stimulator circuit 240, a controller 250 (connected to a controller circuit 252 illustrated in FIG. 8), and an optional wireless power circuit 260. The controller 250 sends control signals Clock, Data, and EN to the multiplexer sub-circuit 230, and receives data A1'-A4' from the multiplexer sub-circuit 230. The stimulator circuit 240 provides a first stimulation signal STIM+ and a second stimulation signal STIM− to the multiplexer sub-circuit 230. The controller 250 sends control signals PWM and MODE to the stimulator circuit 240. The control signal MODE sent by the controller 250 to the stimulator circuit 240 instructs the stimulator circuit 240 to operate in either constant voltage mode or constant current mode. The control signal PWM sent by the controller 250 to the stimulator circuit 240 uses pulse-width modulation to control power sent by the stimulator circuit 240 to the multiplexer sub-circuit 230 as the first and second stimulation signals STIM+ and STIM−. Thus, the control signal PWM configures at least a portion of the complex stimulation pattern. However, the multiplexer sub-circuit 230 determines which of the electrodes 142 and/or connections 194 receives the stimulation. Therefore, the multiplexer sub-circuit 230 configures at least a portion of the complex stimulation pattern. However, both the stimulator circuit 240 and the multiplexer sub-circuit 230 configure the complex stimulation pattern based on instructions received from the controller 250.

The controller 250 is connected wirelessly to the external programming unit 150 via the communication connection 155A. The communication connection 155A may be configured to provide bi-directional wireless communication over which the controller 250 may receive system control commands and data from the external programming unit 150, as well as transmit status information and data to the external programming unit 150. In some embodiments, the communication connection 155A may include one or more analog communication channels, one or more digital communication channels, or a combination thereof.

The controller 250 receives power (e.g., 3V) from the wireless power circuit 260 and a power monitoring signal PWRMON from the wireless power circuit 260. The wireless power circuit 260 provides power (e.g., 12V and 3V) to the multiplexer sub-circuit 230. The wireless power circuit 260 also provides power (e.g., 12V and 3V) to the stimulator circuit 240. The wireless power circuit 260 receives power wirelessly from the external programming unit 150 via the power transfer connection 155B.

Figure 6A:
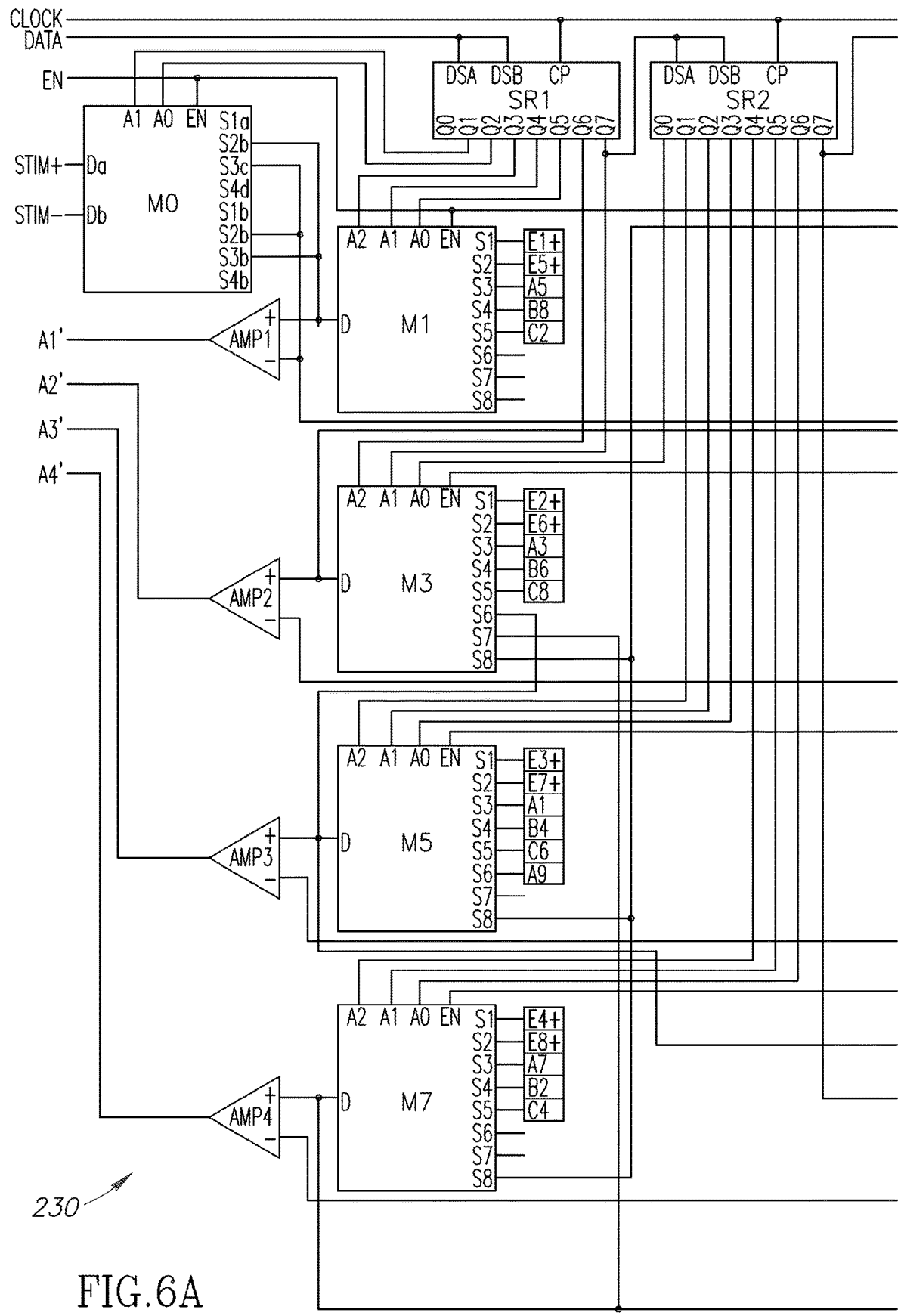
FIG. 6A is a leftmost portion of a circuit diagram of a multiplexer sub-circuit of a neurostimulator device of the implantable assembly of FIG. 5, according to an example embodiment of the present disclosure.
Figure 6B:
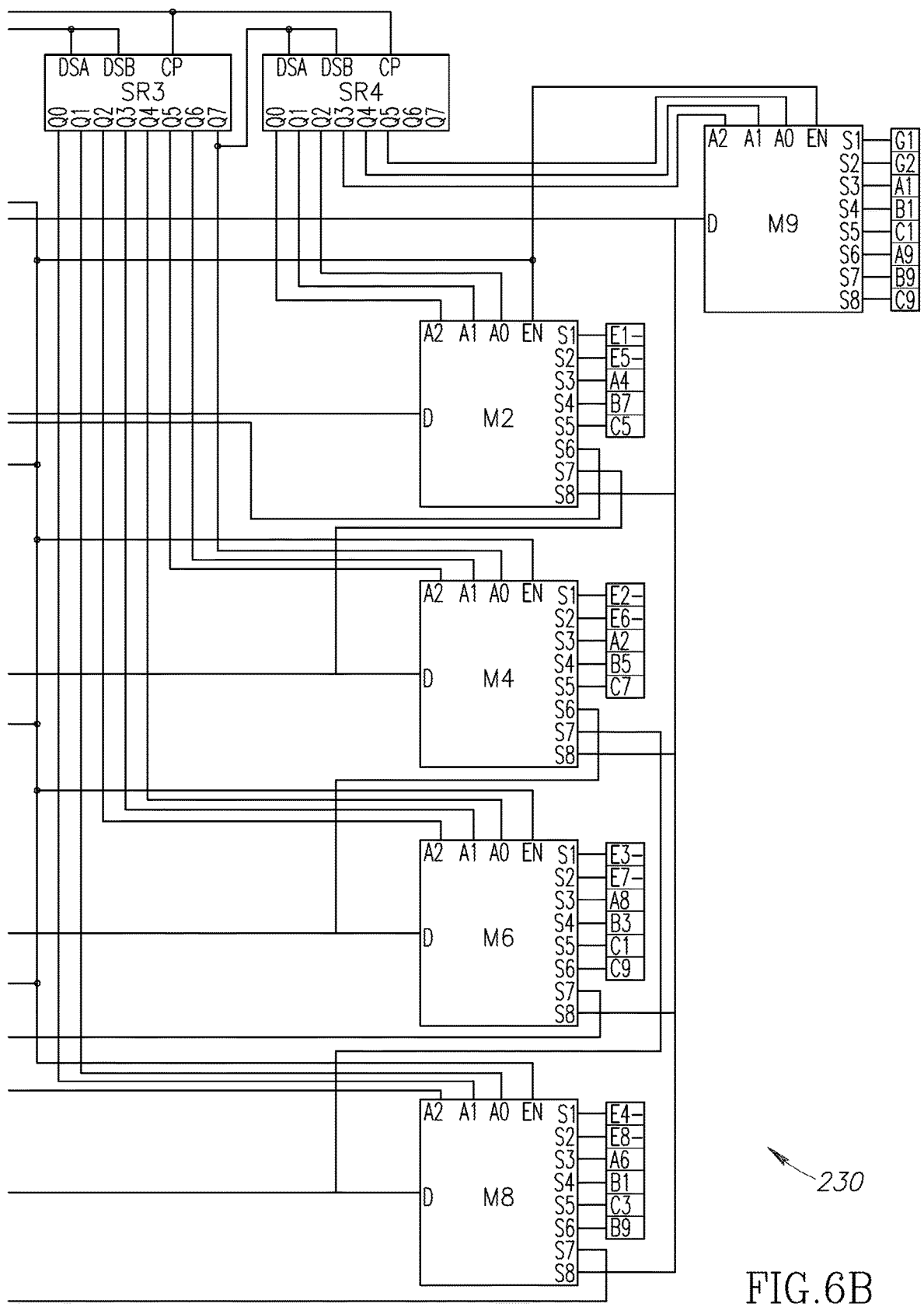
FIG. 6B is a rightmost portion of the circuit diagram of the multiplexer sub-circuit of the neurostimulator device of the implantable assembly of FIG. 5, according to an example embodiment of the present disclosure.

FIGS. 6A and 6B are a circuit diagram of an exemplary implementation of the multiplexer sub-circuit 230. FIG. 6A is a leftmost portion of the circuit diagram of the multiplexer sub-circuit 230, and FIG. 6B is a rightmost portion of the circuit diagram of the multiplexer sub-circuit 230. The circuit diagram of FIGS. 6A and 6B includes amplifiers AMP1-AMP4, shift registers SR1-SR4 (e.g., implemented using NXP Semiconductors 74HC164), and analog multiplexer chips M0-M9.

The amplifiers AMP1-AMP4 output the data A1'-A4', respectively. The amplifiers AMP1-AMP4 (e.g., Analog Devices AD8224) may be implemented as differential amplifiers with a gain set to 200. However, as is apparent to those of ordinary skill in the art, other gain values may be used. Further, the gains of the amplifiers AMP1-AMP4 may be readily changed by modifications to the components known to those of ordinary skill in the art.

The multiplexer sub-circuit 230 routes the first and second stimulation signals Stim+ and Stim− to the selected ones of the electrodes 142 and/or connections 194. The multiplexer sub-circuit 230 also routes signals received from selected ones of the electrodes 142 and/or connections 194 to the amplifiers AMP1-AMP4. Thus, the multiplexer sub-circuit 230 is configured to route signals between the stimulator circuit 240, the amplifiers AMP1-AMP4, the electrodes 142, and the connections 194.

The controller 250 sends a 30-bit serial data stream through the control signals Clock and Data to the multiplexer sub-circuit 230, which is fed into the shift registers SR1-SR4. The shift registers SR1-SR4 in turn control the analog multiplexer chips M0-M9, which are enabled by the control signal EN.

The multiplexer chip M0 has inputs "Da" and "Db" for receiving the first and second stimulation signals STIM+ and STIM−, respectively, from the controller 250. The multiplexer chip M0 is used to disconnect one or more of the electrodes 142 and/or one or more of the sensors 188 (e.g., the EMG sensors 190) during recording of signals detected by the disconnect component(s). The multiplexer chip M0 is also used to select a polarity (or tristate) for each of the electrodes 142 when stimulation is applied. The multiplexer chip M0 may be implemented as a 2×(4:1) multiplexer (e.g., Analog Devices ADG1209).

The multiplexer chips M1-M9 are interconnected to connect almost any pair of the electrodes 142 or connections 194 to the amplifier AMP1 and the inputs "Da" and "Db" (which receive the first and second stimulation signals STIM+ and STIM−, respectively) of multiplexer chip M0. The multiplexer chips M1-M9 may each be implemented using an 8:1 multiplexer (e.g., Analog Devices ADG1208).

With respect to the multiplexer chips M1-M9, a label in each rectangular tag in the circuit diagram identifies a connection to one of the electrodes 142 or connections 194. Each label in a rectangular tag starting with the letter "E" identifies a connection to one of the connections 194 connected to one of the sensors 188 (e.g., one of the EMG sensors 190). For example, the label "E1+" adjacent multiplexer chip M1 identifies a connection to a first wire, and the label "E1" adjacent multiplexer chip M2 identifies a connection to a second wire. Together, the labels "E1+" and "E1−" identify connections a first pair of the connections 194.

The labels "G1" and "G2" adjacent multiplexer chip M9 identify connections to the reference wires 196 (see FIG. 2).

Each label in a rectangular tag starting with a letter other than the letter "E" or the letter "G" identifies a connection to one of the electrodes 142. For example, the label "A3" refers to a connection to the electrode A3 (see FIG. 3) in column A and row 3 (where column A is leftmost, column B is in the middle, column C is rightmost, row 1 is rostral, and row 9 is caudal). Optionally, some key electrodes may have more than one connection to the multiplexer sub-circuit 230. For example, the electrodes A1, B1, C1, A9, B9, and C9 are each identified by more than one label.

The multiplexer sub-circuit 230 is designed to operate in at least four modes. In a first mode, the multiplexer sub-circuit 230 is configured to select an individual electrode to which to apply a monopolar stimulating pulse. In a second mode, the multiplexer sub-circuit 230 is configured to select a pair of the electrodes 142 to stimulate in a bipolar fashion. In a third mode, the multiplexer sub-circuit 230 is configured to select a single electrode from which to record, with the recorded waveform referenced to a ground signal. In a fourth mode, the multiplexer sub-circuit 230 is configured to select a pair of the electrodes 142 from which to record in a differential fashion.

As mentioned above, the neurostimulator device 220 is configured to provide selective stimulation to any of the electrodes 142. The multiplexer sub-circuit 230 is configured to route stimulation between almost any pair of the electrodes 142 or the connections 194. For example, the electrode A1 may be the anode and the electrode B6 the cathode.

The multiplexer sub-circuit 230 is configured route signals received from the connections 194 to the amplifiers AMP1-AMP4 and to the controller 250 (in data A1'-A4') for recording thereby. Similarly, the multiplexer sub-circuit 230 is configured route signals received from the electrodes 142 to the amplifiers AMP1-AMP4 and to the controller 250 (in data A1'-A4') for recording thereby. By way of a non-limiting example, the multiplexer sub-circuit 230 may be configured route signals received from four electrodes positioned in the same column (e.g. electrodes A1, A3, A5, and A7) and signals received from a fifth electrode (e.g., electrode A9) positioned in the same column to the controller 250 (in data A1'-A4' output by the amplifiers AMP1-AMP4) so that a differential signal received from the first four relative to the fifth may be recorded by the controller 250 for each pair of electrodes (e.g., a first pair including electrodes A1 and A9, a second pair including electrodes A3 and A9, a third pair including electrodes A5 and A9, and a fourth pair including electrodes A7 and A9).

As mentioned above, the multiplexer sub-circuit 230 receives power (e.g., 12V and 3V) from the wireless power circuit 260. For ease of illustration, power lines providing this power to the multiplexer sub-circuit 230 have been omitted. The power lines may be implemented using one line having a voltage of about +12V, one line having a voltage of about +2V to about +6V (e.g., +3V), and one ground line.

The multiplexer sub-circuit 230 may be configured to change configurations in less than one microsecond in embodiments in which the control signals Clock and Data are fast enough. This allows the first and second stimulation signals Stim+ and Stim− (received from the stimulator circuit 240) to be delivered in short pulses to selected ones of the electrodes 142 in about one millisecond and also allows the amplifiers AMP1-AMP4 to rapidly switch input signals so the controller 250 may effectively record from 8 or 16 signals (instead of only four) within as little as about 20 microseconds. In some embodiments, the controller 250 may effectively record from 8 or 16 signals (instead of only four) within as little as 5 microseconds.

Figure 7:
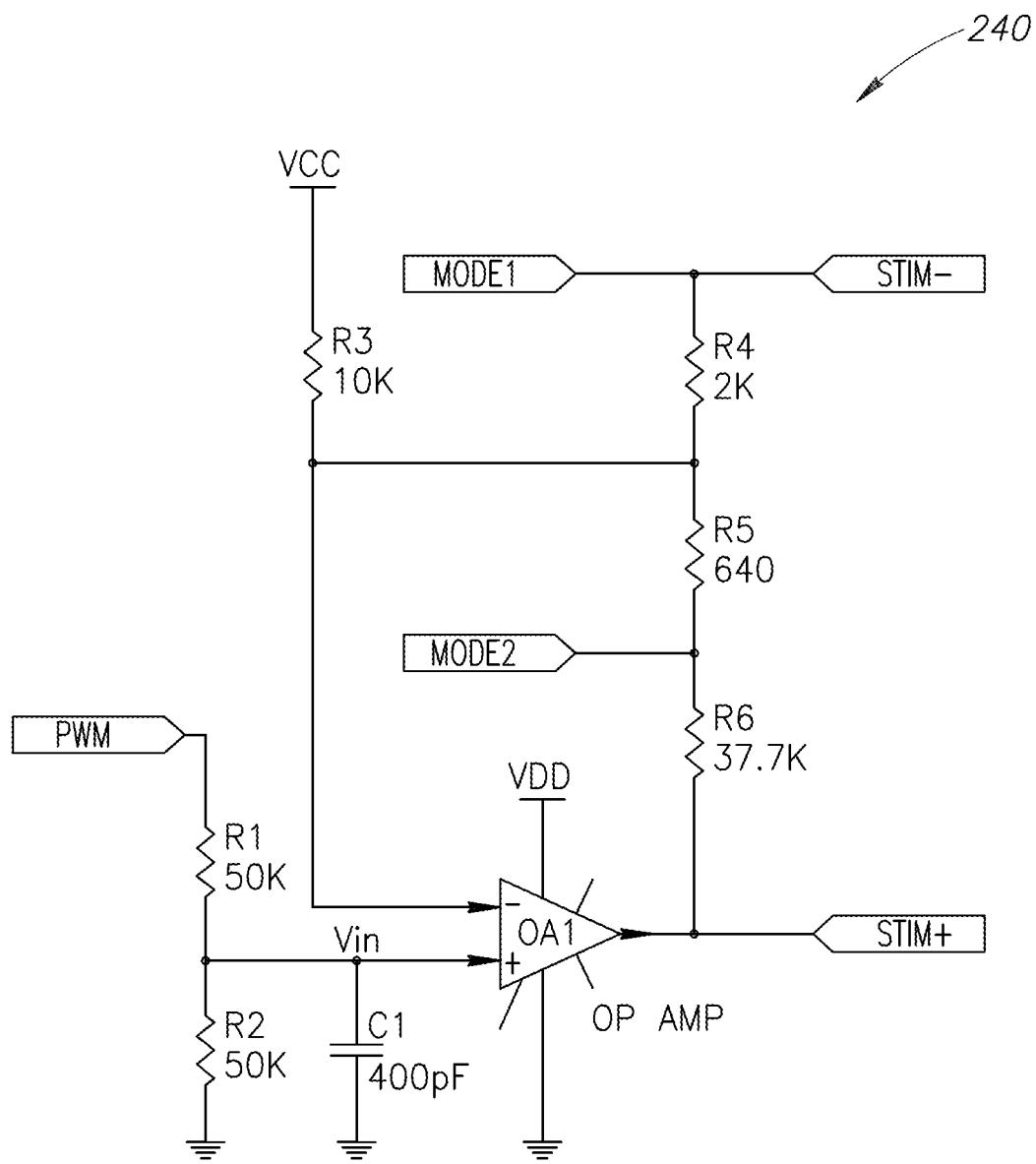
FIG. 7 is a circuit diagram of a stimulator circuit of the neurostimulator device of the implantable assembly of FIG. 5, according to an example embodiment of the present disclosure.

FIG. 7 illustrates a circuit diagram of an exemplary implementation of the stimulator circuit 240. As mentioned above, the stimulator circuit 240 is configured to selectively operate in two modes: constant voltage mode and constant current mode. In FIG. 7, labels "Mode1" and "Mode2" identify connections to pins "P1_0" and "P1_1," respectively, of the controller 250 (see FIG. 8). When pin "P1_0" (connected to the connection labeled "Mode1") is set to ground and pin "P1_1" (connected to the connection labeled "Mode2") is high impedance, the stimulator circuit 240 is in constant voltage mode. When pin "P1_1" (connected to the connection labeled "Mode2") is set to ground and pin "P1_0" (connected to the connection labeled "Mode1") is high impedance, the stimulator circuit 240 is in constant current mode.

Figure 8:
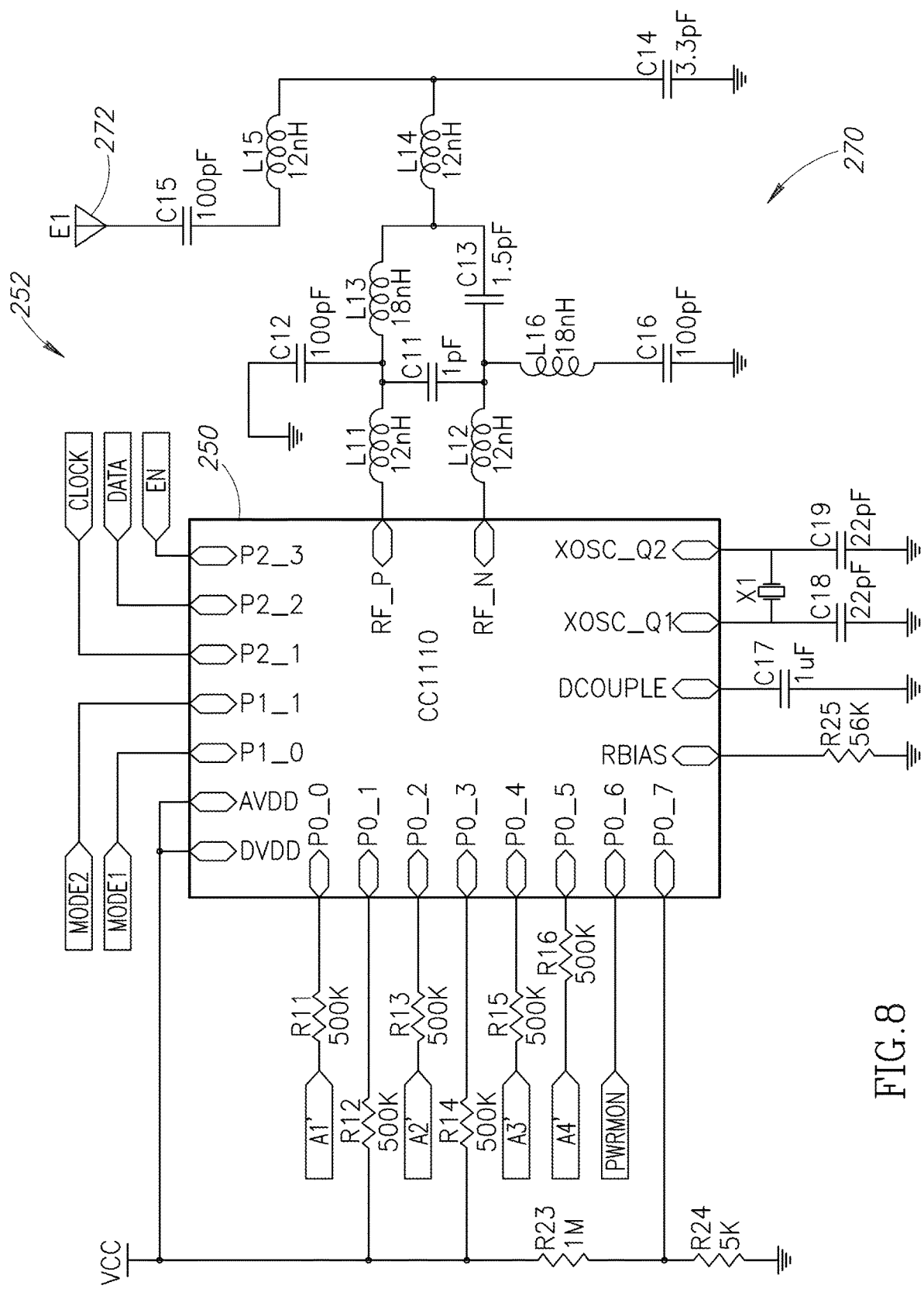
FIG. 8 is a circuit diagram of a controller circuit of the neurostimulator device of the implantable assembly of FIG. 5, according to an example embodiment of the present disclosure.

FIG. 8 illustrates a circuit diagram of an exemplary implementation of a controller circuit 252 that includes the controller 250 and its surrounding circuitry. The controller 250 controls the multiplexer sub-circuit 230, records amplified signals received (in the data A1'-A4') from the multiplexer sub-circuit 230, and monitors wireless power (using the power monitoring signal PWRMON received from the wireless power circuit 260). The controller 250 also communicates with an external controller 270. In the embodiment illustrated, the controller 250 has been implemented using a Texas Instruments CC1110. However, through application of ordinary skill to the present teachings, embodiments may be constructed in which the controller 250 is implemented using a different microcontroller, a microprocessor, a Field Programmable Gate Array ("FPGA"), a Digital Signal Processing ("DSP") engine, a combination thereof, and the like.

It may be desirable to record signals (e.g., Motor Evoked Potentials ("MEPs")) received from the electrode array 140. For example, recorded MEPs can help assess the health and state of the spinal cord 110, and may be used to monitor the rate and type of recovery of spinal cord function under long-term epidural stimulation. Therefore, in some embodiments, the controller circuit 252 is configured to record voltages and currents received from the electrode array 140 when it is not stimulated. In such embodiments, the controller circuit 252 is also configured to transmit the recorded data over the communication connection 155A (e.g., in "real time") to the external programming unit 150. In the embodiment illustrated, the controller circuit 252 includes an antenna 272 configured to communicate with the external controller 270. The controller circuit 252 may be configured to coordinate stimulating (signal sending) and reading (signal receiving) cycles with respect to the electrode array 140.

With respect to controlling the state of the implanted neurostimulator device 220, the controller circuit 252 may be configured to measure (and/or control) the exact timing of the onset of stimulation. The controller circuit 252 may be configured to reset or stop stimulation at a desired time. The controller circuit 252 may be configured to transition smoothly between successive stimulation (e.g., pulses) and successive stimulation patterns.

With respect to patient monitoring and safety, the controller circuit 252 may be configured to monitor electrode impedance, and impedance at the electrode/tissue interface. Of particular concern is impedance at relatively low frequencies (e.g., 10-1000 Hz). The controller circuit 252 may be configured to limit current and voltage. Further, the controller circuit 252 may be configured to trigger an alarm (or send an alarm message to the computing device 152) when voltage or current limits are exceeded. Optionally, the neurostimulator device 220 may shut down or power down if an unsafe condition is detected.

The external controller 270 may be used to program the controller 250. The external controller 270 may be a component of the external control unit 150 (see FIG. 2). The external controller 270 may be implemented using a Texas Instruments CC1111. The external controller 270 may relay information to and from the computing device 152 through the connection 154 (e.g., a USB connection, and/or a wireless connection).

The computing device 152 may be configured to control data streams to be sent to the neurostimulator device 220. The computing device 152 may interpret data streams received from the neurostimulator device 220. In some implementations, the computing device 152 is configured to provide a graphical user interface for communicating with the neurostimulator device 220. The user interface may be used to program the neurostimulator device 220 to deliver a particular stimulation. For example, the user interface may be used to queue up a particular sequence of stimuli. Alternatively, the computing device 152 may execute a method (e.g., a machine learning method and/or dueling bandits algorithm described below) configured to determine or select stimulation parameters. In some embodiments, the user interface may be used to configure the method performed by the computing device 152. The user interface may be used to transfer information recorded by the neurostimulator device 220 to the computing device 152 for storage and/or analysis thereby. The user interface may be used to display information indicating an internal system state (such the current selection of stimulation parameters values) and/or mode of operation (e.g., constant voltage mode, constant current mode, and the like). Additionally or alternatively, the user interface for the computing device 152 may include a bi-directional brain-computer interface system.

Figure 9:
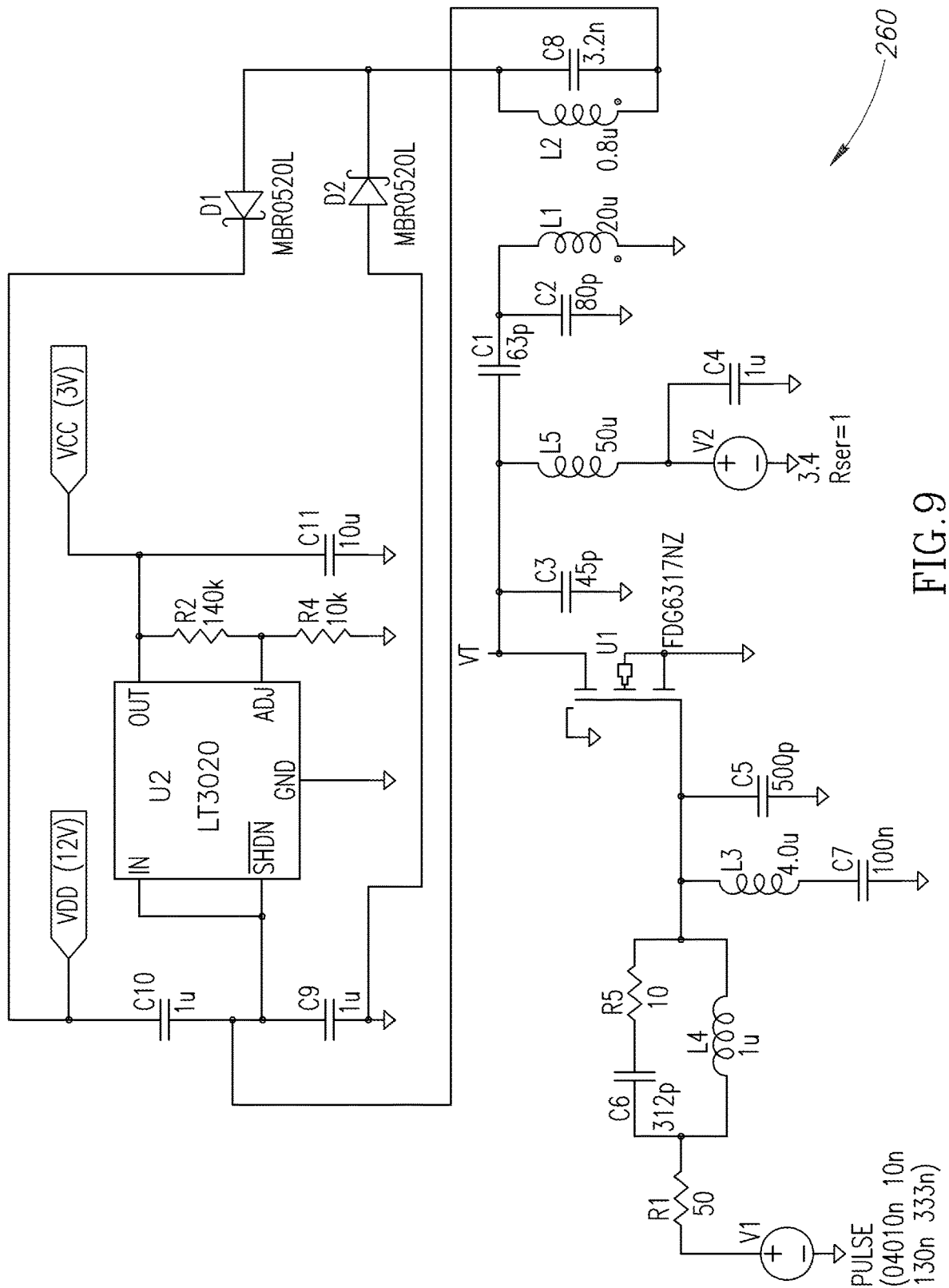
FIG. 9 is a circuit diagram of a wireless power circuit of the neurostimulator device of the implantable assembly of FIG. 5, according to an example embodiment of the present disclosure.

FIG. 9 illustrates a circuit diagram of an exemplary implementation of the optional wireless power circuit 260. The wireless power circuit 260 is configured to receive power wirelessly from an external wireless power circuit 280. The wireless power circuit 260 may supply both about 3V DC (output VCC) and about 12V DC (output VDD). As mentioned above, the output VCC is connected to the multiplexer sub-circuit 230, the stimulator circuit 240, and the controller 250, and the output VDD is connected to the multiplexer sub-circuit 230 and the stimulator circuit 240.

The external wireless power circuit 280 may be a component of the external control unit 150 (see FIG. 2). The external wireless power circuit 280 may be implemented using a Class E amplifier and configured to provide variable output. In the embodiment illustrated, the external wireless power circuit 280 provides power to the wireless power circuit 260 via inductive coupling over the power transfer connection 155B. The wireless power circuit 260 may include a radio frequency ("RF") charging coil 264 and the external wireless power circuit 280 includes an RF charging coil 284 configured to transfer power (e.g., inductively) to the RF charging coil 264. Optionally, communication channels may be multiplexed on the wireless transmission.

The wireless power circuit 260 may be connected to one or more rechargeable batteries (not shown) that are chargeable using power received from the external wireless power circuit 280. The batteries may be implemented using rechargeable multi-cell Lithium Ion Polymer batteries.

B. Second System Embodiment for the Implantable Device

Figure 10:
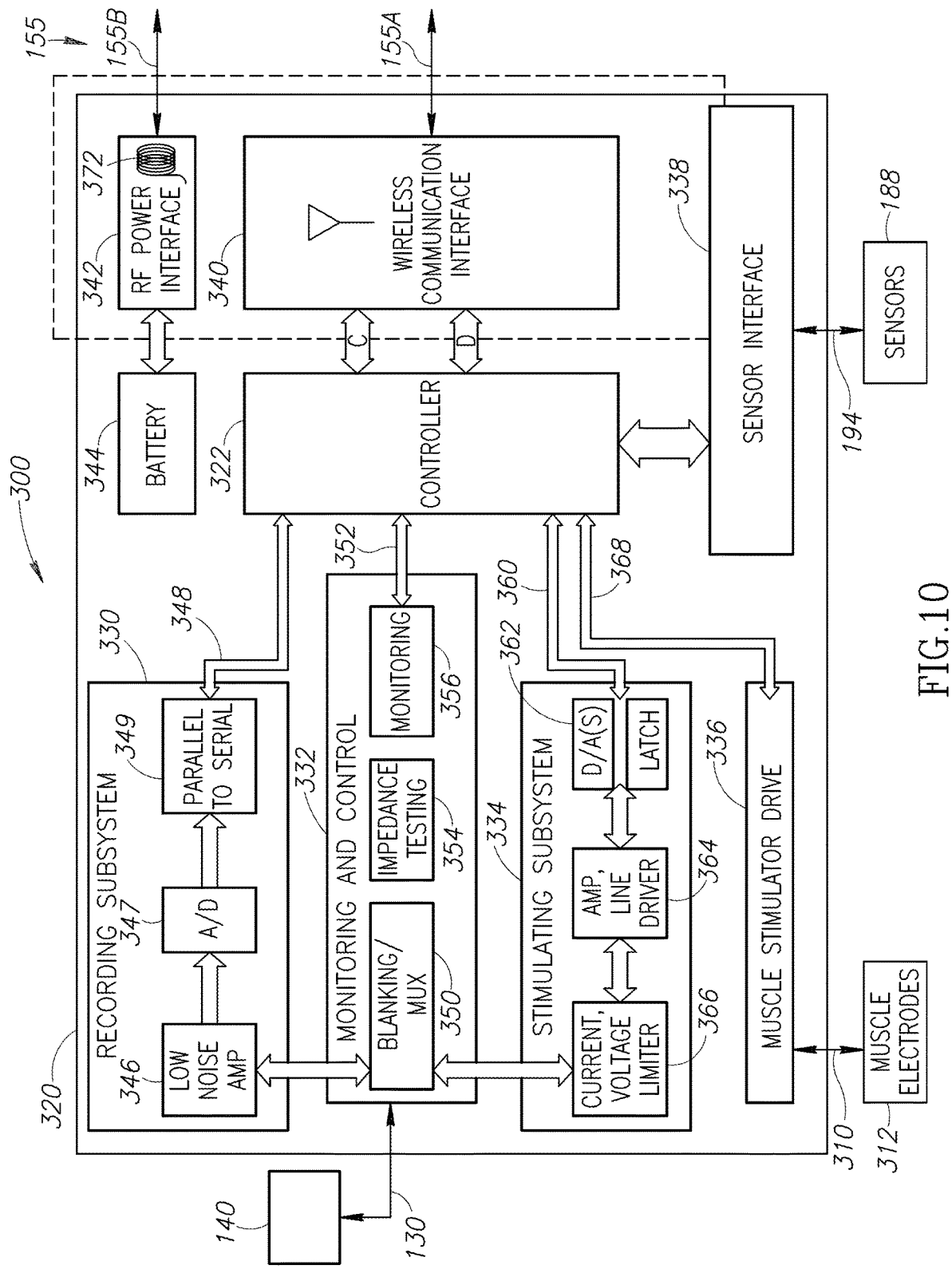
FIG. 10 is a block diagram of a second embodiment of an implantable assembly.

FIG. 10 illustrates a block diagram of an implantable assembly 300. For ease of illustration, like reference numerals have been used to identify like components in FIGS. 1-3, 5, and 10. The assembly 300 may be configured to communicate with the external controller 270 via the communication connection 155A. Optionally, the assembly 300 may receive power wirelessly from the external wireless power circuit 280 via inductive coupling over the power transfer connection 155B.

In addition to providing complex stimulation patterns to body tissue (e.g., neurological tissue), the assembly 300 is configured to also provide electrical stimulation directly to muscles (not shown) that will cause the muscle to move (e.g., contract) to thereby augment the improved neurological function provided by the complex stimulation patterns alone. The assembly 300 is configured to provide one or more complex stimulation patterns to one or more individually addressable electrodes for purposes of providing improved neurological function (e.g., improved mobility recovery after SCI).

The assembly 300 includes a neurostimulator device 320, the one or more leads 130, and the electrode array 140, the connections 194 (connected to the sensors 188), and connections 310 (e.g., wires, wireless connections, and the like) to (implanted and/or external) muscle electrodes 312. The assembly 300 may also include the reference wires 196 (see FIG. 2). By way of a non-limiting example, the assembly 300 may include the two reference wires illustrated in FIG. 2. In the embodiment illustrated, the connections 194 include sixteen wires, each connected to a different one of the sensors 188 (e.g., the EMG sensors 190). However, this is not a requirement and embodiments may be constructed using a different number of wires, a different number of EMG sensors, and/or different types of sensors without departing from the scope of the present teachings.

The neurostimulator device 320 includes a controller 322, a recording subsystem 330, a monitor and control subsystem 332, a stimulating subsystem 334, a muscle stimulator drive 336, a sensor interface 338, a wireless communication interface 340, an RF power interface 342, and at least one power source 344 (e.g., a rechargeable battery). In the embodiment illustrated, the controller 322 has been implemented using a microcontroller (e.g., a Texas Instruments CC1110). However, through application of ordinary skill to the present teachings, embodiments may be constructed in which the controller 250 is implemented using a microprocessor, FPGA, DSP engine, a combination thereof, and the like.

The recording subsystem 330 is configured to record electrical signals received from one or more of the electrodes 142 in the electrode array 140. The electrodes used to record may be the same electrodes used to provide the complex stimulation pattern, or different electrodes specialized for recording. The recording subsystem 330 may be connected (directly or otherwise) to one or more of the leads 130. In the embodiment illustrated, the recording subsystem 330 is connected to the leads 130 via the monitor and control subsystem 332. The recording subsystem 330 may also include one or more amplifiers 346. In the embodiment illustrated, the amplifiers 346 are implemented as low noise amplifiers ("LNAs") with programmable gain.

The monitor and control subsystem 332 illustrated includes a blanking circuit 350 that is connected directly to the leads 130. The blanking circuit 350 is configured to disconnect the recording subsystem 330 (which is connected thereto) from the leads 130 when the complex stimulation pattern is applied to the electrodes 142 to avoid damaging the amplifiers 346. Bidirectional control and status lines (not shown) extending between the blanking circuit 350 and the controller 340 control the behavior of the blanking circuit 350.

The monitor and control subsystem 332 monitors the overall activity of the neurostimulator device 320, as well as the functionality (e.g., operability) of the electrode array 140. The monitor and control subsystem 332 is connected to the CPU by bidirectional digital and analog signal and control lines 352. In some embodiments, the monitor and control subsystem 332 includes a circuit 354 configured to monitor electrode impedance. Optionally, a multiplexer (not shown) may be connected to the leads 130, allowing the monitor and control subsystem 332 to selectively interrogate the signal received from each electrode. The output of the multiplexer (not shown) is connected to an A/D circuit (not shown), so that a signal received from a selected one of the electrodes 142 can be digitized, and transmitted to the controller 322 to assess the functionality of the stimulating circuitry. The monitor and control subsystem 332 may include circuitry 356 configured to assess the functionality (e.g., operability) of the power source 344.

The amplifiers 346 receive signals from the leads 130 when the blanking circuit 350 is in the off state. In some embodiments, a different one of the amplifiers 346 is connected to each different one of the leads 130. In other embodiments, the blanking circuit 350 includes or connected to a multiplexing circuit having an input is connected to the leads 130 and the output of the blanking system 350. In such embodiments, the multiplexing circuit routes an electrode signal (selected by the controller 322) to a single one of the amplifiers 346. The amplifiers 346 are connected to the controller 322 via bidirectional control and status lines (not shown) that allow the controller 322 to control the gain and behavior of the amplifiers 346.

The recording subsystem 330 includes an analog-to-digital ("A/D") circuit 347 that digitizes the output(s) received from the amplifiers 346. In some embodiments, a separate A/D circuit is dedicated to the output of each amplifiers 346. In other embodiments, a multiplexing circuit (not shown) routes the output of a selected one of the amplifiers 346 to a single A/D circuit. The output of the A/D circuit 347 is connected via a serial or parallel digital bus 348 to the controller 322. In the embodiment illustrated, the recording subsystem 330 includes a parallel to serial circuit 349 that serializes the output received from the A/D circuit 347 for transmission on the bus 348. Control and status lines (not shown) connect the A/D circuit 347 to the controller 322, allowing the controller 322 to control the timing and behavior of the A/D circuit 347.

The stimulating subsystem 334 delivers complex stimulation patterns over channels. Each channel corresponds to one of the electrodes 142. Stimulation delivered over a channel is applied to the corresponding one of the electrodes 142. Similarly, stimulation received from one of the electrodes 142 may be received over the corresponding channel. However, in some embodiments, two or more electrodes may be physically connected to the same channel so their operation is governed by a single channel.

The stimulating subsystem 334 is configured to generate complex stimulation patterns, which as explained above include complex waveforms (either in voltage or current mode), and deliver the stimulation on each of one or more of the channels. The stimulating subsystem 334 is connected to the controller 322 by multiple bidirectional lines 360 over which the stimulating subsystem 334 receives commands and stimulating waveform information. The stimulating subsystem 334 may transmit circuit status information to the controller 322 over the lines 360. Each output is connected to one of the leads 130, thereby stimulating a single one of the electrodes 142 in the electrode array 140.

In the embodiment illustrated, the stimulating subsystem 334 includes a digital-to-analog amplifier 362 that receives stimulating waveform shape information from the controller 322. The amplifier 362 turn drives (voltage or current) amplifiers 364. The outputs of the amplifiers 364 are monitored and potentially limited by over-voltage or over-current protection circuitry 366).

The muscle stimulator drive 336 is configured to drive one or more of the muscle electrodes 312. Alternatively, the muscle stimulator drive 336 may provide an interface to a separate drive system (not shown). The muscle stimulator drive 336 is connected by bidirectional control lines 368 to the controller 322 to control the operation of the muscle stimulator drive 336.

The sensor interface 338 interfaces with one or more of the sensors 188 (the EMG sensors 190, joint angle sensors 191, accelerometers 192, and the like). Depending upon the implementation details, the sensor interface 338 may include digital signal inputs (not shown), low noise amplifiers (not shown) configured for analog signal line inputs, and analog inputs (not shown) connected to A/D circuits (not shown).

The controller 322 may be connected wirelessly to the external programming unit 150 via the communication connection 155A. The communication connection 155A may be configured to provide bi-directional wireless communication over which the controller 322 may receive system control commands and data from the external programming unit 150, as well as transmit status information and data to the external programming unit 150. In some embodiments, the communication connection 155A may include one or more analog communication channels, one or more digital communication channels, or a combination thereof.

The RF power interface 342 may receive power wirelessly from the external programming unit 150 via the power transfer connection 155B. The RF power interface 342 may include a radio frequency ("RF") charging coil 372. In such embodiments, the RF charging coil 284 of the external wireless power circuit 280 may be configured to transfer power (e.g., inductively) to the RF charging coil 272. Optionally, communication channels may be multiplexed on the wireless transmission. The power source 344 may be implemented using one or more rechargeable multi-cell Lithium Ion Polymer batteries.

C. Third System Embodiment for the Implantable Device

Figure 11:
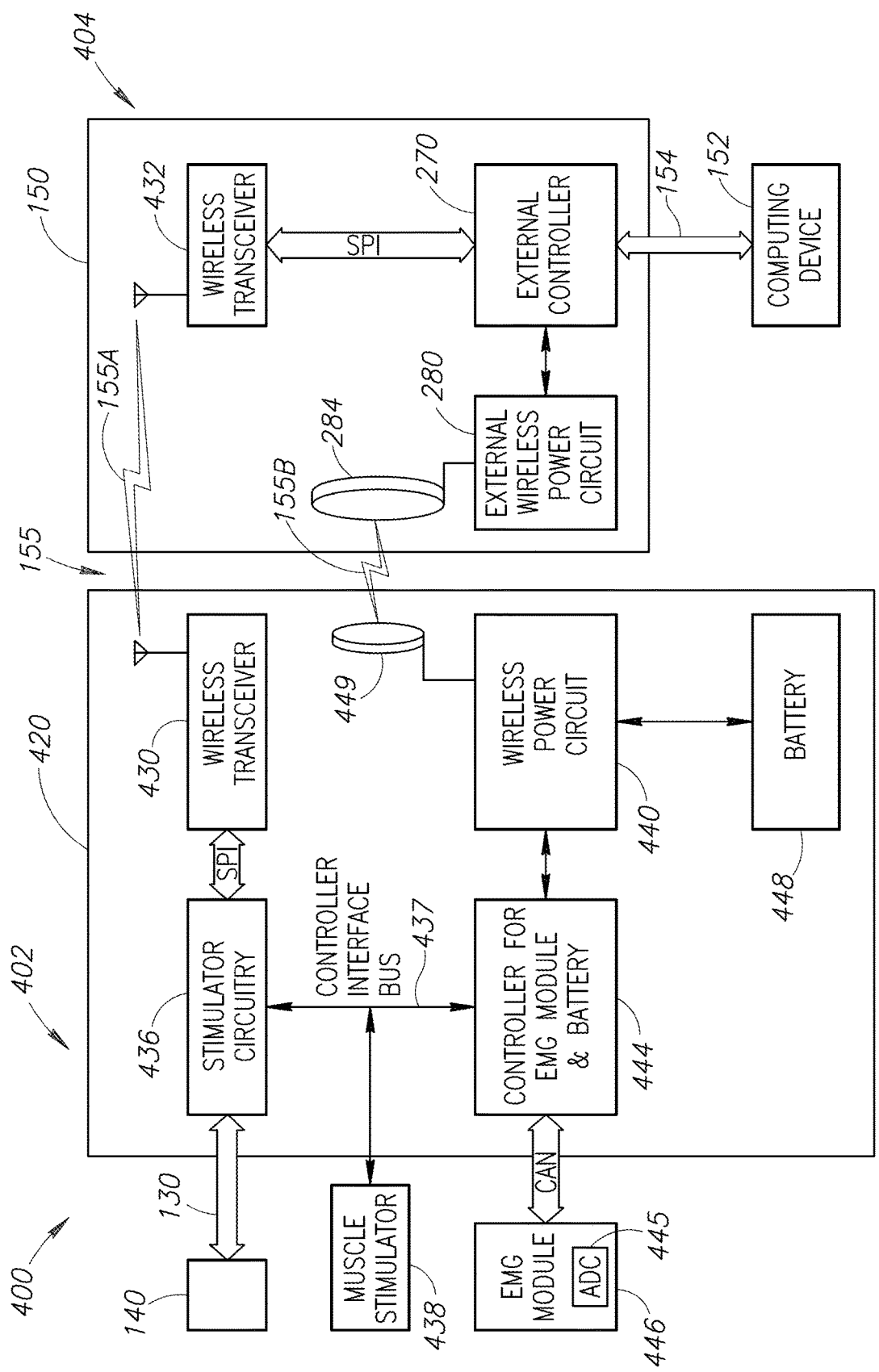
FIG. 11 is a block diagram of a third embodiment of an implantable assembly and the external system.

FIG. 11 illustrates a block diagram of an embodiment of a system 400. The system 400 includes an implantable assembly 402 substantially similar to the assembly 100 described above, and an external system 404 substantially similar to the external system 180 described above. Therefore, only components of the assembly 402 that differ from those of the assembly 100, and components of the external system 404 that differ from those of the external system 180 will be described in detail. For ease of illustration, like reference numerals have been used to identify like components in FIGS. 1-3, 5, and 10-12B.

The assembly 402 includes a neurostimulator device 420, the electrode array 140, and the one or more traces 130. The neurostimulator device 420 is connected by a controller interface bus 437 to an implantable muscle stimulator package 438, and an EMG module 446. The neurostimulator device 420 is configured to interface with and control both the implantable muscle stimulator package 438 and the EMG module 446. By way of a non-limiting example, suitable implantable muscle stimulator packages for use with the system may include a Networked Stimulation system developed at Case Western University.

The neurostimulator device 420 includes a transceiver 430, stimulator circuitry 436, a wireless power circuit 440, a power source 448 (e.g., a battery), and a controller 444 for the EMG module 446 and the power source 448. The illustrated neurostimulator device 420 is configured to interface with and control the separate EMG module 446. However, in alternate embodiments, EMG recording and management capabilities may be incorporated into the neurostimulator device 420, as they are in the neurostimulator device 320 (see FIG. 10). In the embodiment illustrated, the EMG module 446 includes an analog to digital converter ("ADC") 445. Digital data output by the EMG module 446 and received by the controller 444 is sent to the stimulator circuitry 436 via the controller interface bus 437.

The transceiver 430 is configured to communicate with a corresponding transceiver 432 of the external programming unit 150 connected to the external controller 270 over the communication connection 155A. The transceivers 430 and 432 may each be implemented as Medical Implant Communication Service ("MICS") band transceivers. By way of a non-limiting example, the transceiver 432 may be implemented using ZL70102 MICS band transceiver connected to a 2.45 GHz transmitter. The transmitter may be configured to "wake up" the transceiver 430. By way of a non-limiting example, the transceiver 430 may be implemented using a ZL70102 MICS band transceiver.

Figure 12A:
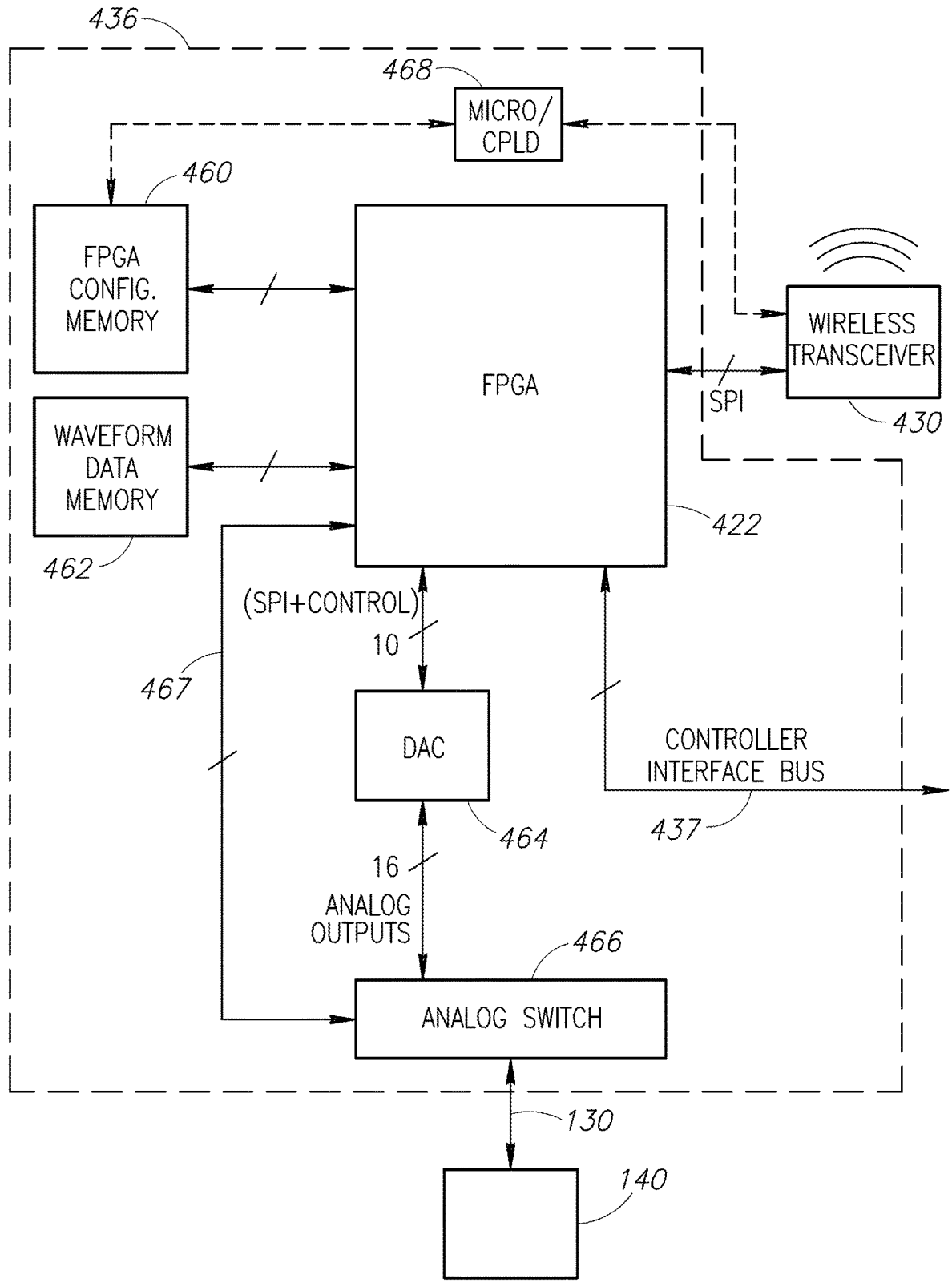
FIG. 12A is a block diagram of stimulator circuitry and a wireless transceiver of a neurostimulator device of the implantable assembly of FIG. 11, according to an example embodiment of the present disclosure.
Figure 12B:
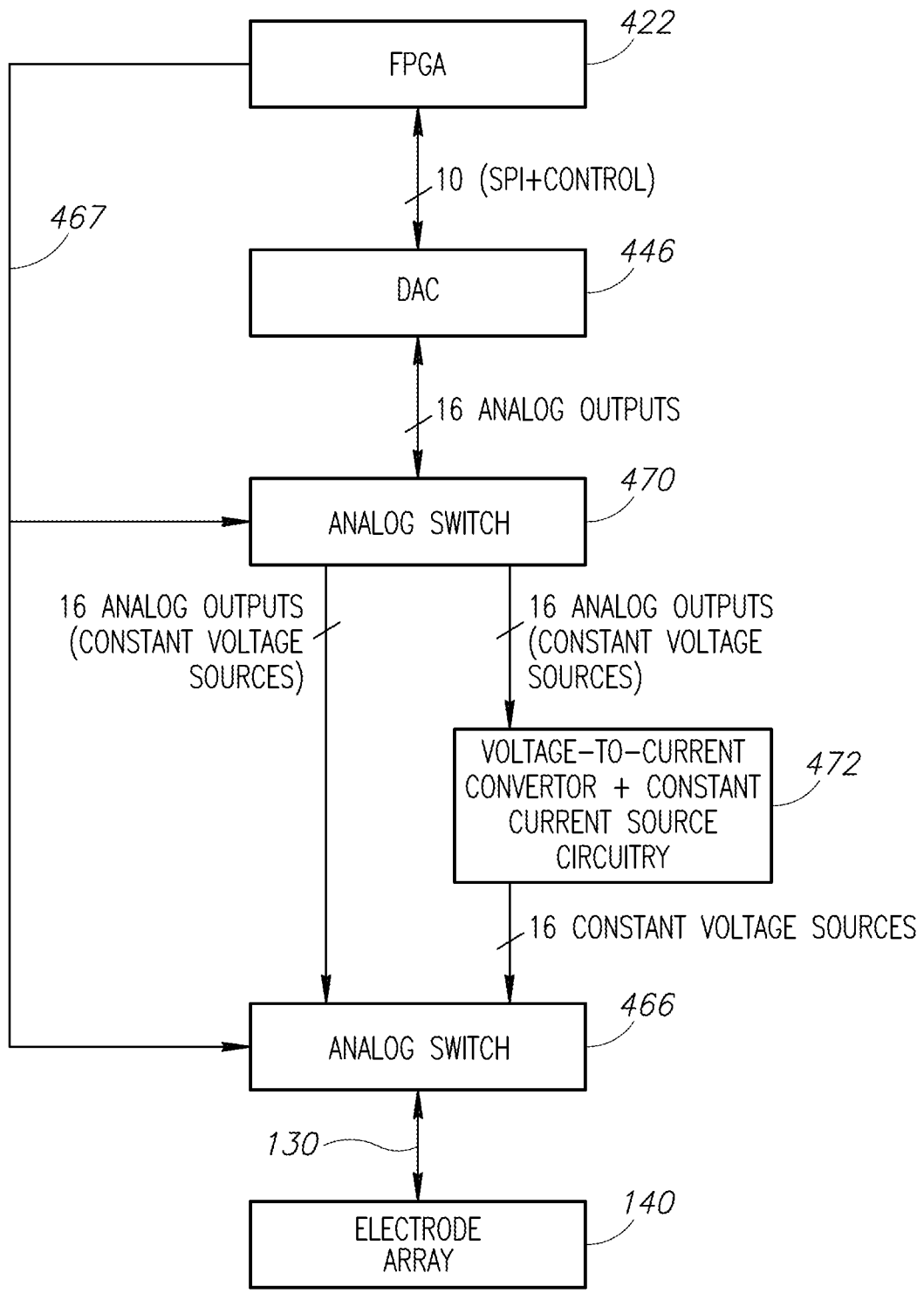
FIG. 12B is a block diagram of an alternate embodiment of the stimulator circuitry of FIG. 12A.

FIG. 12A illustrates a block diagram showing the transceiver 430 and the components of the stimulator circuitry 436. In FIG. 12A, connections labeled "SPI" have been implemented for illustrative purposes using Serial Peripheral Interface Buses. The stimulator circuitry 436 includes a central processing unit ("CPU") or controller 422, one or more data storage devices 460 and 462, a digital to analog converter 464, an analog switch 466, and an optional complex programmable logic device ("CPLD") 468. In the embodiment illustrated, the controller 422 has been implemented using a field-programmable gate array ("FPGA"). Digital data output by the EMG module 446 and received by the controller 444 is sent to the controller 422 via the controller interface bus 437.

The storage device 460 is connected to the controller 422 and configured to store instructions for the controller 422. By way of a non-limiting example, the storage device 460 may be implemented as FPGA configured memory (e.g., PROM or non-flash memory). The optional CPLD 468 is connected between the transceiver 430 and the storage device 460. The optional CPLD 468 may be configured to provide robust access to the storage device 460 that may be useful for storing updates to the instructions stored on the storage device 460.

The storage device 462 is connected to the controller 422 and configured to store recorded waveform data. By way of a non-limiting example, the storage device 462 may include 8 MB or more of memory.

The digital to analog converter 464 is connected to the controller 422 and configured to convert digital signals received therefrom into analog signals to be delivered to the electrode array 140. The digital to analog converter 464 may be implemented using an AD5360 digital to analog converter.

The analog switch 466 is positioned between the digital to analog converter 464 and the leads 130. The analog switch 466 is configured to modulate (e.g., selectively switch on and off) the analog signals received from the digital to analog converter 464 based on instructions received from the controller 422. The analog switch 466 may include a plurality of analog switches (e.g., a separate analog switch for each channel). Optionally, the analog switch 466 may have a high-impedance mode. The analog switch 466 may be configured to operate in the high-impedance mode (in response to instructions from the controller 422 instructing the analog switch 466 to operate in the high-impedance mode) when the neurostimulator device is not delivering stimulation to the electrodes 142. The analog switch 466 may receive instructions from the controller 422 over one or more control lines 467.

In the embodiment illustrated, the ability to directly stimulate muscles (as an adjunct to the neurological stimulation) is not integrated into the neurostimulator device 420 as it is in the neurostimulator device 320 described above and illustrated in FIG. 10. Instead, the controller 422 communicates with the separate implantable muscle stimulator package 438 via the controller interface bus 437. Optionally, a monitor and control subsystem (like the monitor and control subsystem 332 of the neurostimulator device 320) may be omitted from the neurostimulator device 420. However, this is not a requirement.

The neurostimulator device 420 is configured to deliver stimulation to each of a plurality of channels independently. As explained above, each channel corresponds to one of the electrodes 142. Stimulation delivered over a channel is applied to the corresponding one of the electrodes 142. In the embodiment illustrated, the plurality of channels includes 16 channels. However, this is not a requirement. To deliver stimulation, the neurostimulator device 420 uses one positive channel and one negative channel. In some embodiments, signals detected or received by one or more of the electrodes 142 may be received by the neurostimulator device 420 over the corresponding channels.

The neurostimulator device 420 may be configured to control the polarity (positive or negative) or tristate (positive, negative, or high Z) of each of the channels. The neurostimulator device 420 may be configured to deliver stimulation having a frequency within a range of about 0.1 Hz to about 100 Hz. The stimulation delivered may have an amplitude of about −10 Vdc to about +10 Vdc with an increment of about 0.1 Vdc. The neurostimulator device 420 is configured to generate stimulation having a standard waveform shape (e.g., sine, triangle, square, and the like) and/or a custom defined waveform shape. The duty cycle of the neurostimulator device 420 may be configured (for example, for square waveform shapes). The neurostimulator device 420 may provide phase shift in specified increments (e.g., in 25 microsecond increments).

The neurostimulator device 420 may be configured to satisfy timing requirements. For example, the neurostimulator device 420 may be configured to deliver a minimum pulse width of about 50 us and to update all positive channels within a minimum pulse width. In such embodiments, a maximum number of positive channels may be determined (e.g., 15 channels). The neurostimulator device 420 may be configured to accommodate a minimum amount of phase shift (e.g., 25 us phase shift). Further, the neurostimulator device 420 may be configured to update some channels during a first time period (e.g., 25 μs) and to rest during a second time period (e.g., 25 μs). The neurostimulator device 420 may be configured to simultaneously update the output channels.

The neurostimulator device 420 may be configured to satisfy particular control requirements. For example, it may be useful to configure the neurostimulator device 420 so that channel output configuration can be configured on the fly. Similarly, in some embodiments, practical limitations (e.g., a limit of a few seconds) may be placed on update time.

Further, in some embodiments, the neurostimulator device 420 is configured to operate with adjustable custom waveform definitions. It may also be desirable to configure the neurostimulator device 420 such that output stimulation does not stop (or drop-out) during output reconfiguration.

In the embodiment illustrated in FIG. 12A, recording via the EMG module 446 (see FIG. 11) and delivering stimulation to the electrodes 142 may be performed completely separately (or independently). Further, in some embodiments, commands or instructions may be sent to the implantable muscle stimulator package 438 (or an integrated muscle stimulator system) independently or separately. Thus, this embodiment may operate in a full duplex mode.

In an alternate embodiment, the neurostimulator device 420 may be connected to the EMG sensors 190 or recording electrodes (not shown) that are independent of the electrodes 142 used to deliver stimulation. In such embodiments, a pre-amp (not shown) and ADC (not shown) may be included in the stimulator circuitry 436 and used to send digital EMG or nerve recording signals directly to the controller 422. Such embodiments provide two completely separate, continuous time channels between recording and stimulation and therefore, may be characterized as being operable in a full duplex mode. Optionally, the recording electrodes may be incorporated in the electrode array 140 and/or a separate electrode array (not shown).

In another alternate embodiment, the analog switch 466 may be used to switch between a stimulate mode and a record mode. The analog switch 466 may receive instructions from the controller 422 (via the control lines 467) instructing the analog switch 466 in which mode to operate. This implementation may help reduce the number of electrodes by using the same electrodes or a subset thereof to record and stimulate. This exemplary embodiment may be characterized as being operable in a half-duplex mode.

The embodiment illustrated in FIG. 12A the stimulator circuitry 436 is configured to operate in a constant voltage mode. Thus, the output of the DAC 446 (and the analog switch 466) is a plurality (e.g., 16) of constant voltage signals (or sources). However, referring to FIG. 12B, in alternate embodiments, the stimulator circuitry 436 is configured to switch between the constant voltage mode and a constant current mode. In this embodiment, the analog switch 466 includes a separate analog switch (e.g., a single pull, double throw switch) for each channel and a 2-1 multiplexer ("MUX"). This embodiment also includes an analog switch 470 and a circuit block 472. The analog switch 470 may include a separate analog switch (e.g., a single pull, double throw switch) for each channel and a 1-2 demultiplexer ("DEMUX"). The output of the analog switch 470 is a plurality (e.g., 16) of constant voltage signals selectively delivered to either the analog switch 466 or the circuit block 472. Essentially, the analog switches 470 and 466 may be configured to allow either a constant current signal or constant voltage signal to be applied to the electrode array 140.

The circuit block 472 includes voltage to current converter circuitry and constant current source circuitry. The circuit block 472 receives the plurality (e.g., 16) of constant voltage signals from the analog switch 470 and outputs a plurality (e.g., 16) of constant current signals (or sources).

The neurostimulator device 420 may be configured to provide feedback (received from the sensor 188, recording electrodes, and/or the electrodes 142) to the controller 422, which the controller may use to modify or adjust the stimulation pattern or waveform. In embodiments in which the controller 422 is implemented using a FPGA, the FPGA may be configured to modify the complex stimulation patterns delivered to the patient 102 in near realtime. Further, the controller 422 may be used to customize the complex stimulation pattern(s) for different patients.

The wireless power circuit 440 illustrated include a RF charging coil 449 configured to receive power via the power transfer connection 155B. The power received may be used to charge the power source 448 (e.g., a battery).

II. Transcutaneous Device Embodiment

Figure 13:
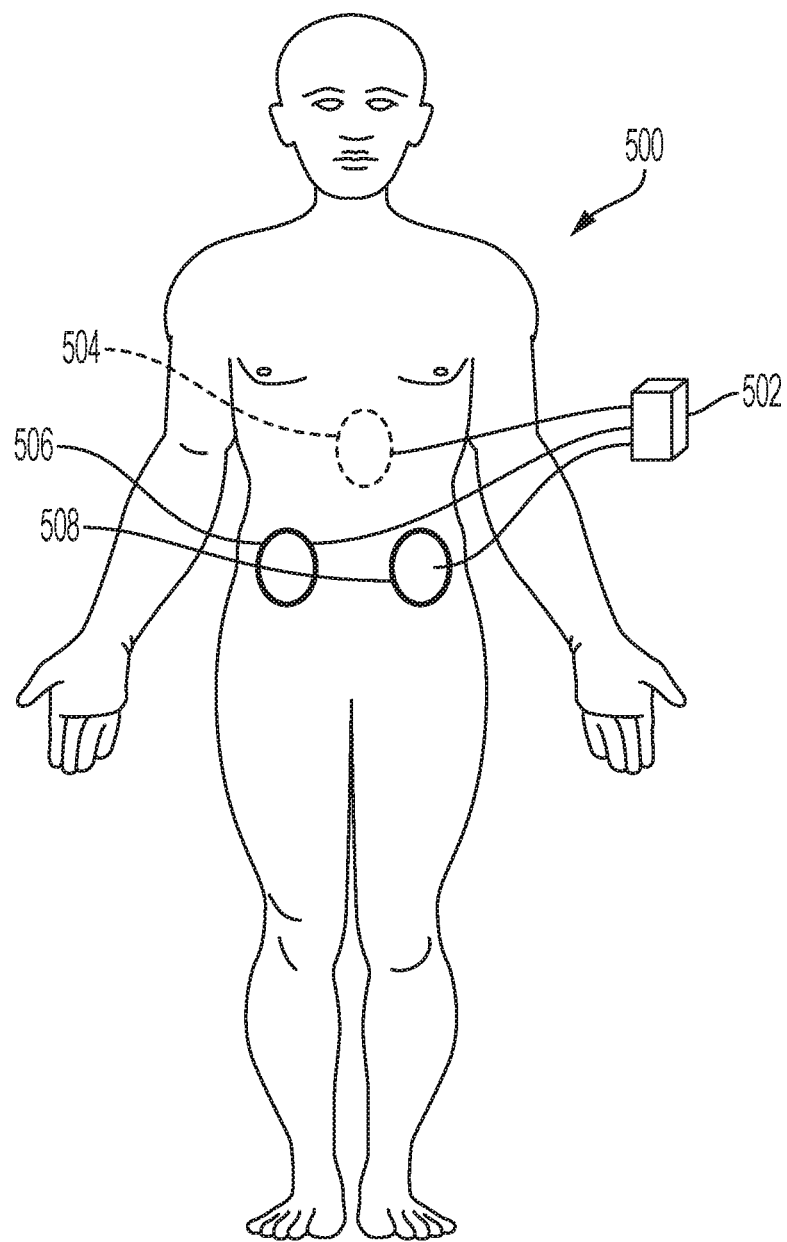
FIGS. 13 and 14 are illustrations of a transcutaneous electrical stimulator, according to an example embodiment of the present disclosure.
Figure 14:
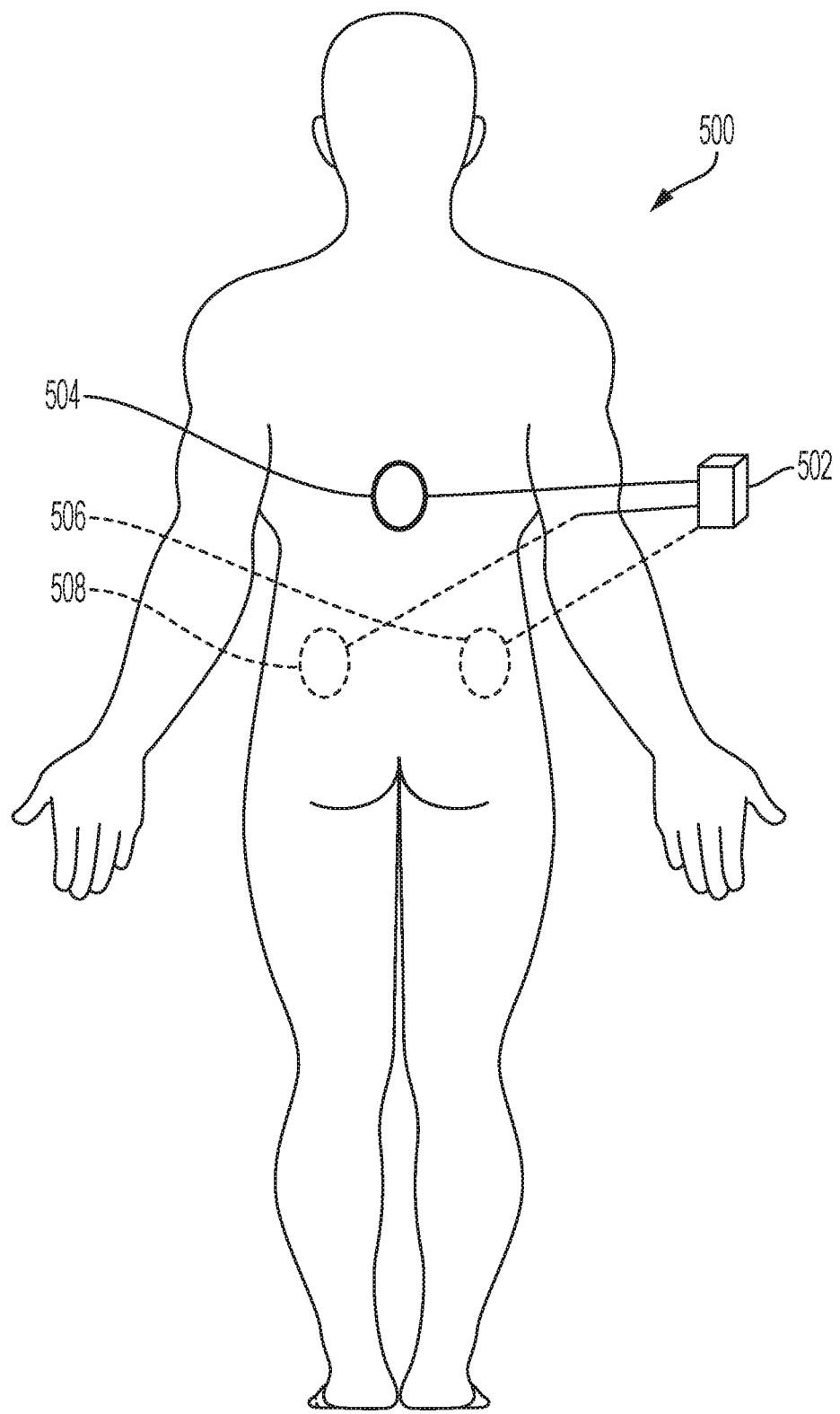
Figure 15:
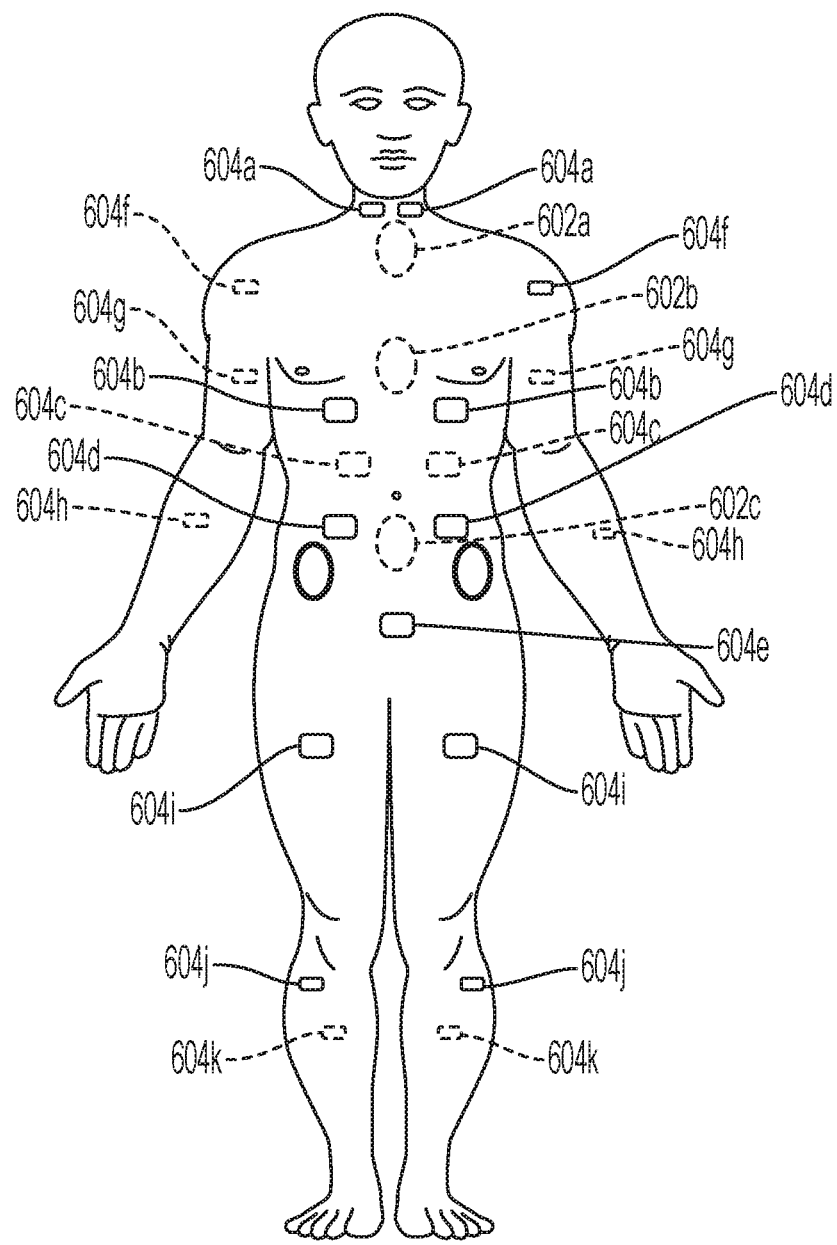
FIG. 15 is an illustration of another example of a transcutaneous electrical stimulator, according to an example embodiment of the present disclosure.

FIGS. 13 to 15 illustrate an embodiment in which the example neuromodulation and/or neurostimulation system, method, and device disclosed herein may be connected transcutaneously to a patient. In this example embodiment, neuromodulation system 500 includes transcutaneous electrical stimulator 502, which is operatively connected to at least one electrode or active electrode 504, a first ground electrode 506, and second ground electrode 508. As shown in FIG. 14, active electrode 504 is disposed on the user's trunk. Such a configuration enables the neuromodulation system 500 to deliver symmetrical stimulation pulse, pattern or waveform. The transcutaneous electrical stimulator 502 includes and/or is in communication with components (including a processor or controller) discussed in connection with the neurostimulator device 120, 120, 220, 320, and 420 of FIGS. 1 to 12 to generate complex stimulation patterns. In addition, the transcutaneous electrical stimulator 502 may be connected to external programming unit 150 and/or the computing device 152 for receiving commands or signals for generating the complex stimulation patterns and providing sensed patient feedback signals.

FIG. 15 provides a diagrammatic view of alternative arrangements of different types of electrodes for the transcutaneous electrical stimulator 502. An active electrode may be placed in any suitable location including, for example, above or below a lesion. For example, as shown in FIG. 15, an active electrode may be placed overlying the user's neck, as shown by 602a, overlying the user's trunk, as shown by 602b, overlying the user's lower back, as shown by 602c, and/or overlying the base of a skull (i.e., the brainstem) (not shown).

As illustrated in FIG. 15, superficial electrodes may be positioned in a plurality of different locations. For example, superficial electrodes 604a are positioned overlying muscles of the neck or throat. Superficial electrodes 604b may be positioned overlying muscles of the diaphragm. Superficial electrodes 604c may be positioned overlying the kidney region. Superficial electrodes 604d may be positioned overlying the stomach region. Superficial electrode 604e may be positioned overlying the pubic region. Superficial electrodes 604f may be positioned overlying the shoulder or upper arm. Superficial electrodes 604g may be positioned overlying the biceps or upper arm. Superficial electrodes 604h may be positioned overlying the forearm. Superficial electrodes 604i may be positioned overlying the upper leg or thigh. Superficial electrodes 604j may be positioned overlying the lower leg or calf. In addition, superficial electrodes 604k may be positioned overlying the lower leg or shin and superficial electrodes 604l may be positioned overlying muscles of the neck or throat. The illustrated transcutaneous electric stimulator 502 may be programmed to switch the polarity between any superficial active electrode and/or the ground electrodes.

The example transcutaneous electrical stimulator 502 may provide a complex stimulation patterns at a frequency between 30 to 40 Hz at 85-100 mA with an overlapping filling frequency between 4 kHz to 10 kHz. In one example embodiment, the transcutaneous electrical stimulator 502 is configured to deliver a biphasic rectangular stimulus with a pulse duration of 0.5 ms, filled with a carrier frequency of 10 kHz. The biphasic stimuli filled with a carrier frequency of 10 kHz may suppress the sensitivity of pain receptors of a patient. In another example embodiment, the transcutaneous electrical stimulator 502 may be configured to deliver a monophasic rectangular stimulus with or without a (rectified) carrier frequency of 10 kHz.

The example transcutaneous electrical stimulator 502 may be configured to apply stimulation waveforms to stimulate a spinal cord, a portion of a spinal cord, a brain, a brainstem, a nerve, a portion of a nerve, a cell body, a ganglia, nerve root, or a targeted end organ or gland; for improving a patient's function after a spinal cord injury, stroke, or other injury or illness leading to paralysis, loss or decrease in movement, or loss or decrease in function whether it be musculoskeletal, autonomic, cardiovascular, cellular, endocrine, or a cognitive function in a mammal or human. The example transcutaneous electrical stimulator 502 may also to configured to be used in conjunction with an implantable device 120, 320, and 420; and/or a bi-directional brain computer interface system; or may be used in conjunction with or integrated to adjunctive equipment such as a robotic exoskeletal system, functional electrical stimulation rehabilitation equipment, or treadmill system; or in a shoe sensor system to improve gait. In each example embodiment, the transcutaneous electrical stimulator 502 incorporates the use of the example dueling bandits algorithm described herein.

III. Machine Learning Algorithm Embodiment

Since each patient's injury or illness is different, it is believed the best pattern of stimulation will vary significantly across patients. Furthermore, it is believed optimal stimuli will change over time due to the plasticity of the spinal cord 110. For this purpose, a learning system (e.g., the computing device 152 and/or one of the neurostimulator devices 120, 220, 320, and 42) may be programmed to "learn" a personalized (or custom) stimuli pattern for the patient 102, and continually adapt this stimuli pattern over time.

The learning system receives input from one or more of the sensors 188 and/or external adjunctive devices, which may be implanted along with the neurostimulator device 220, 320, or 420 (or the transcutaneous electrical stimulator 502) and/or temporarily applied to the patient 102 (e.g., in a clinical setting). Examples of such sensors include the EMG sensors 190, joint angle sensors 191, accelerometers 192, and the like. The external adjunctive devices may include support platforms, support stands, external bracing systems (e.g., exo-skeletal systems), in shoe sensor systems, and/or therapy machines. Information received from the electrodes 142, the connections 194, and/or the external adjunctive devices may be used to tune and/or adjust the complex stimulation pattern delivered by the neurostimulator devices 120, 220, 320, and 42.

The learning system may perform a machine learning method (described below) or dueling bandits routine that determines suitable or optimal stimulation parameters based on information received from the sensors 188. It is believed that it may be more efficient to perform larger adjustments to the stimulation in a clinical setting (e.g., using the computing device 152 and external programming unit 150), and smaller adjustments (fine tuning) on an ongoing basis (e.g., using one of the neurostimulator devices 120, 220, 320, and 42).

In the clinical setting, numerous and sensitive EMG sensors 190, as well as foot pressure sensors (not shown), accelerometers 192, and motion tracking systems (not shown) can be used to gather extensive data on the performance of the patient 102 in response to specific stimuli. These assessments of performance can be used by the learning system to determine suitable and/or optimal stimulation parameters. Soon after the patient 102 is implanted with one of the neurostimulator devices 120, 220, 320, and 420 (or connected to transcutaneous electrical stimulator 502), the patient 102 begins physical training in a clinical setting (e.g., walking on the treadmill 170), which will continue for a few months during which the learning system can tune the stimulation parameters. Thereafter, the patient 102 may return to the clinic occasionally (e.g., on a regular basis (e.g., every 3 months)) for more major "tune ups."

As mentioned above, outside the clinic, the neurostimulator devices 120, 220, 320, and 420 receive signals from on-board, implanted, and external sensing systems (e.g., the electrodes 142, the sensors 188, and the like). This information may be used by the one of the neurostimulator devices 120, 220, 320, and 420 to tune the stimulation parameters.

As mentioned above, the neurostimulator devices 120, 220, 320, and 420 (or transcutaneous electrical stimulator 502) may each be configured to provide patient-customized stimuli, compensate for errors in surgical placement of the electrode array 140, adapt the stimuli over time to spinal plasticity (changes in spinal cord function and connectivity), and facilitate the recovery of multiple motor behaviors or bodily functions. However, with this flexibility comes the burden of finding suitable stimulation parameters (e.g., a pattern of electrode array stimulating voltage amplitudes, stimulating currents, stimulating frequencies, and stimulating waveform shapes) within the vast space of possible patterns and parameters. It is impractical to test all possible parameters within this space to find suitable and/or optimal parameter combinations. Such a process would consume a large amount of clinical resources, and may also frustrate the patient 102. Therefore, a machine learning method is employed to more efficiently search for effective parameter combinations. Over time, the machine learning method may be used to adapt (e.g., occasionally, periodically, continually, randomly, as needed, etc.) the operating parameters used to configure the stimulation.

In one embodiment, the machine learning method (which seeks to optimize the stimuli parameters) alternates between an exploration phase (in which the parameter space is searched and a regression model built that relates stimulus and motor response) and an exploitation phase (in which the stimuli patterns are optimized based on the regression model). By way of a non-limiting example, a Gaussian Process Optimization ("GPO") may be used to determine the stimulation parameters. C. E. Rasmussen, Gaussian Processes for Machine Learning, MIT Press, 2006. GPO is an active learning method with an update rule that explores and exploits the space of possible stimulus parameters while constructing an online regression model of the underlying mapping from stimuli to motor performance (e.g., stepping, standing, arm reaching, and the like). Gaussian Process Regression ("GPR"), the regression modeling technique at the core of GPO, is well suited to online use because it requires fairly minimal computation to incorporate each new data point, rather than the extensive re-computation of many other machine learning regression techniques. GPR is also non-parametric; predictions from GPO are based on an ensemble of an infinite number of models lying within a restricted set, rather than from a single model, allowing it to avoid the over-fitting difficulties inherent in many parametric regression and machine learning methods.

GPR is formulated around a kernel function, which can incorporate prior knowledge about the local shape of the performance function (obtained from experience and data derived in previous neural stimulation studies), to extend inference from previously explored stimulus patterns to new untested stimuli. Given a function that measures performance (e.g., stepping, standing, or reaching), GPO is based on two key formulae and the selection of an appropriate kernel function. The core GPO equation describes the predicted mean $\mu_t(x^*)$ and variance $\sigma_t^2(x^*)$ of the performance function (over the space of possible stimuli), at candidate stimuli $x^*$, on the basis of past measurements (tests of stimuli values $X=\{x_1, x_2, \ldots\}$ that returned noisy performance values $Y_t=\{y_1, y_2, \ldots\}$). To balance exploration of regions of the stimuli space where little is known about expected performance with exploitation of regions where we expect good performance, GPO uses an upper confidence bound update rule. GPO converges with high probability to the optimal action, given sufficient time.

The method described above is a sequential updating method that works in a simple cycle. A single known stimulus is applied to the electrode array, and the patient's response to the stimulus is measured using either implanted sensors (such as EMG sensors 190 connected to the connections 194), and/or using external sensors (such as surface EMG electrodes, foot plate forces, and motion capture data gathered from a video monitoring system). The mean and covariance of the Gaussian Process system are immediately updated based on the single stimulus, and the upper confidence procedure selects the next stimuli pattern to evaluate. This process continues until a termination criteria, such as a minimal increase in performance, is reached.

Alternatively, it may be desirable to propose a batch of stimuli to apply in one clinical therapy session and then evaluate the batch of results, updating the regression model using the entire batch of stimulus-response pairs, and then proposing a new batch of stimulus patterns to be evaluated during the next clinical session. The upper confidence bound method described above can be readily extended to this case.

The definition of a performance function that characterizes human motor behavior (e.g. standing or stepping behavior) may depend upon at least two factors: (1) what kinds of motor performance data is available (e.g., video-based motion capture data, foot pressure distributions, accelerometers, EMG measurements, etc.); and (2) the ability to quantify motor performance. While more sensory data is preferable, a machine learning approach to parameter optimization can employ various types of sensory data related to motor performance. It should be noted that even experts have great difficulty determining stepping or standing quality from such data without also looking at video or the actual patient 102 as he/she undertakes a motor task. However, given a sufficient number of training examples from past experiments and human grading of the standing or stepping in those experiments, a set of features that characterize performance (with respect to the given set of available sensors) can be learned and then used to construct a reasonable performance model that captures expert knowledge and uses the available measurement data.

Figure 16:
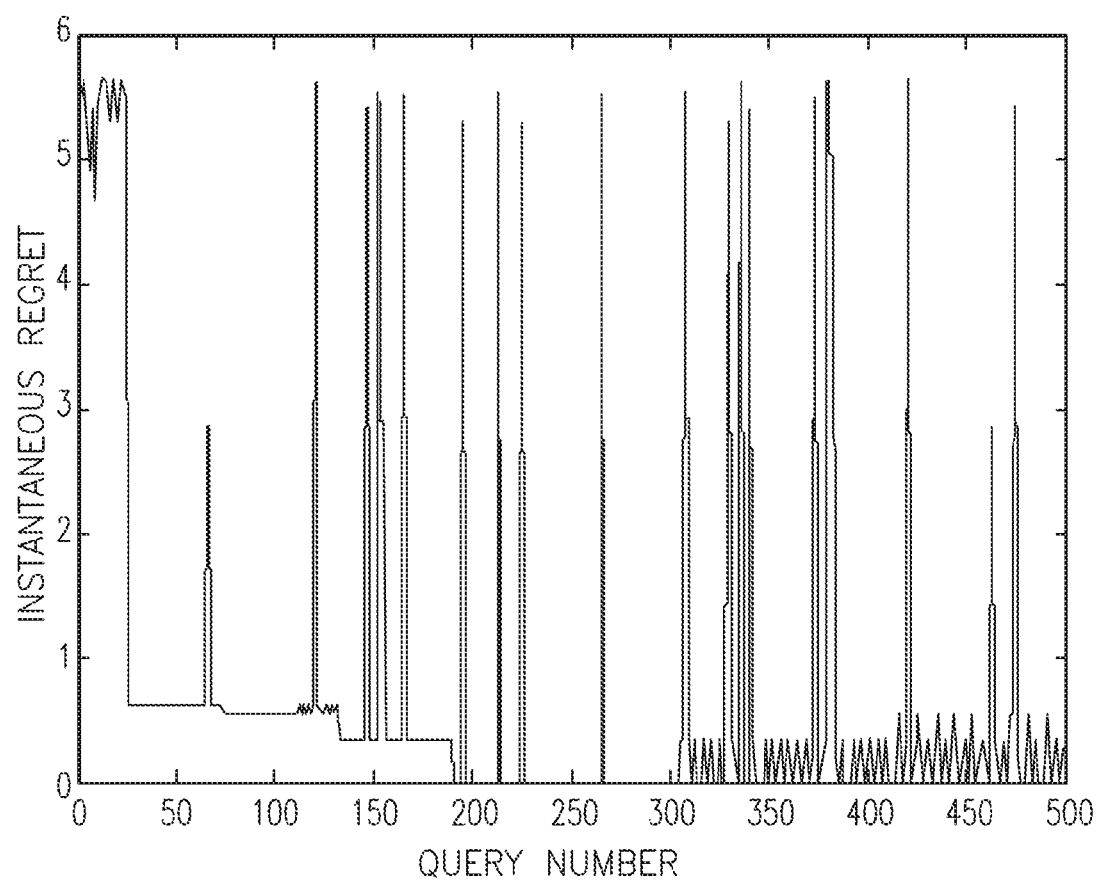
FIG. 16 shows a graph illustrative of instantaneous regret versus learning iteration for a Gaussian Process Optimization algorithm, according to an example embodiment of the present disclosure.

FIG. 16 shows the instantaneous regret (a measure of the error in the machine learning method's search for optimal stimuli parameters) when the Gaussian Process Optimization method summarized above is used to optimize the array stimulus pattern that excites neurons in the dorsal roots between segments L2 and S2 in a spinal cord. The instantaneous regret performance shows that the machine learning method rapidly finds better stimulating parameters, but also continually explores the stimulation space (the "bursts" in the graph of instantaneous regret correspond to excursions of the machine learning method to regions of stimulus parameter space which were previously unknown, but which have are found to have poor performance).

Figure 17:
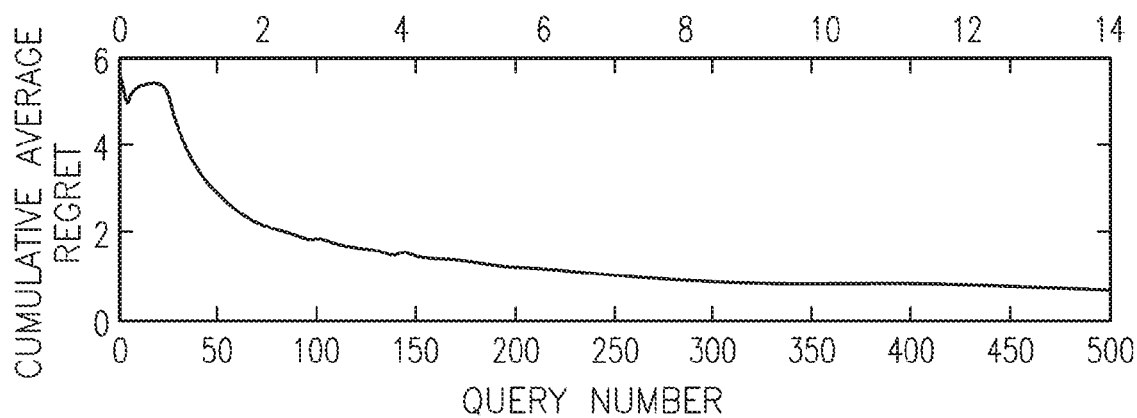
FIG. 17 shows a graph illustrative of an average cumulative regret versus learning iteration, according to an example embodiment of the present disclosure.

FIG. 17 shows the average cumulative regret vs. learning iteration. The average cumulative regret is a smoothed version of the regret performance function that better shows the machine learning method's overall progress in selecting optimal stimulation parameters.

The machine learning method may be performed by the computing device 152 and/or one of the neurostimulator devices 120, 220, 320, and 420 (or the transcutaneous electrical stimulator 502). Thus, instructions for performing the method may be stored in a non-transitory memory storage hardware device of at least one of the computing device 152, the neurostimulator device 220, the neurostimulator device 320, the neurostimulator device 420, or the transcutaneous electrical stimulator 502. Further, these devices may interact during the performance of the method or distribute portions of its execution. By performing the method, the computing device 152, the neurostimulator device 220, the neurostimulator device 320, and/or the neurostimulator device 420 may determine the stimulation parameters (e.g., the waveform shape, amplitude, frequency, and relative phasing) of the complex stimulation pattern applied to the electrodes 142. As discussed above, the machine learning method may implement a Sequential or Batch Gaussian Process Optimization ("GPO") method using an Upper Confidence Bound procedure to select and optimize the stimulation parameters.

IV. Dueling Bandits Algorithm Embodiment

In some embodiments, the computing device 152, the external control unit 150, and/or one of the neurostimulator devices 120, 220, 320, and 420 (or the transcutaneous electrical stimulator 502 and corresponding controller) is configured to use a dueling bandits algorithm to determine, select, or otherwise modify a complex stimulation pattern applied to a patient. The dueling bandits algorithm may be defined within one or more machine readable instructions stored at the computing device 152, the external control unit 150, and/or one of the neurostimulator devices 120, 220, 320, and 420 (or the transcutaneous electrical stimulator 502). The instructions, when executed, cause at least one of the computing device 152, the external control unit 150, and/or one of the neurostimulator devices 120, 220, 320, and 420 (or the transcutaneous electrical stimulator 502) to determine a next optimal complex stimulation pattern based on previous feedback from a patient. The dueling bandits algorithm organizes parameter values for each complex stimulation pattern into separate arms. In some instances, the example dueling bandits algorithm determines (or is provided with the knowledge of) a correlation among at least some of the arms. The correlation among at least some of the arms is used to select next optimal patterns to quickly converge on an optimal complex stimulation pattern without undue experimentation on a patient. The correlation also enables rewards or feedback for one arm to be applied to other arms based on a degree of correlation. In other words, the example dueling bandits algorithm uses correlation and feedback to exploit good stimuli parameter choices to provide a beneficial therapeutic experience for the patient, while also exploring unknown portions of the stimuli parameter space with the goal of finding better stimuli choices, but at the risk of temporarily lowering performance.

Generally, the example dueling bandits algorithm sequentially selects an arm (or group of arms) in such a way as to provide a beneficial therapy for a patient while also exploring the space of stimuli to find optimal choices of parameters. Each choice (or set of choices) is evaluated through a clinical test of the stimuli with the patient using the computing device 152, the external control unit 150, and/or one of the neurostimulator devices 120, 220, 320, and 420 (or the transcutaneous electrical stimulator 502 and corresponding controller). The example dueling bandits algorithm uses a patient's responses to the chosen stimuli to determine how an effectiveness of the stimuli. The goal of the example algorithm is to sequentially explore the space of possible stimuli so as to improve patient performance over time, while also exploiting potentially optimal stimuli within the stimuli space to provide effective therapy to the patient. Over time, the example dueling bandits algorithm finds an optimal set of stimuli for that particular patient (for a particular therapy type) during the period of evaluation/treatment.

The below description of the dueling bandits algorithm provides for a selection of stimuli parameters for a single patient therapy type. It should be appreciated that different therapy types may have different optimal stimuli parameters for the same patient. For example, optimal stimuli parameters for assisting movement of a patient's legs may be different from optimal stimuli parameters for assisting movement of a patient's arms, trunk, neck, etc. Further, different optimal stimuli parameters may exist that treat or reduce a patient's pain, control their bladder and/or bowel function, control their breathing, control their blood pressure or any other bodily function whether it be a musculoskeletal, physiological or cognitive function.

In an example, the dueling bandits algorithm disclosed herein determines stimulation waveform parameters to effectively manage blood pressure, such as in the case of orthostatic hypotension. The example computing device 152, the external control unit 150, and/or one of the neurostimulator devices 120, 220, 320, and 420 (or the transcutaneous electrical stimulator 502 and corresponding controller) uses the dueling bandits algorithm to apply an electrical stimulus over the area of a patient's spinal cord between the 7th and 8th Thoracic vertebrae. The stimulus comprises one or more complex stimulation waveforms have a duration of 1 millisecond ("ms") at 30 Hz using a monophasic waveform, from 0-10 mA or up to 70 mA. The applied waveforms may effectively raise and normalize a patient's blood pressure. The example dueling bandits algorithm optimizes the complex stimulation waveforms (pulse width, frequency, current) and direction of the flow of current (anode to cathode), thereby customizing the therapy to a particular patient.

In another example the disclosed dueling bandits algorithm is operated by the computing device 152, the external control unit 150, and/or one of the neurostimulator devices 120, 220, 320, and 420 (or the transcutaneous electrical stimulator 502 and corresponding controller) to improve standing and trunk control, or hand and arm function by providing a selection of stimulation parameters for an electrical stimulus over an area of a patient's spinal cord between the 11th and 12th Thoracic vertebrae as well as the 1st and 2nd Lumbar vertebrae. The waveforms may include 1 ms pulses at a frequency of 0.2-30 Hz and a current of 10-150 mA. Alternatively, the stimulation waveforms may be applied between the 3rd and 4th, and 6th and 7th Cervical vertebrae in a mono or biphasic waveform. The disclosed waveforms may be applied with or without an overlapping high carrier frequency of 4-10 kHz.

A. Arm Definition Embodiment

The example dueling bandits algorithm organizes stimulation patterns as separate arms. In other words, an arm is a choice of particular stimuli parameters. The dueling bandits algorithm comprises a set, group, or pool B of N arms. The pool B of arms is the set of all possible parameter choices that the disclosed algorithm is permitted to explore and exploit. This set may include all possible electrode stimuli parameters that can be generated by a given multi-electrode array stimulating system, or only a subset of those parameters. A subset of the electrode array's deployable stimuli may be chosen so as to exclude choices of stimuli that are possibly unsafe, or that are known to be ineffective for the particular patient or for the particular multi-electrode stimulating device being used with the algorithm.

Further, some arms may be filtered by the computing device 152, the external control unit 150, and/or one of the neurostimulator devices 120, 220, 320, and 420 (or the transcutaneous electrical stimulator 502 and corresponding controller) based on a therapy type and/or placement of electrodes. For example, some arms may be suitable for only some therapy types, such as leg treatments or for pain relief. In another example, some arms may not be suitable based on a location where electrodes are placed/implanted. A clinician may enter therapy characteristics into a user interface to cause the computing device 152, the external control unit 150, and/or one of the neurostimulator devices 120, 220, 320, and 420 (or the transcutaneous electrical stimulator 502 and corresponding controller) to filter the arms for subsequent analysis and optimization.

FIG. 18 shows a diagram of a graphical illustration of an arm 1800, according to an embodiment of the present disclosure. The example arm 1800 includes an identifier field 1802 configured to distinguish the arm from other arms. The identifier field 1802 may include a unique name, serial number, and/or address. Additionally or alternatively, the identifier field 1802 may include a location of the arm 1800 within a matrix of arms or an index value.

The example arm 1800 of FIG. 18 also includes a parameters field 1804. The example parameters field 1804 specifies one or more parameter values that specify a complex stimulation pattern or waveform. The parameters field 1804 may also specify which electrodes within an array (e.g., electrodes 142 of FIG. 3B) are activate for applying the specified complex stimulation pattern to a patient. Each arm provides different parameters, thereby providing a different waveform, pattern, or group of active electrodes.

FIG. 1900 shows a table 1900 of example parameters for the parameter field 1804 of FIG. 18, according to an example embodiment of the present disclosure. Column 1902 provides a parameter name, column 1904 provides example parameter values for the implantable neurostimulator devices 120, 220, 320, and 42, and column 1906 provides example parameter values for the transcutaneous electrical stimulator 502. It should be appreciated that table 1900 shows one example of parameters and parameter values. In other examples, the table 1900 may include less parameters, additional parameters, and/or different parameter values. For example, an additional parameter may specify therapy type and/or waveform polarity.

In some examples, a therapy may require the input of the parameters shown in table 1900. However, in these examples, the arm 1800 may only include a subset of the parameters (e.g., channels, frequency, pulse width, amplitude, overlapping frequency, mode) for analysis and optimization. For instance, a clinician may select to have some of the parameters not selected when a very specific waveform pulse width and a very specific stimulating frequency works well for almost every patient, and does not need to be optimized or varied. Hence, only the space of active/inactive electrode combinations and stimulating amplitudes may be selected for analysis. In this case, there will be a smaller number of arms because there are few permutations to test.

In the example table 1900 of FIG. 19, the #of channels parameter specifies which electrodes are active when a complex stimulation pattern is applied to a patient. The parameter field may specify which electrodes are to be configured as anodes and which electrodes are to be configured as cathodes, as provided above in Table A. In the illustrated example, the implantable neurostimulator devices 120, 220, 320, and 420 has 32 different channels corresponding to 32 different electrodes available for including in one or more groups. By comparison, the transcutaneous electrical stimulator 502 has four separate channels. Alternatively, the transcutaneous electrical stimulator 502 may have additional channels, for example 12 to 15 channels.

The example frequency parameter specifies a scalar frequency value for a form repetition rate of the stimulating waveform. In the illustrated example, the frequency for the waveform may be between 0.2 and 100 Hz. The example pulse width parameter specifies a width between amplitude peaks of the applied waveform. The pulse width may between 0.1 to 3.0 milliseconds or 0.5 to 5 milliseconds. The system type parameter specifies whether a constant current or constant voltage is applied. The amplitude parameter provides a peak (or peak-to-peak) waveform value for the stimulating pattern. The amplitude may be set between 0.1 milliamps ("mA") to 20 mA or 0 mA 300 mA. In some embodiments, the amplitude is the same for all electrodes. In other embodiments, a different amplitude may be applied to each active electrode or subgroup of electrodes.

The overlapping frequency parameter specifies if an overlapping waveform is applied to a primary waveform for the transcutaneous electrical stimulator 502. The mode parameter specifies if the applied waveform is monophasic, biphasic, or rectified. The waveform parameter specifies a waveform shape, which may include an arbitrary or defined waveform, a square waveform, a sawtooth waveform, etc. The waveform may be indexed to an integer where, for example, a value of '1' corresponds to a square wave. In another example, the waveform may be defined by an equation. For instance, a waveform comprising a finite addition of sinusoids of three different frequencies, omega 1, omega 2, omega 3 may be specified in the waveform parameter as:

$$\text{waveform} = c1*\text{sine}(\text{omega1}*t) + c2*\text{sine}(\text{omega2}*t) + c3*\text{sine}(\text{omega3}*t) \quad (1)$$

In Equation (1) above, t is time, c1 is a contribution coefficient of the first signal, sine(omega1*t), to the stimulating waveform and c2 and c3 respectively describe contributing strengths of the second and third signals. In this example, the waveform parameter may include an index to the specified waveform by the 3-tuple (c1,c2,c3). The implantable neurostimulator devices 120, 220, 320, and 420 may append these numbers onto the tuple that specifies the stimulating parameters.

Returning to FIG. 19, the #of leads parameter specifies a number of leads 130 that are connected to electrodes 142 or 148. A stimulation control parameter specifies an interdependence between the electrodes when the complex stimulation pattern is applied. A therapy duration parameter specifies a time period or time range for applying the complex stimulation pattern. A placement of electrodes parameter specifies locations where electrodes 142 or 148 are implanted or placed on a patient.

In an embodiment, the parameter field 1804 and/or the arm 1800 itself may include a list of numbers and indices that specify a unique stimuli waveform. For example, for a 16 electrode array with a common amplitude for all active electrodes, then the specification for one arm (the 32nd arm for example) may include:

Arm 32=(f=25 Hz; w=200; a=0.1; E1=P, E2=P, E3=N; E4=I, . . . , E15=I, E16=N)

In this example, f is the stimulating wave form repetition rate of 25 Hz, a is the amplitude of stimulating voltage on all active electrodes in milliamps, w is the width of stimulating waveform in microseconds (assuming that it is pulsatile), E1 is electrode #1, E2 is electrode #2, etc., P indicates that the specific electrode is active and has a positive polarity (anode), N indicates that the specific electrode is active and has a negative polarity (cathode), and I indicates that the specific electrode is inactive (or high electrical impedance state).

In another example, if each electrode has its own stimulating amplitude, then the tuple may be specified as:

Arm 32=(f=25 Hz; w=200; a1=0.1; a2=0.5, a15=0.3, a16=1.1; E1=P, E2=P, E3=N; E4=I, . . . , E14=I, E16=N)

In this example, a1 to a16 specify the amplitude of electrode stimuli, etc.

Figure 20:
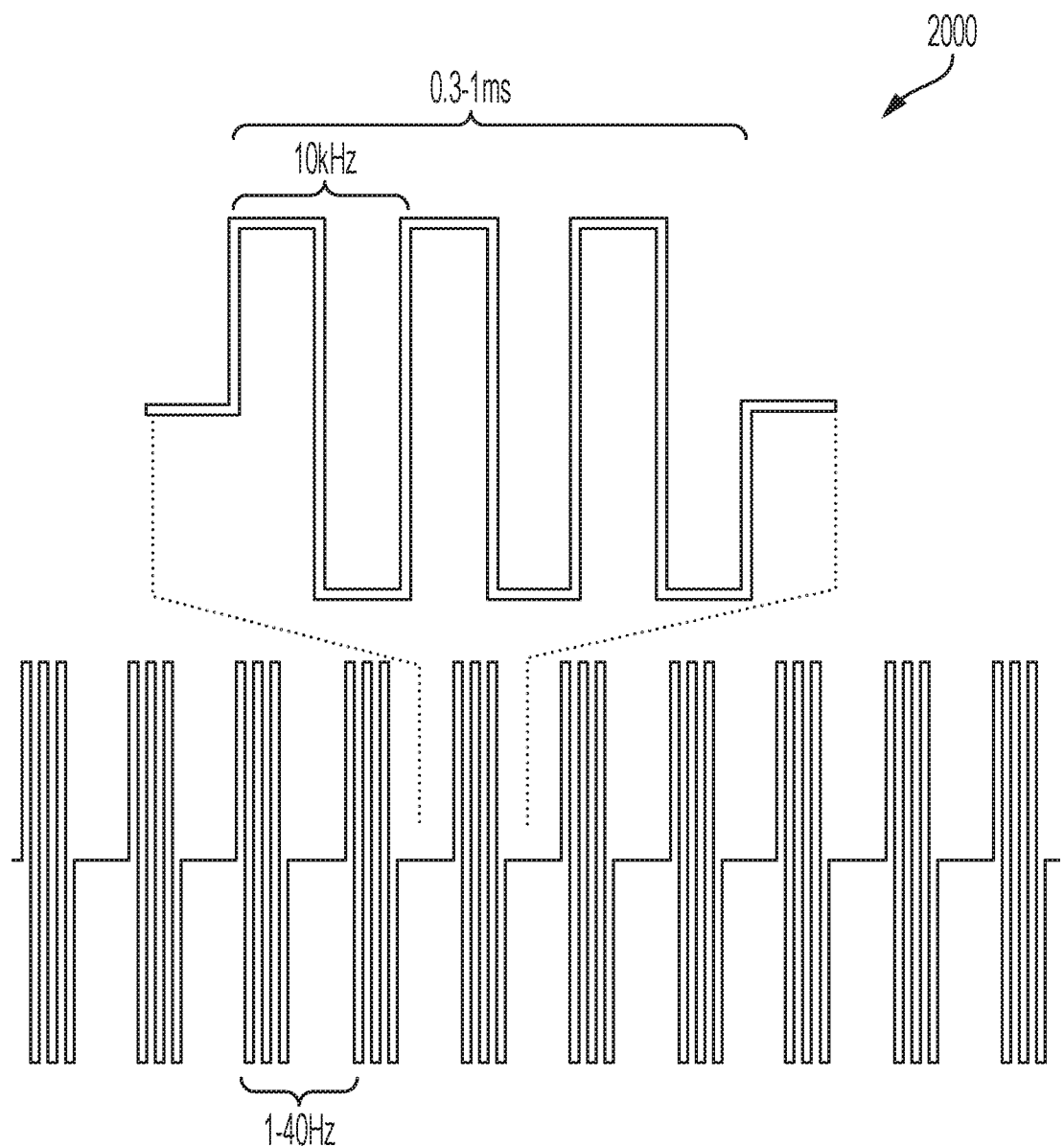
FIG. 20 shows a diagram illustrative of a complex stimulation waveform specified by the parameters of FIG. 19, according to an example embodiment of the present disclosure.

FIG. 20 shows a diagram illustrative of a complex stimulation waveform 2000 specified by, for example, parameters in the table 1900 of FIG. 19, according to an example embodiment of the present disclosure. In the illustrated example, the complex stimulating waveform 2000 has a frequency of 40 Hz with a pulse width of 0.1 ms (10 kHz). In other words, the complex stimulating waveform 2000 is a 1-40 bipolar rectangular stimulus with a duration between 0.3 and 1.0 ms, filled with a carrier frequency of 5-10 kHz. The complex stimulating waveform 2000 may be applied to a patient for a specified duration (e.g., 90 seconds) to determine an effectiveness in assisting a patient regain muscle control. In some instances, the illustrated complex stimulating waveform 2000 may result in less skin impedance, and more comfortable and relatively painless treatment which yields greater compliance and better outcomes.

Returning to FIG. 18, the example arm 1800 may further includes a reward field 1806 configured to store a feedback value or reward. The feedback value or reward is calculated or estimated based on selection of the arm 1800 to provide a stimulation therapy. The reward field 1806 accordingly provides a numerical evaluation of a patient's response to a particular choice of stimulus specified within the parameters field 1804 of the arm 1800. The rewards may correspond to objective and/or subjective feedback. If feedback is not yet available for an arm, the rewards may reflect an estimated reward based on correlations among the arms. Moreover, rewards for an arm may change during subsequent therapy sessions as additional feedback is acquired for other correlated arms. In other words, correlation among arms is used to update or amend reward values based on correspondence between the arms to reflect the current status or condition of a patient.

In some embodiments, the arm 1800 may omit the reward field 1806. In these embodiments, rewards or feedback values may be stored in a separate data structure such that each reward is indexed to the corresponding arm. For instance, the rewards may be stored in a matrix or look up table.

In some instances, the reward or feedback value for the reward field 106 is calculated from measured quantities, such as EMG activity, force plate data, pressure data, motion capture data, etc. measured by sensors 188, 190, 191, and/or 192. For example, the reward may be determined from (1) a largest amplitude of a surface EMG recording of one muscle that is known to be important for an activity such as standing behavior, (2) a power under an EMG signal of a single muscle in a defined interval (e.g., one minute) that results from the applied complex stimulating waveform, (3) a total power under EMG signals of multiple muscles involved in, for example, standing behavior, and/or (4) a force that a patient can exert on a spring-scale measuring device while receiving a specific complex stimulating waveform. For quadriplegic patients, a reward can be realized when the patient squeezes a spring-loaded hand grip. If the springs are calibrated, a deflection of the device under a squeeze can be related to a force generated by the patient. For paraplegics, a loop of string is placed around their big toe while the patient lies supine on a table. The other end of the string is connected to a calibrated spring. The amount of force that the patient can generate (under stimulation) by deflecting their toe or flexing their knee is measured by the spring deflection.

In these instances, the computing device 152, the external control unit 150, and/or one of the neurostimulator devices 120, 220, 320, and 420 (or the transcutaneous electrical stimulator 502 and corresponding controller) may store the sensor data to the reward field 1806 (or separate data structure) or normalize the sensor data. For example, the computing device 152, the external control unit 150, and/or one of the neurostimulator devices 120, 220, 320, and 420 (or the transcutaneous electrical stimulator 502 and corresponding controller) may normalize sensor data to a value between 0 and 1 or 0 and 10 to indicate an effectiveness of the corresponding stimulation parameters.

Figure 21:
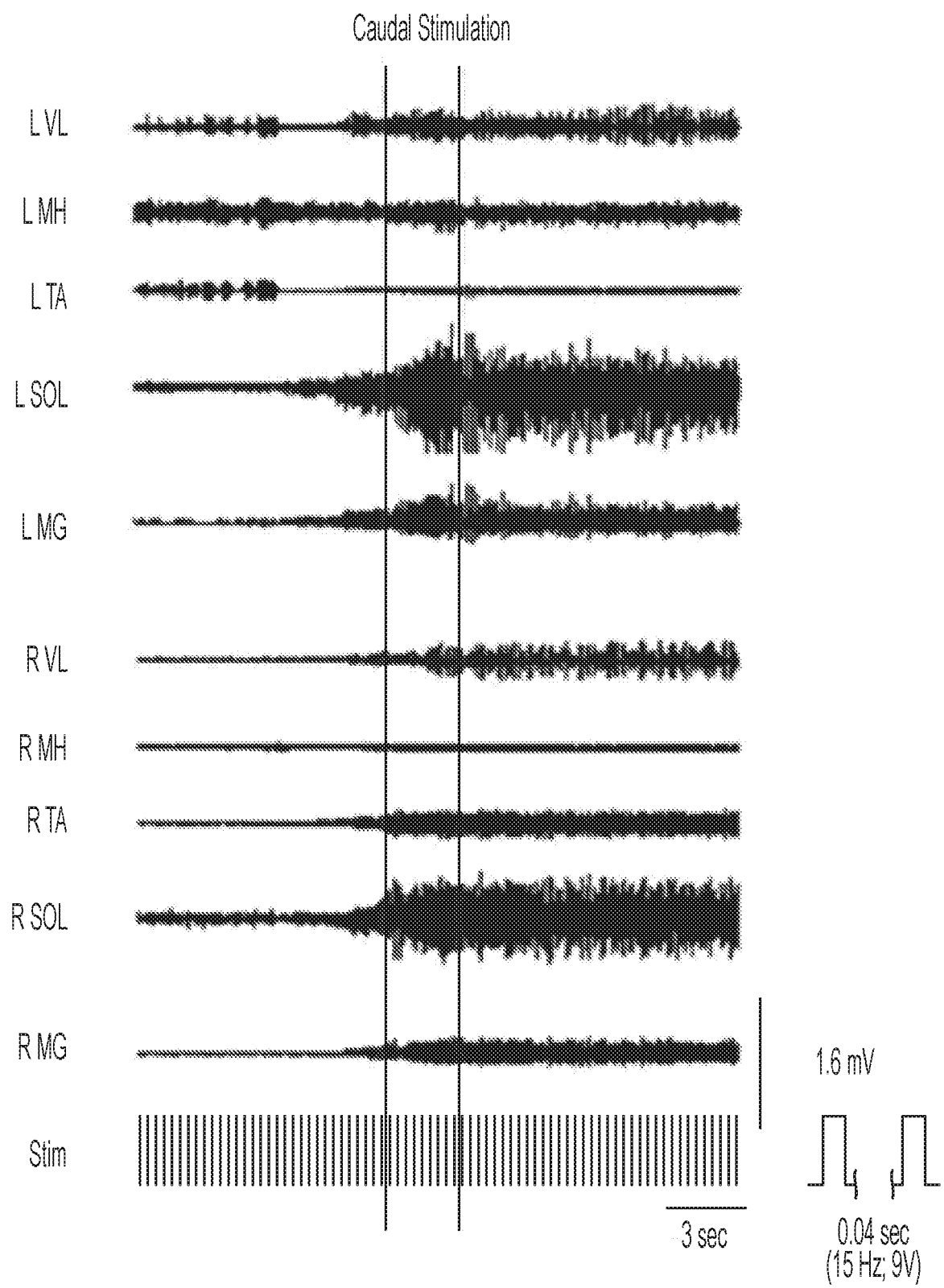
FIG. 21 shows a diagram illustrative of sensor data for determining rewards or feedback values for an arm of a dueling bandits algorithm, according to an example embodiment of the present disclosure.

FIG. 21 shows a diagram illustrative of sensor data for determining rewards or feedback values, according to an example embodiment of the present disclosure. In the illustrated embodiment, a stimulation signal (e.g., "Stim") is applied to a patient undergoing a lower leg therapy. EMG outputs at different muscles (left and right Vastus Lateralis ("VL"), left and right medial hallucis ("MH"), left and right tibialis anterior ("TA"), left and right soleus ("SOL"), and left and right medial gastrocnemius ("MG") are recorded via sensors 88, 190, 191, and/or 192 during the duration of the stimulation. The computing device 152, the external control unit 150, and/or one of the neurostimulator devices 120, 220, 320, and 420 (or the transcutaneous electrical stimulator 502 and corresponding controller) may store the sensor data to the reward field 1806 and/or normalize the sensor data to provide an indication of effectiveness. The computing device 152, the external control unit 150, and/or one of the neurostimulator devices 120, 220, 320, and 420 (or the transcutaneous electrical stimulator 502 and corresponding controller) may normalize the sensor data by integrating the EMG data over time and comparing the integrated data to data buckets. In other instances, the computing device 152, the external control unit 150, and/or one of the neurostimulator devices 120, 220, 320, and 420 (or the transcutaneous electrical stimulator 502 and corresponding controller) may search for peak values or range of maximum values over a predetermined time period for comparison to one or more data bucket. Each data bucket corresponds to a scalar value that has been predetermined regarding effectiveness.

In other instances, the reward field 1806 may store a subjective score (e.g., on a scale of 1-to-10, with 10 being the best) of the patient's response to stimuli. The subjective score may be provided by the patient or from an observing clinician. In this rating scale, for example, each increasing number may correspond to increasing independence of a patient's standing ability (i.e., the less assistance required by the patient to stand (where the assistance can come from assisting therapists, or the subject's use of a stabilizing stand frame)).

In further embodiments, the reward field 1806 may store a combination of both objective (measured) responses and subjective scores. In any of the above-described embodiments, the reward value may be noisy or contain a degree of uncertainty. This uncertainty in the evaluation of the reward may come from noise in the measurement process (e.g., electrical noise on EMG signal measurements), subjective uncertainty in the clinician's or patient's evaluation of the response, and/or variation in the underlying physiological response of the patient to the stimuli. The example dueling bandits algorithm only requires that the source of uncertainty or noise in the measurement has a zero mean. That is, over many measurements, small scoring errors average out.

The clinical process to evaluate a patient's response to one or more complex stimulation waveforms may take some time and some physical effort on the part of the patient undergoing therapy optimization. In one embodiment, a stimulus is applied to a multi-electrode array implanted in a lumbosacral spinal cord of a paralyzed patient in an effort to recover independent standing. To evaluate the effect of the stimulus on the patient's ability to recover independent standing, the patient must attempt to stand, perhaps with the assistance of a stand frame, while the chosen stimulus is applied to the neurostimulator devices 120, 220, 320, and 42. It may take anywhere from a few seconds up to 5 minutes for the standing behavior of the patient under that stimulus to stabilize to a consistent posture. The quality of the patient's response (e.g., the sensor data or subjective observation) is assessed when the patient's standing posture has stabilized.

Returning again to FIG. 18, the arm 1800 may additionally include a correlation field 1808. The example correlation field 1808 may include a matrix of values indicating a correlation of the arm 1800 with other arms. The values in the correlation field indicate an expected closeness of feedback response values and/or parameter values between, for example, arm 1800 and other arms. Relatively high correlation values between the arm 1800 and other arms indicate that the arm 1800 is expected to have a similar response as the other arms. Relatively low correlation values indicate that the arm 1800 is expected to be significantly different from the other arms.

While the illustrated example shows the correlation field 1808 as part of the arm 1800, in other embodiments, values for the correlation field 1808 are stored in a data structure and indexed to the arm 1800. For example, a data structure may store a matrix that provides correlation values between arms. The correlation values are used during the algorithm's process to select the next optimal arms for evaluation in subsequent tests or therapy sessions.

The example dueling bandits algorithm disclosed herein may use a variety of correlation models to determine correlations among the arms. Generally, similar choices of stimuli (e.g., similar patterns of active electrode choices using similar amplitudes and frequencies of stimuli) have similar therapeutic outcomes. Under these circumstances, the corresponding arms are expected to have a high correlation. That is, the choices of similar arms should result in similar, or correlated, responses (rewards). An arm $a_j$ may be correlated to an arm $a_k$ if a reward (e.g., sensor feedback or a subjective observation) in response to selecting $a_j$ is expected to be correlated with the reward that will be obtained if arm $a_k$ were to be selected. Correlation among arms is modeled by a correlation parameter $c_{ij}$: $c_{ij}=C(a_j/a_k)$, where C denotes a function which estimates the correlation between the rewards of arm $a_j$ and arm $a_k$.

The model of correlation can arise from various principles. In one embodiment, the correlation arises from computational models of the electrical stimulation process of the spinal cord. Let $E_j(x,y,z)$ be the spatial distribution of the electrical field potential predicted or modeled by a spinal stimulation model in response to stimuli $a_j$, and let $E_k(x,y,z)$ be the potential field that is modeled in response to stimuli $a_k$. The rewards (or clinical responses) to the two different choices of stimuli are correlated in proportion to the similarity of the electric field distributions in the spinal cord. Hence, the expected correlation of the two responses may be estimated by a 3-dimensional convolution of $E_j(x,y,z)$ with $E_k(x,y,z)$. That is, $c_{ij}$ may be estimated as follows: $c_{ij}=E_j(x,y,z)*E_k(x,y,z)$, where "*" is the 3-dimensional convolution operation.

If there are no correlations between the arms, or if the correlation model is unknown, then all of the estimated correlation parameters are set to zero. The correlations may be computed off-line (i.e., in advance of a therapy session), and stored in the corresponding correlation field 1808 or in a data structure as a look up table or matrix. Additionally or alternatively, the correlations may be computed by the computing device 152, the external control unit 150, and/or one of the neurostimulator devices 220, 320, and 420 (or the transcutaneous electrical stimulator 502 and corresponding controller) as needed during the on-line parameter exploration process.

The example arm 1800 of FIG. 18 (and the other arms) may be stored in a memory of the computing device 152, the external control unit 150, and/or one of the neurostimulator devices 120, 220, 320, and 420 (or the transcutaneous electrical stimulator 502 and corresponding controller). For example, the arm 1800 may be stored to the data storage device 462 of FIG. 12A. Additionally or alternatively, data structures, look up tables, and/or matrices for rewards and/or correlation values may be stored to the data storage device 462.

B. Dueling Bandits Process Embodiment

The example the computing device 152, the external control unit 150, and/or one of the neurostimulator devices 120, 220, 320, and 420 (or the transcutaneous electrical stimulator 502 and corresponding controller) is configured to operate according to a dueling bandits algorithm to select one or more complex stimulation waveforms for a patient's therapy session. Feedback results (i.e., rewards) from the therapy session are used to determine the next stimuli (e.g., complex stimulation wavefroms), or set of stimuli, to be tested. In one embodiment, the feedback results may also be used to change the stored reward values and/or the stored correlation values. The dueling bandits algorithm may then be executed again to select the next complex stimulation waveforms to be evaluated. This iterative process continues over subsequent therapy sessions until one or more optimal complex stimulation waveforms are identified.

Figure 22:
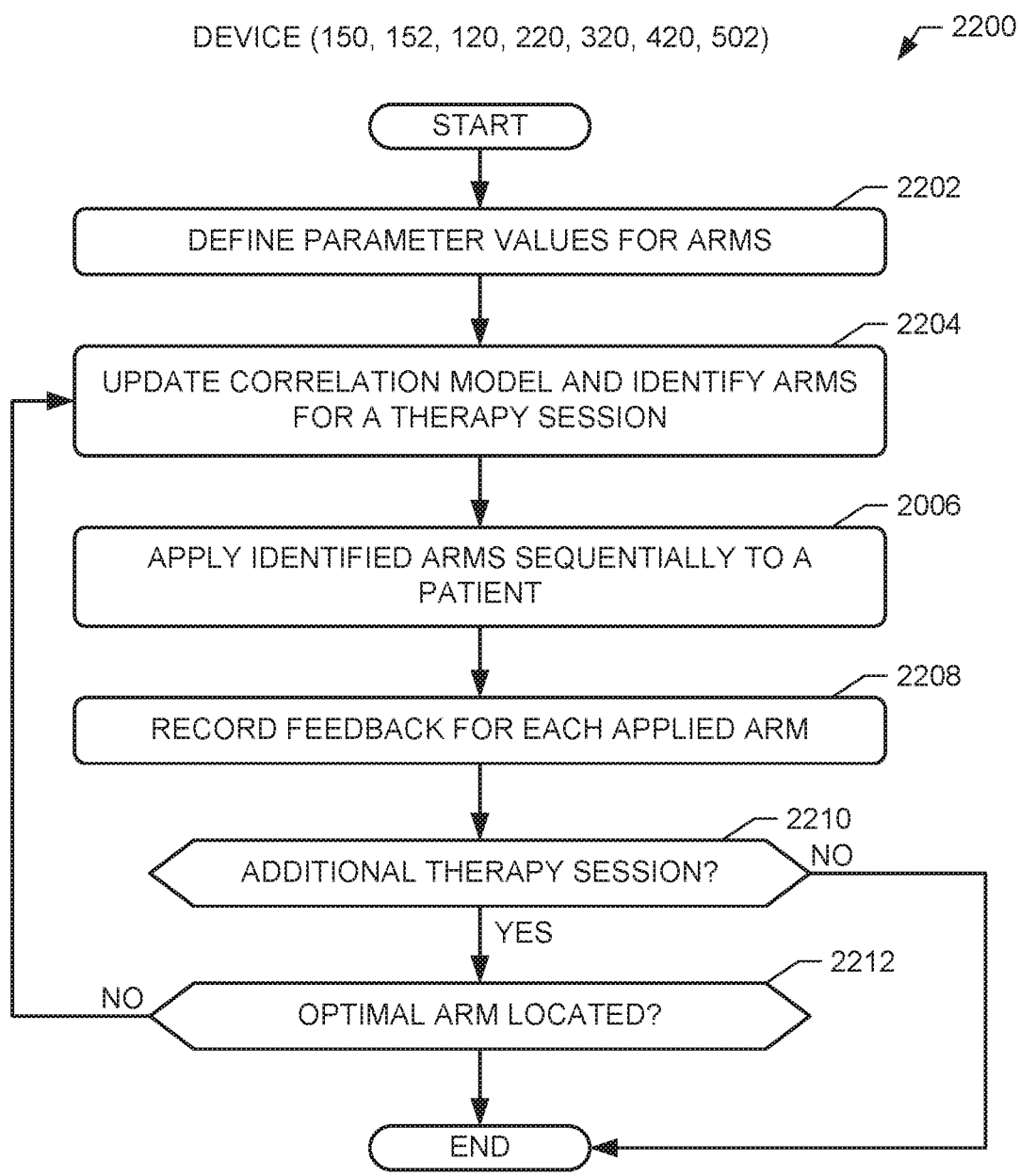
FIG. 22 illustrates a flow diagram showing an example procedure using a dueling bandits algorithm to select one or more arms for applying complex stimulation waveforms to a patient, according to an example embodiment of the present disclosure.

FIG. 22 illustrates a flow diagram showing an example procedure 2200 using a dueling bandits algorithm to select one or more arms for applying complex stimulation waveforms to a patient, according to an example embodiment of the present disclosure. Although the procedure 2200 is described with reference to the flow diagram illustrated in FIG. 22, it should be appreciated that many other methods of performing the steps associated with the procedure 2200 may be used. For example, the order of many of the blocks may be changed, certain blocks may be combined with other blocks, and many of the blocks described are optional. Further, the actions described in procedure 2200 may be performed among multiple devices including, for example the computing device 152, the external control unit 150, and/or one of the neurostimulator devices 120, 220, 320, and 420 (or the transcutaneous electrical stimulator 502 and corresponding controller).

The procedure 2200 provides a stimulus optimization process that occurs over a set of clinical sessions. The procedure 2200 begins when the parameter values for stimulation arms are created and/or defined (block 2202). The arms may be created manually via a clinician using a user interface of the computing device 152 and/or the external control unit 150. Alternatively, the stimulation arms may be created automatically by specifying acceptable parameter ranges and increments. An automated routine then generates different combinations of parameter values to account for substantially all acceptable stimulation waveforms and/or electrode groupings. In some instances, a clinician or an automated routine may filter or otherwise remove stimulation arms with unacceptable parameter values, arms known not be effective, or arms not applicable for a specified therapy type/electrode configuration.

The example procedure 2200 then loads a correlation model into memory, or updates a correlation model among the stimulation arms, and operates a dueling bandits algorithm to select stimulation arms for a therapy session (block 2204). For example, the procedure recommends sequential batches of k arms (k choices of complex stimulation waveforms) to evaluate during a therapy session. The size of the batch can be as little as two arms (k=2). But often k is a small integer, such as 5, 7, 10, etc. The k choices of complex stimulation waveforms comprising the batch are applied, one at a time, to the patient (block 2006). The order in which the complex stimulation waveforms are applied does not matter. After each complex stimulation waveform is applied to the patient, the response of the patient (as measured by the reward that was described above) is measured after the complex stimulation waveform has had suitable time to influence the patient's behavior (block 2008).

It should be appreciated that the size of the batch is arbitrary, but is best set using the consideration of clinical issues, which may vary between clinics and across patients. For example, a patient undergoing stimulus evaluation and stimulated therapy needs a physical rest period after the process of evaluating multiple complex stimulation waveforms, since each evaluation may require physical exertion of the patient. If the clinician expects that the patient can comfortably endure the physical process needed to evaluate 7 choices of complex stimulation waveforms, then the clinician will set a batch size of 7. After testing all of the complex stimulation waveforms in the batch, the patient is given a rest period.

During the rest period, all of the clinical data (e.g., the objective and subjective rewards), which has been recorded after the application of each complex stimulation waveform in the batch, is processed to produce a ranked list of the quality of responses (or "rewards") in that batch. As described below, the dueling bandits algorithm uses these rankings to update its internal model, and then uses the updated model to suggest a next batch of complex stimulation waveforms for evaluation if there are additional therapy sessions (block 2210). If there is another session, the procedure 2200 may determine if an optimal arm has been located (block 2212). As is made clear below, an optimal stimulation arm is identified if there is only one arm left in the pool of arms under consideration by the algorithm. If an optimal arm has not yet been located, the next batch of stimuli may be evaluated, as described above, within the same clinical session, or they may be tested at the beginning of the next clinical session if the patient is too fatigued (block 2204). If there are no additional sessions and/or an optimal arm has been identified, the procedure ends 2200.

It should also be appreciated that the size of the batch need not be constant over time. A first therapy session may include 2 arms while subsequent therapy sessions include 5 arms. Moreover, a supervising clinician can reject one or more suggested complex stimulation waveform within the batch. For example, specific choices of complex stimulation waveforms within a batch could be rejected by the supervising clinician if they thought that the patient's response to that complex stimulation waveform is apt to be poor, or the complex stimulation waveform will jeopardize the therapy process by inducing too much fatigue while testing that particular waveform.

An example of the dueling bandits algorithm performed in procedure 2200 is provided below in more detail. A portion of the dueling bandits algorithm, referred to a CorrDuel is shown below in Table B. The algorithm shown in Table B uses feedback (e.g., rewards) from complex stimulation waveforms and the correlational structure between arms to successively remove suboptimal arms from the initial pool, while keeping the optimal arm(s) with high probability.

TABLE B

Algorithm 1 CORRDUEL

1: input: $\beta$, T, ($\kappa$, $\tau$)
2: Input: $c_\delta(n) = \sqrt{(1/n)\log(1/\delta)}$
3: Run: [Parameters-Initialization]
4: Run: [Active-Elimination]
5: return b* // Optimal arm The inputs (Line 1, 2) to the CorrDuel algorithm (of the dueling bandits algorithm) include a set of arms (or initial pool), B of K arms $\{b_1, \ldots b_K\}$. T is the total number of test iterations (the maximum number of complex stimulation waveform tests that can be carried out with a patient). In addition, ($\kappa$,$\tau$) is the correlational values or rules among the arms and $c_\delta(n)$ is a confidence interval control parameter. Note that $c_\delta(n)$ depends upon the present number of arm comparisons, or trials, n that have been carried out. As discussed below, n=1 at the start of the first trial with a patient. If the optimization is restarted after a number of trials, then n represents the trials attempted until that point in the therapy. The confidence parameter is a function of $\delta$, a parameter which quantifies the confidence interval, $\hat{C}_{b,n}$, which is defined below in Equation (2):

$$\hat{C}_{b,n} = (P_{b,n} - c_\delta(n), P_{b,n} - c_\delta(n)) \quad (2)$$

In Equation (2) above, $P_b$ is the empirical average of $P(b>b')$ for all $b' \in W_l$, and $P_{b,n}$ is the value of $P_b$ after n comparisons of b with any other arm in the pool $W_l$. As described below, $W_l$ is the pool of currently acceptable stimulation arms. This pool is initially set to the input set of arms, B. The confidence parameter $\delta$ defines the confidence interval $\hat{C}_{b,n}$ which helps to determine when arms are removed from the pool, $W_l$. Practically, the confidence interval enables the example dueling bandits algorithm to properly account for noise and uncertainty in the reward measurements. The confidence interval states that, with confidence $\delta$, the true value of the reward for arm b lies in the interval $\hat{C}_{b,n}$ after n tests with arm b. As more clinical tests with arm b are carried out, the confidence interval shrinks, indicating a higher confidence in the reward estimated for that stimulation arm from the clinical data. The correlational rules ($\kappa$,$\tau$) are defined below.

Returning to the CorrDuel algorithm above in Table B, Line 3 calls a subroutine that is referred to as Parameters-Initialization (described below). In addition, Line 4 of the CorrDuel algorithm calls a subroutine that is referred to as Active-Elimination (also described below). After running the subroutines in Lines 3 and 4, Line 5 of the CorrDuel algorithm returns one or more selected next-optimal arm(s) as an output. The selected next-optimal arms correspond to the complex stimulation waveforms in a batch that are applied to a patient during a therapy session.

The Parameters-Initialization subroutine, shown below in Table C, defines the set of active arms as $W_l$ (this is the current pool of arms, which consists of the original pool B, minus any arms that have been deemed suboptimal during the run of the dueling bandits algorithm to that point in time). The number of active arms shrinks as more tests or trials are completed. The Parameters-Initialization subroutine may also account for any prior knowledge available about the active set of arms, and can also account for any previous "runs" of the dueling bandits algorithm. That is, the Parameters-Initialization subroutine can allow for the optimization process to be restarted after a lapse in testing with a patient.

TABLE C

Algorithm 2 Parameters-Initialization

1: $W_1 \leftarrow \beta$ // set of active arms
2: $\ell \leftarrow 1$ // rounds
3: $\forall b \in W_\ell$, $n_b \leftarrow 0$ // comparisons
4: $\forall b \in W_\ell$, $w_b \leftarrow 0$ // priorities
5: $\forall b \in W_\ell$, $\hat{P}_b \equiv w_b/n_b$, or ½ if $n_b = 0$
6: $n^* \equiv \min_{b \in W_\ell} n_b$
7: $c^* \equiv c_\delta(n^*)$, or 1 if $n^* = 0$ // confidence radius
8: $t \leftarrow 0$ // total number of iterations
9: return all new parameters In the Parameters-Initialization subroutine, for each arm b, $n_b$ is the total number of comparisons between arm b and other arms that may have been accomplished before the current run of the algorithm. $w_b$ is the total number of wins (e.g., weights) against all other arms in any previous run of the algorithm with a patient. In Line 5 of the Parameters-Initialization subroutine, $P_b$ is defined as be the empirical average of $P(b>b')$ for all b'. As before, $P_{b,n}$ is the value of $P_b$ after n comparisons between arm b and any other arms. Parameters n* and c* are set according to Lines 6 and 7. In Line 8, the current run of the algorithm is initiated with t=0. Then, in Line 9, the Parameters-Initialization subroutine returns all new parameters to the CorrDuel algorithm described above.

The example Active-Elimination subroutine, shown below in Table D, compares arms to determine one or more next-optimal arms. The 'while loop' in Line 1 of the Active-Elimination subroutine indicates that the routine continues to run until either there is only a single arm in the remaining pool of arms (i.e., an optimal complex stimulation pattern has been found), or the maximum number of tests, T, has been reached. For each pair of tests, two arms are randomly chosen from $W_l$. The randomized selection method has a low-variance total regret. For each arm b, the values of $w_b$, $n_b$ and $\hat{P}_b$ $w_b$, $n_b$, and $P_b$ are updated, as is the corresponding confidence radius $c^* = c_\delta(n)$. An arm b dominates another arm b', if their confidence intervals do not overlap, and the inferior arm (whose upper confidence value is below the lowest confidence value of the superior arm) is eliminated from $W_l$.

TABLE D

Algorithm 3 Active-Elimination

1: while $|W_\ell| > 1$ and $t \le T$ do
2:   select $b_i, b_j \in W_\ell$ at random
3:   compare selected arms (assume $b_i \succ b_j$)
4:   for all $b_k \in W_\ell$ do
5:     update $w_k$, $n_k$ by CORRUPDATE
6:   end for
7:   if $\min_{b' \in W_\ell} \hat{P}_{b'} + c^* \le \max_{b \in W_\ell} \hat{P}_b - c^*$ then
8:     $b \leftarrow \arg \min_{b' \in W_\ell} \hat{P}_{b'}$
9:     $\forall b \in W_\ell$, delete comparisons with b' from $w_b$, $n_b$
10:    $W_{\ell+1} \leftarrow W_\ell \setminus \{b'\}$ // update working set
11:    $\ell \leftarrow \ell + 1$ // new round
12:  end if
13: end while
14: return $b^* = \arg\max_{b \in W_\ell} \hat{P}_b$ The example Active-Elimination subroutine includes a further subroutine referred to as CorrUpdate. The CorrUpdate subroutine is shown below in Table E and is configured to updates the weights of $b_k$ by the correlation rules $\kappa(*;*,*)$ and $\tau(*;*,*)$.

TABLE E

Algorithm 4 CORRUPDATE

1: Input: $b_k$, $b_i \succ b_j$
2: $w_k \leftarrow w_k + \kappa(b_k; b_i, b_j)$
3: $n_k \leftarrow n_k + \tau(b_k; b_i, b_j)$
4: return $w_k$, $n_k$ The correlation rules of the CorrUpdate subroutine satisfy the following constraints shown below in Equations (3), (4), and (5):

$$0 \le \kappa(b_k; b_i, b_j) \le \tau(b_k; b_i, b_j) \le 1; \quad (3)$$

If $b_k = b_i$, then $\kappa(b_k; b_i, b_j) = \tau(b_k; b_i, b_j) = 1;$ (4)

If $b_k = b_j$, then $\kappa(b_k; b_i, b_j) = 0$ and $\tau(b_k; b_i, b_j) = 1;$ (5)

In one embodiment of the CorrUpdate subroutine, the correlation rules can be expressed as a function of the correlation coefficients $c_{ij}$ as provided below in Equations (6) and (7):

$$\kappa(b_k; b_i, b_j) = \frac{\log(c_{jk})}{\log(c_{ik}) + \log(c_{jk})} \cdot \frac{c_{ik} + c_{jk}}{1 + c_{ij}} \quad (6)$$

$$\tau(b_k; b_i, b_j) = \frac{c_{ik} + c_{jk}}{1 + c_{ij}} \quad (7)$$

When the arms are correlated and the correlation between any pair of arms $b_i$ and $b_j$ is measured properly, all active arms can be updated at each iteration. As shown in the CorrUpdate subroutine, every arm $b_i$ is updated after comparing arms $b_i$ and $b_j$, where $\kappa(*;*,*)$ and $\tau(*;*,*)$ represent the correlational rules.

It should be appreciated that the arms (or values of the waveform parameters) to be tested on the patient are randomly chosen. This ensures that the dueling bandits algorithm works well across a large population of patients. However, in another embodiment, the arms selected at Line 2 of Active-Elimination subroutine are not randomly chosen. Instead, the computing device 152, the external control unit 150, and/or one of the neurostimulator devices 120, 220, 320, and 420 (or the transcutaneous electrical stimulator 502 and corresponding controller) may use computational models, prior clinical results, or other intuitive factors to select the arms to be tested.

It should be appreciated that the above example of the dueling bandits algorithm provides for a batch size of 2. However, the dueling bandits algorithm may accommodate larger batch sizes or a smaller batch size of 1. For larger batch sizes, Line 2 of the Active-Elimination subroutine, k>2 arms (possibly with repeated selection of an arm) is randomly chosen instead of two arms: i.e., choose arms $b_{j1}$, $b_{j2}$, … $b_{jk}$. In addition, in Line 3 of the Active-Elimination subroutine, each arm is evaluated to yield a reward. Then, all pairwise comparisons of arms are made (i.e., k choose 2 comparison between each pair of arms in the batch). Then, the CorrUpdate subroutine is called with all pairwise comparisons. Otherwise the dueling bandits algorithm remains the same.

For a batch size of one, only a single arm (e.g., one complex stimulation waveform) is tested on a patient. Hence, in Line 2 of the Active-Elimination subroutine, a single arm $b_i$ is chosen (randomly, or otherwise). In Line 3 of the Active-Elimination subroutine, a comparison is made between the arm just chosen ($b_i$) and the arm chosen in the last iteration of the algorithm, which is label as $b_j$. The updating in Lines 4-to-6 of the Active-Elimination subroutine proceeds as discussed above.

C. Experimental Results

The above described dueling bandits algorithm with correlation between arms was tested through simulation and patient experiments. Generally, results show that the correlations between arms of the example dueling bandits algorithm provide an accurate relation of the arms' effectiveness on a patient. Moreover, the results generally show that the dueling bandits algorithm with arm correlation converges more quickly to optimal (or near-optimal) complex stimulation waveforms than known Gaussian Process bandit optimization algorithms and dueling bandits algorithms that use independent arms.

Figure 23:
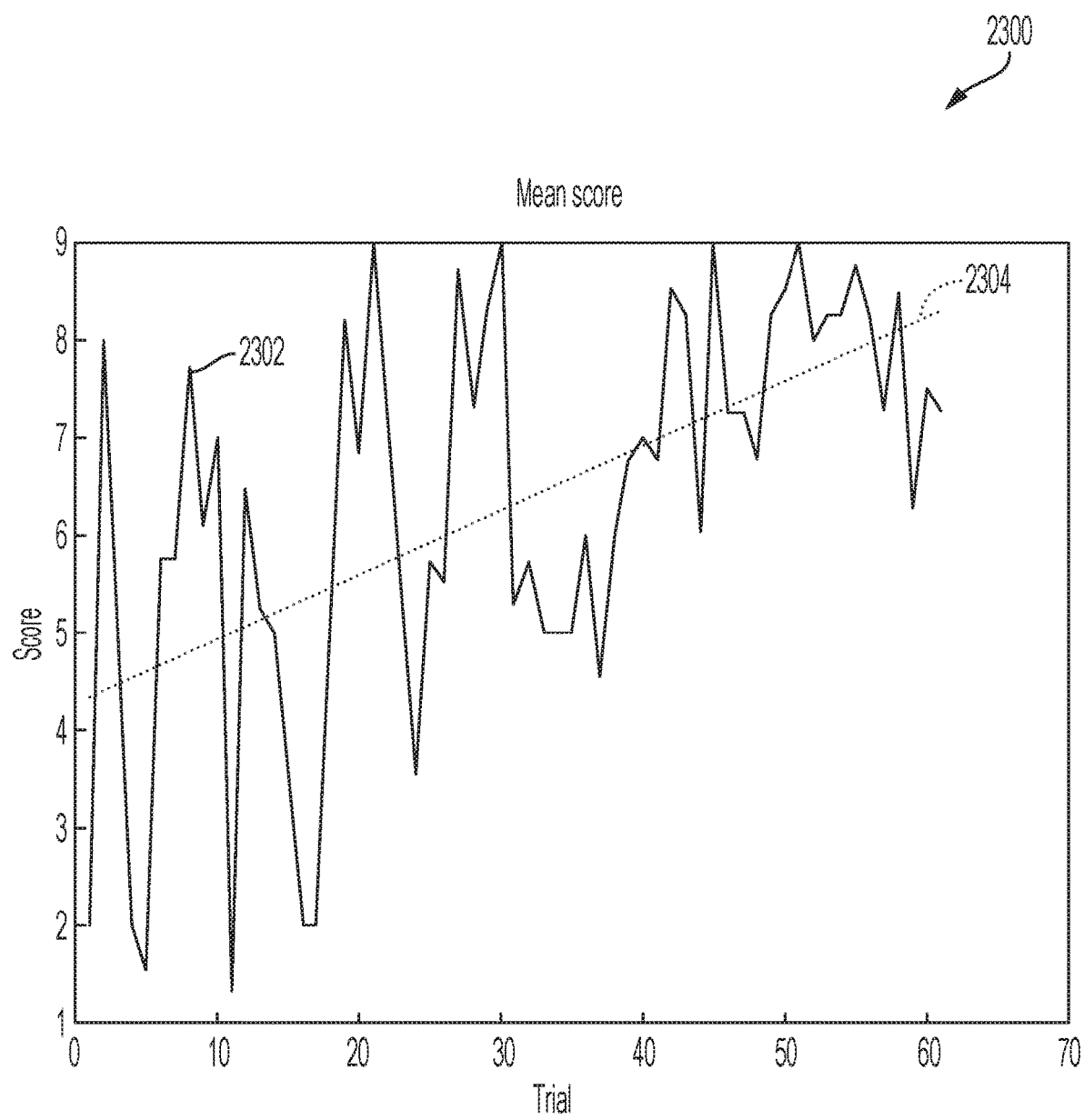

FIG. 23 shows a graph 2300 illustrative of a patient's standing performance during therapy sessions over a one week period during which 70 trials of different complex stimulation waveforms were applied. The score represents a normalized subjective score (e.g., reward) of the patient's ability to stand while a complex stimulation waveform is applied. Solid line 2302 shows the subjective score for the applied waveform. Dashed line 2304 represents a best linear fit to the solid line 2302.

Initially, the example dueling bandits algorithm at the example computing device 152, the external control unit 150, and/or one of the neurostimulator devices 120, 220, 320, and 420 included no data about the patient's spinal cord or responses to waveforms. However, after one week of trials, the example algorithm increased the patient's performance by a factor of 2 such that the final standing score reached 95% of the quality of an optimal pattern found heuristically by clinicians over a three-month period in the same patient. As shown in the graph 2300, the example dueling bandits algorithm does not provide constant improvements, which may be provided by an algorithm that searches for and locks onto a local peak. Instead, exploration among the arms leads to selections that are sometimes less optimal than previous selections. However, over time, this exploration converges on an optimal solution for a patient while avoiding local peaks that may be significantly less optimal. Generally, an optimal or near optimal stimulation arm is located between 2 and 500 trials, preferably between 10 and 100 trials.

Figure 24:
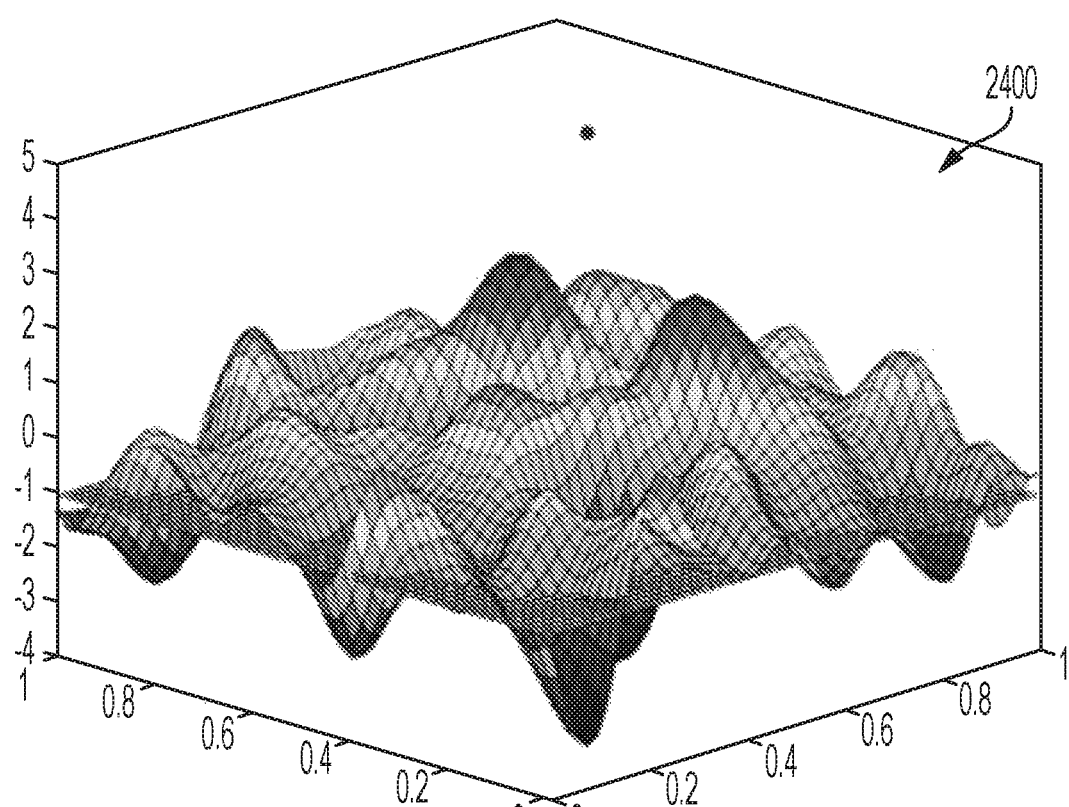

FIG. 24 shows a diagram 2400 illustrative of available arms and corresponding effectiveness. In this illustrated example, the arms were generated using a sampled random function from a zero-mean Gaussian Process with a squared exponential kernel over a sample space D=[0, 1]×[0,1] that is uniformly discretized into 50×50 points, or 2500 correlated arms. A standard deviation of 0.5 was selected for the arms.

The diagram 2400 shows that there are a plurality of local peaks and valleys regarding the effectiveness of arms. Many known algorithms identify a closest peak to a randomly selected point and optimize to a maximum of the peak. However, these algorithms neglect the fact that other larger peaks may exist. By comparison, a known dueling bandits algorithm tests each of the arms to locate the greatest peak. However, the assumed independence between the arms results in an unmanageable number of tests that are unattainable in practice.

Figure 25:
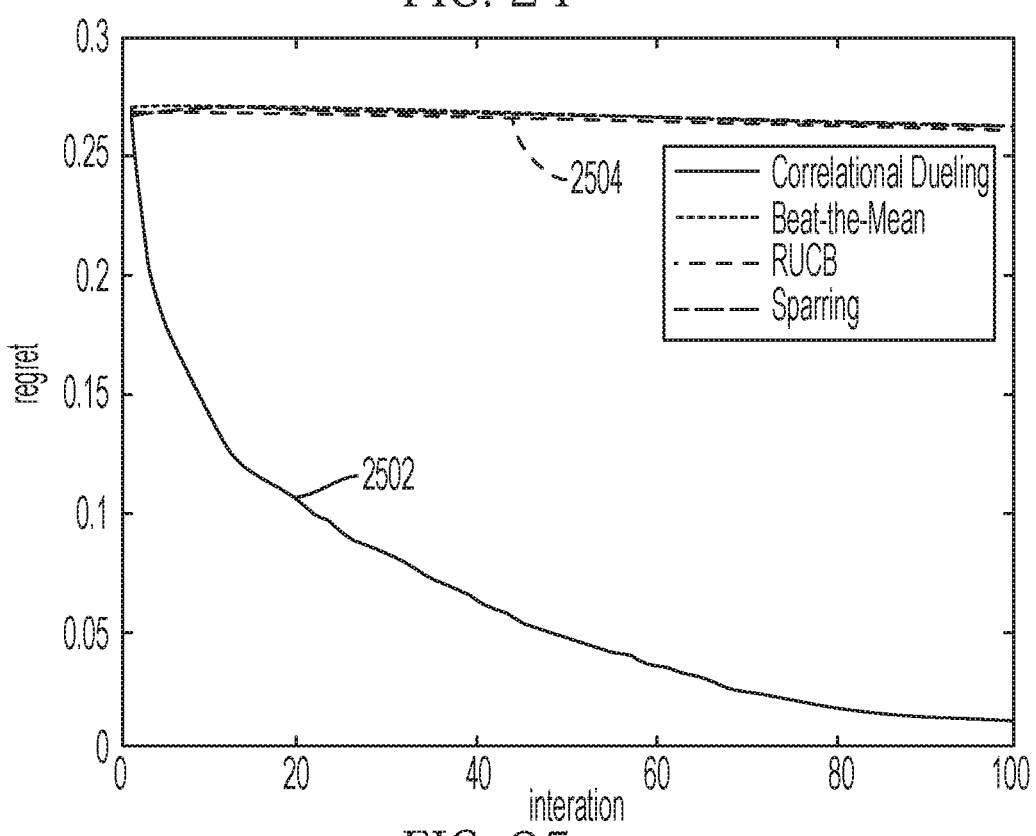

The example dueling bandits algorithm described herein uses correlation among the arms to more quickly converge upon the global peak. In the example of FIG. 24, the example dueling bandits algorithm sampled two points at a time in the active set and compared their sampling values to obtain a {0, 1} feedback or reward of the duel. In the experiment, duels for T=100 iterations for 1000 trials were run. Effectiveness of the dueling bandits algorithm was measured as a cumulative regret of the converged solution. FIG. 25 shows a graph 2500 that illustrates how the regret reduced over the 100 iterations, as shown by line 2502. The reduction in regret simulates the convergence upon more optimal arms (i.e., complex stimulation waveforms). In contrast, calculated regret for known dueling bandits algorithms (that assume independence between arms) including beat-the-mean, relative upper confidence bound ("RUCB"), and sparring is shown in line 2504. The relatively low number of iterations did not provide sufficient time for the known algorithms to converge upon an optimal solution.

FIG. 26 shows diagrams that graphically illustrate correlations between two arms. As discussed above, a similarity of different configurations or stimulation arms corresponds to a correlation coefficient of electrical potential fields generated by the two different configurations. In the illustrated example, graph 2600 illustrates electrical potential fields (estimated from a computational model) that were generated using a first complex stimulation waveform corresponding to the active electrode configuration shown in chart 2602. In addition, graph 2610 illustrates electrical potential fields (estimated using the same computational model) that were generated using a second complex stimulation waveform corresponding to the active electrode configuration shown in chart 2612. The charts 2602 and 2612 show parameters and electrode configurations that have a high degree of correlation between the first and second complex stimulation waveforms. Additionally, graphs 2600 and 2610 show similar induced electrical potential fields. The similarity in induced electrical potential fields confirms the high correlation between the first and second complex stimulation waveforms.

FIG. 27 shows a comparison of a near optimal configuration of complex stimulation waveforms 2702 found by example dueling bandit algorithm over the course of seven clinical testing days compared to optimal complex stimulation waveforms 2704 manually found by a group of clinicians for the same patient over an extended period of time. As illustrated, the example dueling bandits algorithm converged to a set which included the optimal complex stimulation waveforms found by the clinicians (but at a rate much faster than manual experimentation by clinicians), as well as additional high performing electrode stimulation patterns that had not been found manually by experienced clinicians.

In the experiment corresponding to the results shown in FIG. 27, a total of 414 experimental comparisons were done with two patients using the example dueling bandits algorithm with the example computing device 152, the external control unit 150, and/or one of the neurostimulator devices 120, 220, 320, and 420. Each trial lasted up to five minutes. Within each trial, one complex stimulating pattern was generated by a 16-channel electrode. The patterns were unchanged within each trial. For a fixed electrode configuration, the stimulation frequency and amplitude were modulated synergistically to find the best values for an effective weight-bearing standing therapy. Different stimulating waveforms were exploited along the trials to find the most effective waveforms. Specific electrode configuration adjustments were defined to seek improvements of different aspects of motor output. The guideline for the parameter-tuning is related to both previous findings reported in the literature and results of previous experiments performed on the same research patient.

The patient performed experimental and training sessions for standing using a custom designed standing frame comprised of horizontal bars anterior and lateral to the individual. These bars were used for upper extremity support and balance assistance as needed. If the knees or hips flexed beyond a safe standing posture. External assistance was provided at the knees to promote extension, and at the hips to promote hip extension and anterior tilt. Facilitation was provided either manually by a trainer or by elastic bungee cords, which were attached between the two vertical bars of the standing apparatus. Mirrors were placed in front and to the side of the patient to allow a better perception of the body position via visual feedback, conditioned on the lack of proprioceptive sensory feedback.

Stimulation began while the patient was seated. Then the patient initiated the sit to stand transition by positioning his feet shoulder width apart and shifting his weight forward to begin loading the legs. The patient used the horizontal bars of the standing apparatus during the transition phase to balance and to partially pull himself into a standing position.

Trainers positioned at the pelvis and knees manually assisted as needed during the sit to stand transition.

As mentioned above, during the experiments, the example dueling bandits algorithm converged upon near optimal complex stimulation waveforms faster than the manual approach to selecting waveforms. In addition, some of the selected complex stimulation waveforms are identical to the waveforms eventually identified by the clinicians. Moreover, the example dueling bandits algorithm identified other complex stimulation waveforms that were not identified manually by the clinicians. Accordingly, the example dueling bandits algorithm disclosed herein converges relatively quickly on an optimal or near optimal complex stimulation waveforms, thereby improving therapy outcomes for patients.

V. Computing Device

Figure 28:
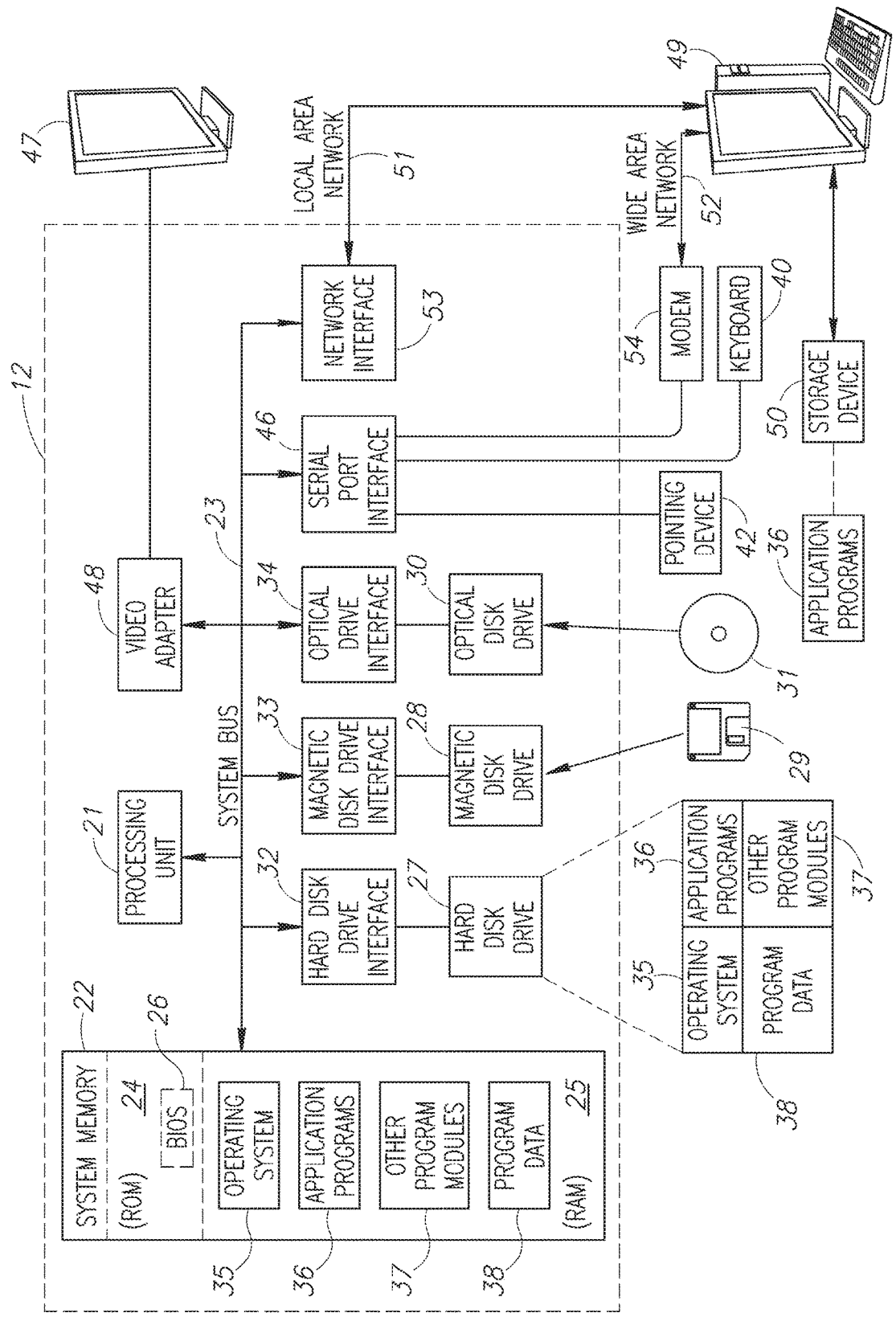
FIG. 28 illustrates a diagram of a hardware environment and an operating environment in which the computing device of the system of FIG. 2 may be implemented.

FIG. 28 illustrates a diagram of hardware and an operating environment in conjunction with which implementations of the computing device 152 and/or the remote computing device 157 may be practiced. The description of FIG. 28 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular data types.

Moreover, those skilled in the art will appreciate that implementations may be practiced with other computer system configurations, including hand-held devices, multi-processor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 28 includes a general-purpose computing device in the form of a computing device 12. The computing device 152 and/or the remote computing device 157 may be substantially identical to the computing device 12. The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like. The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36 (e.g., the example dueling bandits algorithm described above), other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types of physical feedback (e.g., a force feed back game controller).

The input devices described above are operable to receive user input and selections. Together the input and display devices may be described as providing a user interface.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 17 include a local-area network (LAN) 51 and a wide-area network (WAN) 52. Such networking environments are commonplace in offices, enterprise-wide computer networks, intranets and the Internet. Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

In some embodiments, the system memory 22 stores computer executable instructions that when executed by one or more processors cause the one or more processors to perform all or portions of the machine learning method and/or dueling bandits algorithm described above. Such instructions may be stored on one or more non-transitory computer-readable media (e.g., the storage device 460 illustrated in FIG. 12A).

CONCLUSION

It will be appreciated that all of the disclosed methods and procedures described herein can be implemented using one or more computer programs or components. These components may be provided as a series of computer instructions on any computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A neurostimulator device comprising:
   a stimulation assembly connectable to a plurality of electrodes that are configured to apply stimulation waveforms to stimulate a portion of a patient's body;
   a memory storing:
      a plurality of stimulation arms for a correlated dueling bandits algorithm, each of the stimulation arms comprising (i) parameters for defining a stimulation waveform, and (ii) information indicative of at least one electrode of the plurality of electrodes that are to be active for applying the stimulation waveform,
      a correlation index that specifies a correlation among at least some of the plurality of stimulation arms, and
      a feedback index that specifies a feedback reward value for at least some of the plurality of stimulation arms; and
   a processor communicatively coupled to the memory and electrically coupled to the stimulation assembly, the processor configured to:
      operate the correlated dueling bandits algorithm to select a first batch of a specified number of stimulation arms, among the plurality of stimulation arms,
      apply sequentially the stimulation waveforms corresponding to the stimulation arms of the first batch to the patient using the stimulation assembly,
      record a feedback reward value for each of the applied stimulation arms of the first batch indicative of an effectiveness of the respective stimulation arm for a therapy for the patient,
      update the feedback reward value for at least some of the plurality of stimulation arms using the correlation index specifying the correlation among the stimulation arms,
      operate the correlated dueling bandits algorithm to select a second batch of the specified number of stimulation arms, among the plurality of stimulation arms, and
      apply sequentially the stimulation waveforms corresponding to the stimulation arms of the second batch to the patient using the stimulation assembly.

2. The neurostimulator device of claim 1, wherein the processor is configured to filter the plurality of stimulation arms based on at least one of a type of therapy or an indication of a placement of the plurality of electrodes in or on the patient.

3. The neurostimulator device of claim 1, wherein at least a portion of the correlation index and the feedback index are stored with the corresponding stimulation arms.

4. The neurostimulator device of claim 1, wherein the feedback reward value for each of the at least some of the plurality of stimulation arms is at least one of estimated from feedback reward values of correlated stimulation arms and determined from subjective or objective patient feedback to the respective stimulation arm.

5. The neurostimulator device of claim 1, further comprising a sensor configured to measure a response of the patient to the applied stimulation waveforms,
   wherein the processor is configured to determine the feedback reward value for each of the applied stimulation arms based on the measured response.

6. The neurostimulator device of claim 1, wherein the effectiveness of the respective stimulation arm is based on the patient's ability to show improved function in at least one of an autonomic function or a cardiovascular function during application of the stimulation waveforms.

7. The neurostimulator device of claim 6, wherein the neurostimulator device is configured to provide blood pressure regulation by operating the correlated dueling bandits algorithm to determine optimized stimulation waveforms for application over an area of the patient's spinal cord between the 7th and 8th Thoracic vertebrae for 1 millisecond at 5 to 30 Hz using a monophasic waveform, from 0 to 10 milliamps or up to 70 milliamps.

8. The neurostimulator device of claim 1, wherein the effectiveness of the respective stimulation arm is based on the patient's ability to show improved musculoskeletal function while utilizing adjunctive rehabilitation devices and equipment during application of the stimulation waveforms.

9. The neurostimulator device of claim 1, wherein the effectiveness of the respective stimulation arm is based on the patient's ability to move a specified muscle group or limb during application of the stimulation waveform that is defined by the stimulation arm.

10. The neurostimulator device of claim 1, wherein the parameters for defining the stimulation waveform include at least one of a repetition frequency, a pulse width, a system type, a waveform amplitude, an overlapping frequency, and a waveform mode.

11. The neurostimulator device of claim 1, wherein the portion of the patient's body includes at least one of a spinal cord, a portion of a spinal cord, a brain, a brainstem, a nerve, a portion of a nerve, a cell body, a ganglia, a nerve root, or targeted end organ or gland.

12. A neurostimulator method comprising:
(i) operating a processor according to a correlated dueling bandits algorithm to select a first batch of a specified number of stimulation arms, among a plurality of stimulation arms that are stored in a memory, each of the stimulation arms comprising (a) parameters for defining a stimulation waveform, and (b) information indicative of at least one electrode of a plurality of electrodes that are to be active for applying the stimulation waveform;
(ii) operating the processor to apply sequentially the stimulation waveforms corresponding to the stimulation arms of the first batch to a patient using a stimulation assembly comprising the plurality of electrodes that are configured to apply the stimulation waveforms to stimulate a portion of the patient's body;
(iii) recording, via the processor, a feedback reward value for each of the applied stimulation arms of the first batch indicative of an effectiveness of the respective stimulation arm for a therapy for the patient;
(iv) updating, via the processor, a feedback reward value for at least some of the plurality of stimulation arms using a correlation index specifying a correlation among at least some of the plurality of stimulation arms;
(v) operating the processor according to the correlated dueling bandits algorithm to select a second batch of the specified number of stimulation arms, among the plurality of stimulation arms; and
(vi) operating the processor to apply sequentially the stimulation waveforms corresponding to the stimulation arms of the second batch to the patient using the stimulation assembly.

13. The neurostimulator method of claim 12, further comprising:

receiving, in the processor, a subjective score for each of the applied stimulation arms; and
determining, via the processor, the feedback reward value as the subjective score.

14. The neurostimulator method of claim 12, wherein at least one of the stimulation arms of the second batch is more effective for the therapy than the stimulation arms of the first batch.

15. The neurostimulator method of claim 12, wherein steps (iii) to (vi) are repeated an n-number of times to converge upon an optimal or near optimal stimulation arm.

16. The neurostimulator method of claim 12, wherein n is between 2 and 100.

17. A neurostimulator device comprising:
a memory storing:
a plurality of stimulation arms for a correlated dueling bandits algorithm, each of the stimulation arms comprising (i) parameters for defining a stimulation waveform, and (ii) information indicative of at least one electrode of a plurality of electrodes that are to be active for applying the stimulation waveform,
a correlation index that specifies a correlation among at least some of the plurality of stimulation arms, and
a feedback index that specifies a feedback reward value for at least some of the plurality of stimulation arms; and
a processor communicatively coupled to the memory, the processor configured to:
operate the correlated dueling bandits algorithm to select a first batch of a specified number of stimulation arms, among the plurality of stimulation arms,
instruct a stimulation assembly to sequentially apply the stimulation waveforms corresponding to the stimulation arms of the first batch to a patient,
receive a feedback reward value for each of the applied stimulation arms of the first batch indicative of an effectiveness of the respective stimulation arm for a therapy for the patient,
update the feedback reward value for at least some of the plurality of stimulation arms using the correlation index specifying the correlation among the stimulation arms,
operate the correlated dueling bandits algorithm to select a second batch of the specified number of stimulation arms, among the plurality of stimulation arms, and
instruct the stimulation assembly to sequentially apply the stimulation waveforms corresponding to the stimulation arms of the second batch to the patient.

18. The neurostimulator device of claim 17, wherein the processor is configured to filter the plurality of stimulation arms based on at least one of a type of therapy or an indication of a placement of the plurality of electrodes in or on the patient.

19. The neurostimulator device of claim 17, wherein the correlation index specifies a closeness of feedback response values among the stimulation arms.

20. The neurostimulator device of claim 17, wherein the feedback index includes a confidence interval for each of the feedback reward values.

21. The neurostimulator device of claim 6, wherein the autonomic function includes at least one of a bladder function or bowel function, and wherein the cardiovascular function includes blood pressure regulation.

* * * * *